(12) United States Patent
Norton et al.

(10) Patent No.: US 12,209,116 B2
(45) Date of Patent: Jan. 28, 2025

(54) RECOMBINANT HUMAN C1 ESTERASE INHIBITOR AND USES THEREOF

(71) Applicant: TAKEDA PHARMACEUTICAL COMPANY LIMITED, Osaka (JP)

(72) Inventors: Angela W. Norton, Lexington, MA (US); Germano Coppola, Lexington, MA (US)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 15/777,547

(22) PCT Filed: Nov. 18, 2016

(86) PCT No.: PCT/US2016/062906
§ 371 (c)(1),
(2) Date: May 18, 2018

(87) PCT Pub. No.: WO2017/087882
PCT Pub. Date: May 26, 2017

(65) Prior Publication Data
US 2018/0334493 A1    Nov. 22, 2018

Related U.S. Application Data

(60) Provisional application No. 62/257,711, filed on Nov. 19, 2015.

(51) Int. Cl.
| | |
|---|---|
| *C07K 14/81* | (2006.01) |
| *A61K 9/19* | (2006.01) |
| *A61K 38/00* | (2006.01) |
| *A61K 38/57* | (2006.01) |
| *C07K 1/18* | (2006.01) |
| *C07K 14/76* | (2006.01) |

(52) U.S. Cl.
CPC ............ *C07K 14/8121* (2013.01); *A61K 9/19* (2013.01); *A61K 38/57* (2013.01); *C07K 1/18* (2013.01); *C07K 14/76* (2013.01); *A61K 38/00* (2013.01); *C07K 2319/30* (2013.01); *C07K 2319/31* (2013.01); *C07K 2319/91* (2013.01)

(58) Field of Classification Search
None
See application file for complete search history.

(56) References Cited

U.S. PATENT DOCUMENTS

| | | | | |
|---|---|---|---|---|
| 5,622,930 A | * | 4/1997 | Eldering | ............ C07K 14/8121 514/1.4 |
| 6,500,929 B1 | * | 12/2002 | Miyagawa | ......... C07K 14/4703 424/145.1 |
| 2008/0305993 A1 | | 12/2008 | Mannesse et al. | |

FOREIGN PATENT DOCUMENTS

| | | | |
|---|---|---|---|
| EP | 3042952 A1 | 7/2016 | |
| JP | 2013-126992 A | 6/2013 | |
| WO | WO 01/57079 A2 | 8/2001 | |
| WO | WO 2004/034971 | * 4/2004 | |
| WO | WO 2007/073186 | * 6/2007 | ............. A61P 41/00 |
| WO | WO2011/116291 | * 9/2011 | ............. A61K 38/55 |
| WO | WO2013/093027 A1 | 6/2013 | |
| WO | WO2014/135694 | * 9/2014 | ........... A61K 39/395 |
| WO | WO2014/135694 A1 | 9/2014 | |
| WO | WO 2014/145519 A2 | 9/2014 | |
| WO | WO 2015/143199 A1 | 9/2015 | |
| WO | WO2016/070156 A2 | 5/2016 | |
| WO | WO2016/081889 A1 | 5/2016 | |

OTHER PUBLICATIONS

Jonathan A. Bernstein & Joseph J. Moellman, (2012) Progress in the Emergency Management of Hereditary Angioedema: Focus on New Treatment Options in the United States, Postgraduate Medicine, 124:3, 91-100, DOI: 10.3810/pgm.2012.05.2552 (Year: 2012).*
Varga and Farkas, Expert Rev. Clin. Immunol. 2011; 7; 143-153 (Year: 2011).*
Koles et al., Glycobiology, 2004; 14: 51-64; DOI: 10.1093/glycob/cwh010 (Year: 2004).*
Stieber et al., European Journal of Human Genetics, 2017; 25: e1-e4; doi: 10.1038/ejhg.2017.104 (Year: 2017).*
Wissing et al., Proceedings 2015, 9(Suppl 9):P12; May 31-Jun. 3, 2015 (Year: 2015).*
Bos et al., JBC, 2003; 278: 29463-29470 (Year: 2003).*
Bock et al., Biochemistry 1986, 25, 4292-4301 (Year: 1986).*
Stavenhagen et al., Molecular & Cellular Proteomics, 2018; 17: 10.1074/mcp.RA117.000240, 1225-1238 (Year: 2018).*
Coutinho et al., The Journal of Immunology, 1994, 153: 3648 (Year: 1994).*
Ricklin et al., J Immunol (2013) 190 (8): 3839-3847 (Year: 2013).*
Bhattacharya et al., PLoS ONE 12(3): e0171355. https://doi.org/10.1371/journal.pone.0171355; 22 pages total (Year: 2017).*
Plaininc et al., Analytica Chimica Acta 921 (2016) 13-27 (Year: 2016).*
Cevec: "CAP", May 1, 2015, XP055339227, [retrieved on Jan. 26, 2017] the whole document, Retrieved from the Internet: URL: http://www.cevec.com/wp-content/uploads/2015/05/Fly-CAP-GO-Cell-Expression.pdf.

(Continued)

*Primary Examiner* — Christina M Borgeest
(74) *Attorney, Agent, or Firm* — Proskauer Rose LLP

(57) ABSTRACT

The present invention provides, among other things, methods and compositions for treating complement mediated disease. In some embodiments, recombinant human C1 esterase inhibitor proteins having similar or longer half-life than native plasma-derived human C1 esterase inhibitor, and methods of making the same are provided. In some embodiments, the invention provides a method for administering an effective amount of a recombinant human C1 esterase inhibitor protein to an individual who is suffering from or susceptible to a complement-mediated disease such that at least one symptom or feature of said complement-mediated disease is prevented and/or reduced in intensity, severity, or frequency.

9 Claims, 24 Drawing Sheets
Specification includes a Sequence Listing.

(56) References Cited

OTHER PUBLICATIONS

Essers, R. et al., "Improving Volumetric Productivity of a stable human CAP cell line by bioprocess optimization", BMC Proceedings, BIOMED Central Ltd., London UK, vol. 5, No. Suppl. 8, Nov. 22, 2011, pp. 1-3.
Karnaukhova, E., C1-Esterase Inhibitor: Biological Activities and Therapeutic Applications, Journal of Hematology & Thromboembolic Diseases, May 15, 2013, vol. 1, Issue 3, pp. 1-7.
Wissing, S. et al., "Expression of glycoproteins with excellent glycosylation profile and serum half-life in CAP-Go Cells", BMC Proceedings, vol. 9, No. Suppl. 9, Jun. 3, 2015, pp. 1-2.
Wissing, S. et al., "Novel Method for Glycoprotein Expression", Genetic Engineering & Biotechnology News, vol. 35, No. 19, Nov. 1, 2015, pp. 32-33.
Bos et al., "Recombinant human C1-inhibitor produced in Pichia pastoris has the same inhibitory capacity as plasma C1-inhibitor", Biochimica Et Biophysica Acta (BBA)—Proteins & Proteo, Elsevier, Netherlands, vol. 1648, No. 1-2, pp. 75-83, (May 30, 2003).
CHO Consortium, "40 CHO Consortium SBE Special Section SBE Special Section", (Jan. 1, 2007), XP055595207, Retrieved from the Internet: URL:https://pdfs.semanticscholar.org/5f96/12ce9170571f296b75246e80cb671bbb886c.pdf (retrieved on Jun. 11, 2019).
Ruconest® FDA Label and Prescribing Information (PDF).
Yang et al., "Efficient expression of human C1-inhibitor in CHO cells by using a dicistronic expression vector].—PubMed—NCBI", (Jan. 1, 1997), XP055594922, Retrieved from the Internet: URL:https://www.ncbi.nlm.nih.gov/pubmed/10453551 (retrieved on Jun. 7, 2019).
International Search Report and Written Opinion for PCT/US2016/062906, (Apr. 4, 2017).

\* cited by examiner

A

B

| Fraction | Description | Mass rhC1-INH (mg) | Yield |
|---|---|---|---|
| - | Load (503 g/Lm) | 40.3 | - |
| 1A1-1A4 | FT + Wash (20 mM Bis-Tris, 30 mM NaCl | 38.5 | 96% |
| 1B1 | Wash: 20 mM Bis-Tris, ~150-200 mM NaCl | 1.3 | 3% |
| 1B2 | Wash: 20 mM Bis-Tris, 100 mM NaCl | 0 | - |
| 1B3 | Wash: 20 mM Bis-Tris, 150 mM NaCl | 0 | - |
| 1B4 | Wash: 20 mM Bis-Tris, 200 mM NaCl | 0.2 | - |
| 1B5 | Wash: 20 mM Bis-Tris, 250 mM NaCl | 0.1 | - |
| 2A3 | Strip: 2 M NaCl | 0 | - |

| Fraction | Description | Mass rhC1-INH (mg) | Yield |
|---|---|---|---|
| - | Load (503 g/Lm) | 40.3 | - |
| 1A1-1A4 | FT + Wash (20 mM Bis-Tris, 30 mM NaCl) | 35.5 | 88% |
| 1B1 | Wash: 20 mM Bis-Tris, 100 mM NaCl | 0.7 | 2% |
| 1B3 | Wash: 20 mM Bis-Tris, 150 mM NaCl | 0.4 | 1% |
| 1B5 | Wash: 20 mM Bis-Tris, 200 mM NaCl | 0.5 | 1% |
| 1C2 | Wash: 20 mM Bis-Tris, 250 mM NaCl | 0.5 | 1% |
| 1C4 | Wash: 20 mM Bis-Tris, 300 mM NaCl | 0.34 | 1% |
| 2A3 | Strip: 2 M NaCl | 1.3 | 3% |

| Fraction | Description | Mass C36 (mg) | Yield |
|---|---|---|---|
| - | Load (300 g C36/Lm) | 60.0 | - |
| 1C2-2A1 | FT + Wash (20 mM Bis-Tris, 30 mM NaCl) | 21.3 | 35% |
| 2A3 | Wash: 20 mM Bis-Tris, 100 mM NaCl | 8.8 | 15% |
| 2A4 | Wash: 20 mM Bis-Tris, 150 mM NaCl | 0.5 | 12% |
| 2A5 | Wash: 20 mM Bis-Tris, 200 mM NaCl | 0.4 | 7% |
| 2B1 | Wash: 20 mM Bis-Tris, 250 mM NaCl | 0.7 | 1% |
| 2B2 | Wash: 20 mM Bis-Tris, 300 mM NaCl | 0.3 | 1% |
| 2B3 | Strip: 2 M NaCl | 0 | 3% |

RECOMBINANT HUMAN C1 ESTERASE INHIBITOR AND USES THEREOF

RELATED APPLICATIONS

This application is a 35 U.S.C. § 371 National Stage Application of International Application No. PCT/US16/62906, filed Nov. 18, 2016, which claims priority to, and the benefit of, U.S. provisional application No. 62/257,711 filed on Nov. 19, 2015, the content of each of which is hereby incorporated by reference in its entirety.

INCORPORATION-BY-REFERENCE OF SEQUENCE LISTING

The contents of the text file named "SHR-1234WO Sequence Listing_ST25.txt", which was created on Nov. 16, 2016 and is 15 KB in size, are hereby incorporated by reference in their entirety.

BACKGROUND

C1-inhibitor (C1-INH), also known as C1 esterase inhibitor, is the largest member of the serpin protein superfamily. It is a heavily glycosylated serine proteinase inhibitor having the main function of inhibiting the spontaneous activation of the complement system. C1-INH regulates the complement cascade system, plays a key role in the regulation of the contact (kallikrein-kinin) amplification cascade, and participates in the regulation of the coagulation and fibrinolytic systems. See Karnaukhova, E., *C1-Esterase Inhibitor: Biological Activities and Therapeutic Applications*. J Hematol Thromb Dis, 1: 113 (2013).

Dysfunction and/or deficiency of C1-INH in subjects has been correlated with a variety of autoimmune disease due to the failure of C1-INH to inhibit the activation of the complement system. An example of such a disease is hereditary angioedema (HAE), a rare, but potentially life-threatening disorder characterized by unpredictable and recurrent attacks of inflammation. Symptoms of HAE attacks include swelling of the face, mouth, and/or airway that occur spontaneously or are triggered by mild trauma. Such swelling can also occur in any part of the body. In some cases, HAE is associated with low plasma levels of C1-inhibitor, while in other cases the protein circulates in normal or elevated amounts but it is dysfunctional. In addition to the episodes of inflammation, it also can cause more serious or life threatening indications, such as autoimmune diseases or lupus erythematosus.

CINRYZE®, a human plasma derived C1 esterase inhibitor, has been approved for prophylactic use and treatment of acute attacks of HAE. Berinert® (also a plasma-derived human C1-INH, CSL Behring) is indicated for treatment of acute HAE attack. The supply of human plasma derived C1 esterase inhibitor is tied to the availability of blood and plasma donations. Ruconest® (conestat alfa, Pharming N.V.) a recombinant C1-INH expressed in engineered rabbits is indicated for IV administration for treatment of acute HAE attack. Although Ruconest® has the same amino acid sequence as human plasma derived C1-INH, since it is made in rabbits, its glycosylation profile is very different from that of human plasma-derived C1-INH. The result is that Ruconest has an extremely short half-life of about 2.4-2.7 hours. See Ruconest® FDA Label and Prescribing Information.

Therefore, it remains a need in the art for an improved recombinant human C1 esterase inhibitor for the treatment of various C1 esterase mediated indications.

SUMMARY OF THE INVENTION

The present invention provides, among other things, improved long-acting recombinant human C1 esterase inhibitors (rhC1-INH) that can be used to effectively treat various complement-mediated disorders and that can be manufactured in a cost-effective matter.

In particular, the present invention provides recombinant C1 esterase inhibitor proteins that exhibit longer half-life than Ruconest® (conestat alfa). In some embodiments, the rhC1-INH proteins of the invention exhibit a half-life comparable to or longer than plasma-derived C1-INH. For example, the present inventors have demonstrated that certain exemplary rhC1-INH proteins according to the present invention have extended serum half-life of at least 4 days. It is contemplated that the long serum half-life of an rhC1-INH leads to superior in vivo efficacy and permits a preferable dosing regimen and route of administration. In certain embodiments, the rhC1-INH proteins of the invention may be administered subcutaneously with similar or reduced frequency compared to approved intravenously administered C1 esterase inhibitors, while still achieving desired efficacy (e.g., prophylaxis). Moreover, the rhC1-INH proteins of the invention can be produced recombinantly in host cells such that the disclosed rhC1-INH proteins are not dependent on blood supply, do not pose a risk of transmission of infectious agents, and are less expensive to manufacture. Ruconest also carries the risk of hypersensitivity and/or anaphylaxis reactions due to the presence of rabbit host-related impurities. Ruconest cannot be administered to any patient having a known sensitivity or allergy to rabbits or products from rabbits, nor is it indicated for administration in children.

Since the present invention provides recombinant C1 esterase inhibitor proteins that are recombinantly produced in host cells, they offer more consistency in production and final product than those products purified from human blood, human blood components (e.g. plasma), or animal milk. Moreover, the rhC1-INH proteins provided herein, unlike Ruconest, are not dependent on animal husbandry considerations, including animal age and/or maturity, milk production, animal illness, etc., all of which may affect both quantity and quality (e.g., glycosylation profile, heterogeneity of expressed protein, host-related impurities, etc.) of the rabbit expressed C1-INH.

In one embodiment, the present invention provides a composition that includes purified recombinant human C1 esterase inhibitor (rhC1-INH) having an amino acid sequence at least about 50%, 55%, 60%, 65%, 70%, 75%, 80%, 85%, 90%, 95%, 96%, 97%, 98%, 99%, or 100% identical to SEQ ID NO:1 or SEQ ID NO:2, wherein the purified recombinant human C1 esterase inhibitor has a half-life similar to or longer than plasma derived human C1 esterase inhibitor.

In one embodiment, the present invention provides a composition that includes purified recombinant human C1 esterase inhibitor (rhC1-INH) having an amino acid sequence at least about 50%, 55%, 60%, 65%, 70%, 75%, 80%, 85%, 90%, 95%, 96%, 97%, 98%, 99%, or 100% identical to SEQ ID NO:1 or SEQ ID NO:2, wherein the purified recombinant human C1 esterase inhibitor has a half-life of at least about 10, 15, 20, 25, 30, 35, 40, 45, 50, 55, 60, 65, or 70 hours.

In one aspect, the recombinant rhC1-INH protein comprises the amino acid sequence identical to SEQ ID NO:1. In another aspect, the purified recombinant rhC1-INH comprises the amino acid sequence identical to SEQ ID NO:2.

In another aspect, the purified recombinant rhC1-INH has a glycosylation profile comprising no more than about 50%, 45%, 40%, 35%, 30%, 25%, 20%, 15%, 10%, or 5% neutral glycan species. In another aspect, the recombinant rhC1-INH protein is a fusion protein. In another aspect, the recombinant rhC1-INH protein comprises an Fc domain fused directly or indirectly to a C1-INH domain. In another aspect, the recombinant rhC1-INH protein comprises an albumin domain fused directly or indirectly to a C1-INH domain. In another aspect, the purified recombinant rhC1-INH has a glycosylation profile comprising between about 5% and about 25% neutral glycan species. In another aspect, the purified recombinant rhC1-INH contains less than about 20%, 15%, 10%, 5%, or 0% of one or more of mannose, α-galactose, NGNA, and/or oligomannose-type glycosylation. In another aspect, the purified recombinant rhC1-INH has a glycosylation profile comprising no more than about 30% neutral glycan species and sufficient sialylated glycan species such that the purified rhC1-INH has a half-life similar to or longer than plasma derived C1-INH. In another aspect, the purified recombinant rhC1-INH has a glycosylation profile comprising at least one of the following: between about 5% and about 30% neutral glycan species; between about 10% and about 30% mono-sialylated glycan species; between about 30% and about 50% di-sialylated glycan species; between about 15% and about 35% tri-sialylated glycan species; or between about 5% and about 15% tetra-sialylated glycan species.

In another aspect, the purified recombinant rhC1-INH has a glycosylation profile that includes the following: no more than 30% neutral glycan species; between about 20% and about 30% mono-sialylated glycan species; between about 30% and about 40% di-sialylated glycan species; between about 10% and about 20% tri-sialylated glycan species; and between about 5% and about 10% tetra-sialylated glycan species.

In one embodiment, the present invention provides a composition comprising purified recombinant human C1 esterase inhibitor (rhC1-INH) having an amino acid sequence at least 50%, 55%, 60%, 65%, 70%, 75%, 80%, 85%, 90%, 95%, 96%, 97%, 98%, 99%, or 100% identical to SEQ ID NO:1 or SEQ ID NO:2, wherein the purified recombinant rhC1-INH comprises, on average, at least about 10, 11, 12, 13, or 14 sialylated glycan residues per molecule and has a half-life similar to or longer than human plasma derived C1 esterase inhibitor.

In one aspect, the purified recombinant rhC1-INH includes, on average, at least about 15, 16, 17, 18, 19, 20, 21, 22, 23, 24, 25, 26, 27, 28, or 29 sialylated glycan residues per molecule. In another aspect, the purified recombinant rhC1-INH includes, on average, at least about 30, 31, 32, 33, 34, 35, 36, 37, 38, 39, or 40 sialylated glycan residues per molecule.

In one embodiment, the present invention provides a composition including purified recombinant human C1 esterase inhibitor (rhC1-INH) having an amino acid sequence at least 50%, 55%, 60%, 65%, 70%, 75%, 80%, 85%, 90%, 95%, 96%, 97%, 98%, 99%, or 100% identical to SEQ ID NO:1 or SEQ ID NO:2, wherein the purified recombinant rhC1-INH comprises, on average, at least about 30%, 35%, 40%, 45%, 50%, 55%, 60%, 65%, 70%, 75%, 80%, 85%, 90%, 95%, 96%, 97%, 98%, 99%, or 100% charged glycans per molecule and has a half-life similar to or longer than human plasma derived C1 esterase inhibitor.

In one aspect, the purified recombinant rhC1-INH includes, on average, at least about 15, 16, 17, 18, 19, 20, 21, 22, 23, 24, 25, 26, 27, 28, 29, 30, 31, 32, 33, 34, 35, 36, 37, 38, 39, or 40 mole sialic acid per mole of protein. In another aspect, the purified recombinant rhC1-INH has a half-life in the range of 50%-150% of the half-life of plasma-derived human C1 esterase inhibitor. In another aspect, the purified recombinant rhC1-INH has a half-life in the range of 80%-120% of the half-life of plasma-derived human C1 esterase inhibitor. In another aspect, the purified recombinant rhC1-INH has a half-life similar to or longer than the half-life of plasma-derived human C1 esterase inhibitor. In another aspect, the purified recombinant rhC1-INH protein is stable as a liquid product at concentrations exceeding about 20 mg/mL. In another aspect, the purified recombinant rhC1-INH protein is stable as a liquid product at concentrations exceeding about 60 mg/mL. In another aspect, the purified recombinant rhC1-INH protein is stable as a liquid product at concentrations of about 70 mg/mL or more. In another aspect, the purified recombinant rhC1-INH protein is stable as a liquid product at concentrations of about 100 mg/mL or more. In another aspect, the purified recombinant rhC1-INH protein is stable as a liquid product at concentrations exceeding about 50, 100, 150, 200, 250, 300, 350, 400, 450, 500, 550, 600, 650, 700, or 750 U/mL.

In one embodiment, the present invention provides a nucleic acid encoding a recombinant human C1 esterase inhibitor (rhC1-INH) having an amino acid sequence at least 50%, 55%, 60%, 65%, 70%, 75%, 80%, 85%, 90%, 95%, 96%, 97%, 98%, 99%, or 100% identical to SEQ ID NO:1 or SEQ ID NO:2.

In one aspect, the present invention provides a cell that includes the nucleic acid encoding a recombinant human C1 esterase inhibitor (rhC1-INH) having an amino acid sequence at least 50%, 55%, 60%, 65%, 70%, 75%, 80%, 85%, 90%, 95%, 96%, 97%, 98%, 99%, or 100% identical to SEQ ID NO:1 or SEQ ID NO:2.

In one embodiment, the present invention provides a host cell that includes an expression vector encoding a recombinant human C1 esterase inhibitor (rhC1-INH) having an amino acid sequence at least 50%, 55%, 60%, 65%, 70%, 75%, 80%, 85%, 90%, 95%, 96%, 97%, 98%, 99%, or 100% identical to SEQ ID NO:1 or SEQ ID NO:2, wherein said host cell, once cultivated under a cell culture condition, is capable of expressing the recombinant rhC1-INH at a titer between about 0.1 g/L to about 10.0 g/L.

In one embodiment, the present invention provides a host cell that includes an expression vector encoding a recombinant human C1 esterase inhibitor (rhC1-INH) having an amino acid sequence at least 50%, 55%, 60%, 65%, 70%, 75%, 80%, 85%, 90%, 95%, 96%, 97%, 98%, 99%, or 100% identical to SEQ ID NO:1 or SEQ ID NO:2, wherein said host cell, once cultivated under a cell culture condition, is capable of expressing the recombinant rhC1-INH at a specific productivity rate of greater than about 2, 3, 4, 5, 6, 7, 8, 9, or 10 picograms/cell/day.

In one aspect, the host cell, once cultivated under a cell culture condition, is capable of expressing the recombinant rhC1-INH at a specific productivity rate of greater than about 10, 15, 20, 25, 30, 35, 40, 45, or 50 picograms/cell/day. In another aspect, the host cell is a mammalian cell. In another aspect, the mammalian cell is a CHO cell. In another aspect, the mammalian cell is a human cell. In another aspect, the human cell is a HT1080 or HEK cell. In another aspect, the host cell is engineered to increase sialylation of the expressed recombinant rhC1-INH.

In one embodiment, the present invention provides a host cell that includes an expression vector encoding a recombinant human C1 esterase inhibitor (rhC1-INH) having an amino acid sequence at least 50%, 55%, 60%, 65%, 70%, 75%, 80%, 85%, 90%, 95%, 96%, 97%, 98%, 99%, or 100% identical to SEQ ID NO:1 or SEQ ID NO:2, wherein the recombinant rhC1-INH protein is engineered to increase sialylation.

In one aspect, the host cell is engineered to express a heterologous enzyme to increase sialylation, engineered to express a mutant heterologous enzyme to increase sialylation, engineered to overexpress an endogenous enzyme to increase sialylation, engineered to express an mutated endogenous enzyme to increase sialylation, and/or engineered to reduce or prevent expression of endogenous enzymes that reduce, inhibit, or degrade sialylation. In one aspect, present invention provides a method of producing recombinant human C1 esterase inhibitor (rhC1-INH) that includes culturing the host cell.

In one aspect, the method of producing recombinant human C1 esterase inhibitor (rhC1-INH) includes the steps of: providing a host cell engineered to express rhC1-INH comprising an amino acid sequence at least 50%, 55%, 60%, 65%, 70%, 75%, 80%, 85%, 90%, 95%, 96%, 97%, 98%, 99%, or 100% identical to SEQ ID NO:1 or SEQ ID NO:2; and culturing the host cell under conditions suitable for the cell to produce rhC1-INH, wherein the conditions comprise feeding the cells with a culture medium comprising a glycosylation modulator for at least a period of time. In another aspect, the cells are cultured between about 30° C. to 34° C. for at least a period of time.

In one embodiment, the present invention provides a method for large-scale production of recombinant human C1 esterase inhibitor (rhC1-INH) protein in mammalian cells, including culturing mammalian cells expressing a recombinant rhC1-INH protein in suspension in a large-scale culture vessel, wherein the recombinant human C1 esterase inhibitor has a half-life similar to or longer than human plasma derived C1 esterase inhibitor.

In one aspect, the cells co-express a glycan modifying construct. In another aspect, the glycan modifying construct increases sialylation. In another aspect, the mammalian cells are cultured in a cell culture medium lacking serum. In another aspect, the large-scale culture vessel is a bioreactor. In another aspect, the bioreactor is at a scale of or greater than about 5 L, 10 L, 200 L, 500 L, 1,000 L, 1,500 L, 2,000 L, 5,000 L, 10,000 L, 15,000 L, or 20,000 L. In another aspect, the culturing step comprises a perfusion process. In another aspect, the culturing step comprises a fed-batch process. In another aspect, the cells are cultured in a fed-batch process at 30-34° C. for at least a period of time. In another aspect, the cells, on average, produce the recombinant rhC1-INH protein at a specific productivity rate of greater than about 5 picogram/cell/day. In another aspect, the cells, on average, produce the recombinant rhC1-INH protein at a specific productivity rate of greater than about 10 picogram/cell/day. In another aspect, the cells produce the recombinant rhC1-INH protein at an average harvest titer of at least about 5, 6, 8, 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 mg per liter per day. In another aspect, the mammalian cells are human cells. In another aspect, the mammalian cells are CHO cells.

In one aspect, the medium lacks animal-derived components. In another aspect, the medium is chemically-defined medium. In another aspect, the medium is protein free. In another aspect, the medium comprises at least one glycosylation modulator. In another aspect, the medium includes at least one growth-modulator. In another aspect, the at least one growth-modulator includes hypoxanthine. In one aspect, hypoxanthine is at a concentration ranging from about 0.1 mM to about 10 mM. In one aspect, the at least one growth-modulator comprises thymidine. In one aspect, the thymidine is at a concentration ranging from about 1 µM to about 100 mM. In one aspect, the medium has a pH ranging from about 6.8-7.5. In one aspect, the medium has a pH ranging from about 6.9-7.3. In one aspect, the culturing step comprises maintaining a dissolved oxygen set point of between about 20% to about 40% dissolved oxygen. In one aspect, the culturing step comprises a growth phase and a production phase. In one aspect, the mammalian cells are cultured at a temperature ranging from 30-37° C. In one aspect, the mammalian cells are cultured at different temperatures during the growth phase and the production phase. In one aspect, the mammalian cells are cultured at about 37° C. during the growth phase and between about 32° C.-34° C. during the production phase. In one aspect, the medium for the growth phase and the production phase has different pH.

In one aspect the method further comprises a step of harvesting the recombinant rhC1-INH protein. In one aspect, the recombinant rhC1-INH protein comprises an amino acid sequence at least 50%, 55%, 60%, 65%, 70%, 75%, 80%, 85%, 90%, 95%, 96%, 97%, 98%, 99%, or 100% identical to SEQ ID NO:1 or SEQ ID NO:2. In one aspect, one or more of pH, gassing, and temperature of the culture are controlled to allow sufficient sialyation of the rhC1-INH molecule to provide a half-life similar to or longer than human plasma derived C1 esterase inhibitor.

In one embodiment, the present invention provides a method of purifying recombinant human C1 esterase inhibitor (rhC1-INH) from an impure preparation, the method includes one or more steps of affinity chromatography, anion-exchange chromatography, cation-exchange chromatography, mixed-mode chromatography, and hydrophobic interaction chromatography, wherein the purified rhC1-INH protein is at least 90% pure and has a half-life similar to or longer than human plasma derived C1 esterase inhibitor.

In one aspect, the impure preparation comprises cell culture medium. In another aspect, the method includes performing anion exchange (AEX) chromatography to reduce process impurities and unwanted glycan species. In another aspect, the method includes performing cation exchange (CEX) chromatography to reduce process impurities and unwanted glycan species. In another aspect, the method includes performing anion exchange (AEX) chromatography, cation exchange (CEX) chromatography, and hydrophobic interaction (HIC) chromatography. In another aspect, the method further includes one or more viral inactivation and/or removal steps. In another aspect, the viral inactivation and/or removal steps selected from a filtration step, solvent viral inactivation step, and a detergent inactivation step. In one aspect, the purified recombinant rhC1-INH protein, on average, includes no more than about 50%, 45%, 40%, 35%, 30%, 25%, 20%, 15%, 10%, or 5% neutral glycan species. In one aspect, the purified recombinant rhC1-INH has a half-life in the range of 50%-150% of the half-life of plasma-derived human C1 esterase inhibitor. In one aspect, the purified recombinant rhC1-INH has a half-life in the range of 80%-120% of the half-life of plasma-derived human C1 esterase inhibitor. In one aspect, the purified recombinant rhC1-INH protein is stable as a liquid product at concentrations exceeding about 20 mg/mL. In one aspect, the purified recombinant rhC1-INH protein is stable as a liquid product at concentrations exceeding about 60 mg/mL. In one aspect, the purified recombinant rhC1-INH protein is stable as a liquid product at concentrations of about 70 mg/mL or more.

In one aspect, the present invention provides a pharmaceutical composition that includes a purified recombinant human C1 esterase inhibitor protein and a pharmaceutically acceptable carrier.

In one aspect, the pharmaceutical composition includes the recombinant human C1 esterase inhibitor protein in a formulation buffer that includes 50 mM Tris, 50 mM sorbitol, and 150 mM glycine, wherein the composition has a pH of 7.2. In one aspect, the pharmaceutical composition is liquid. In one aspect, the pharmaceutical composition is lyophilized. In one aspect, the pharmaceutical composition is reconstituted with a suitable buffer for reconstitution. In one aspect, the suitable buffer for reconstitution is selected from sterile water, a sterile saline solution, a sterile buffer solution, or a sterile solution comprising one or pharmaceutically acceptable carriers. In one aspect, the purified recombinant rhC1-INH protein is stable as a liquid product at concentrations exceeding about 20 mg/mL. In one aspect, the purified recombinant rhC1-INH protein is stable as a liquid product at concentrations exceeding about 60 mg/mL. In one aspect, the purified recombinant rhC1-INH protein is stable as a liquid product at concentrations of about 70 mg/mL or more. In one aspect, the purified recombinant rhC1-INH protein is stable as a liquid product at concentrations of about 100 mg/mL or more. In one aspect, the purified recombinant rhC1-INH protein is stable as a liquid product at concentrations exceeding about 50, 100, 150, 200, 250, 300, 350, 400, 450, 500, 550, 600, 650, 700, or 750 U/mL.

In one aspect, a kit is provided. In one aspect, the kit further includes a syringe. In one aspect, the syringe is preloaded with the pharmaceutical composition. In one aspect, the kit that includes the pharmaceutical composition also includes a buffer for reconstitution, wherein mixing the lyophilized composition and the buffer for reconstitution produces the composition. In one aspect, the kit further includes a syringe.

In one embodiment, the present invention provides a method of treating a complement-mediated disorder that includes administering to a subject in need of treatment a pharmaceutical composition. In one aspect, the complement-mediated disorder is selected from hereditary angioedema, antibody mediated rejection, neuromyelitis optica spectrum disorders, traumatic brain injury, spinal cord injury, ischemic brain injury, burn injury, toxic epidermal necrolysis, multiple sclerosis, amyotrophic lateral sclerosis (ALS), Parkinson's disease, stroke, chronic inflammatory demyelinating polyneuropathy (CIDP), myasthenia gravis, multifocal motor neuropathy.

In one embodiment, the present invention provides use of a composition that includes a recombinant human C1-esterase inhibitor, in the manufacture of a medicament for treating a complement mediated disorder. In one aspect, the complement-mediated disorder is selected from hereditary angioedema, antibody mediated rejection, neuromyelitis optica spectrum disorders, traumatic brain injury, spinal cord injury, ischemic brain injury, burn injury, toxic epidermal necrolysis, multiple sclerosis, amyotrophic lateral sclerosis (ALS), Parkinson's disease, stroke, chronic inflammatory demyelinating polyneuropathy (CIDP), myasthenia gravis, and/or multifocal motor neuropathy.

Thus, the present invention provides for the cost effective and reliable manufacturing of rhC1-INH inhibitors, and safer, more effective treatment of HAE and other complement-mediated disorders. Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings are for illustration purposes only, not for limitation.

FIG. 18, panel A, is a chromatogram that shows the results of a spiking study with Sartobind Q (undiluted load); FIG. 18, panel B, is a chromatogram that shows the results of a spiking study with Sartobind Q (diluted load);

FIG. 18, panel C, is a chromatogram that shows the results of a spiking study with Sartobind STIC.

DEFINITIONS

Figure 1:
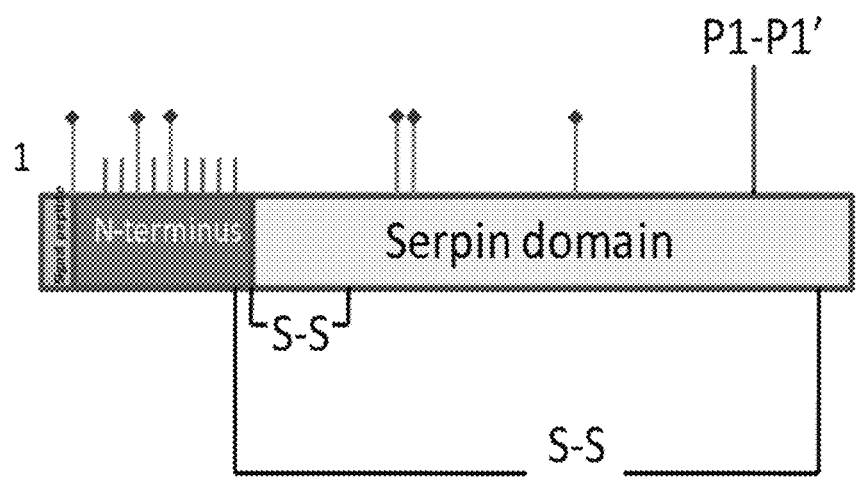
FIG. 1 is a schematic representation of C1-INH. From left to right the three domains are the signal peptide, the N-terminus, also referred to as N-terminal domain, and the serpin domain. N-linked glycans are shown as long vertical lines with diamond heads and O-linked glycans are shown as short vertical lines.

In order for the present invention to be more readily understood, certain terms are first defined below. Additional definitions for the following terms and other terms are set forth throughout the specification.

As used herein certain terms have the following defined meanings. As used in the specification and claims, the singular form "a", "an" and "the" include plural references unless the context clearly dictates otherwise. For example, the term "a cell" includes a plurality of cells, including mixtures thereof.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used in this application, the terms "about" and "approximately" are used as equivalents. Any numerals used in this application with or without about/approximately are meant to cover any normal fluctuations appreciated by one of ordinary skill in the relevant art. As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Bioavailability: As used herein, the term "bioavailability" generally refers to the percentage of the administered dose that reaches the blood stream of a subject.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a peptide is biologically active, a portion of that peptide that shares at least one biological activity of the peptide is typically referred to as a "biologically active" portion.

Carrier or diluent: As used herein, the terms "carrier" and "diluent" refers to a pharmaceutically acceptable (e.g., safe and non-toxic for administration to a human) carrier or diluting substance useful for the preparation of a pharmaceutical formulation. Exemplary diluents include sterile water, bacteriostatic water for injection (BWFI), a pH buffered solution (e.g. phosphate-buffered saline), sterile saline solution, Ringer's solution or dextrose solution.

C1-inhibitor or C1 esterase inhibitor or C1-INH: As used herein, the term "C1-inhibitor" or "C1 esterase inhibitor" or "C1-INH" can all be used interchangeably and refer to any wild-type, native, or naturally occurring or modified C1-INH polypeptides (e.g., C1-INH proteins with one or more amino acid mutations, truncations, deletions, insertions, and/or fusion proteins) that retain substantial C1-INH biological activity unless otherwise specified. In some embodiments a C1-INH fusion protein comprises a C1-INH polypeptide and an Fc domain. In some embodiments a C1-INH fusion protein comprises a C1-INH polypeptide and an albumin domain. In some embodiments the fusion protein further comprises a linker. C1-INH may be recombinantly expressed in cells. In certain embodiments, the rhC1-INH is expressed in mammalian cells, preferably CHO cells, or human cells, preferably HT1080 or HEK cells.

Functional equivalent or derivative: As used herein, the term "functional equivalent" or "functional derivative" denotes, in the context of a functional derivative of an amino acid sequence, a molecule that retains a biological activity (either function or structural) that is substantially similar to that of the original sequence. A functional derivative or equivalent may be a natural derivative or is prepared synthetically. Exemplary functional derivatives include amino acid sequences having substitutions, deletions, or additions of one or more amino acids, provided that the biological activity of the protein is conserved. The substituting amino acid desirably has chemico-physical properties which are similar to that of the substituted amino acid. Desirable similar chemico-physical properties include, similarities in charge, bulkiness, hydrophobicity, hydrophilicity, and the like.

Fusion protein: As used herein, the term "fusion protein" or "chimeric protein" refers to a protein created through the joining of two or more originally separate proteins, or portions thereof. In some embodiments, a linker or spacer will be present between each protein.

Half-Life: As used herein, the term "half-life" is the time required for a quantity such as protein concentration or activity to fall to half of its value as measured at the beginning of a time period.

Hereditary angioedema or HAE: As used herein, the term "hereditary angioedema" or "HAE" refers to a blood disorder characterized by unpredictable and recurrent attacks of inflammation. HAE is typically associated with C1-INH deficiency, which may be the result of low levels of C1-INH or C1-INH with impaired or decreased activity. Symptoms include, but are not limited to, swelling that can occur in any part of the body, such as the face, extremities, genitals, gastrointestinal tract, and upper airways.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Situ: As used herein, the term "in situ" refers to events that occur in an original, natural, existing place or position, or environment.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Linker: As used herein, the term "linker" refers to, in a fusion protein, an amino acid sequence other than that appearing at a particular position in the natural protein and is generally designed to be flexible or to interpose a structure, such as an α-helix, between two protein moieties. A linker is also referred to as a spacer. A linker or a spacer typically does not have biological function on its own.

Polypeptide: The term "polypeptide" as used herein refers to a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified. As used herein, the terms "polypeptide" and "peptide" are used inter-changeably.

Prevent: As used herein, the term "prevent" or "prevention", when used in connection with the occurrence of a disease, disorder, and/or condition, refers to reducing the risk of developing the disease, disorder and/or condition. See the definition of "risk."

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" refers to the multiple polypeptides that are physically coupled and function together as the discrete unit.

Risk: As will be understood from context, a "risk" of a disease, disorder, and/or condition comprises a likelihood that a particular individual will develop a disease, disorder, and/or condition (e.g., muscular dystrophy). In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event (e.g., muscular dystrophy). In some embodiments a reference sample or group of reference samples are from individuals comparable to a particular individual. In some embodiments, relative risk is 0, 1, 2, 3, 4, 5, 6, 7, 8, 9, 10, or more.

Stability: As used herein, the term "stable" refers to the ability of the therapeutic agent (e.g., a recombinant protein) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In the context of a formulation, a stable formulation is one in which the therapeutic agent therein essentially retains its physical and/or chemical integrity and biological activity upon storage and during processes (such as freeze/thaw, mechanical mixing and lyophilization). For protein stability, it can be measured by formation of high molecular weight (HMW) aggregates, loss of enzyme activity, generation of peptide fragments and shift of charge profiles.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues with appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues. In some embodiments, conservative substitutions of amino acids include substitutions made among amino acids within the following groups: (a) M, I, L, V; (b) F, Y, W; (c) K, R, H; (d) A, G; (e) S, T; (f) Q, N; and (g) E, D. In some embodiments, a "conservative amino acid substitution" refers to an amino acid substitution that does not alter the relative charge or size characteristics of the protein in which the amino acid substitution is made Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.,* 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

As used herein, "percent (%) amino acid sequence identity" with respect to a reference protein sequence (e.g., a reference Cl-INH protein sequence) identified herein is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al, Methods in Enzymology 266, 460-480 (1996)). WU-BLAST-2 uses several search parameters, most of which are set to the default values. The adjustable parameters are set with the following values: overlap span=1, overlap fraction=0.125, world threshold (T)=ll. HSP score(S) and HSP S2 parameters are dynamic values and are established by the program itself, depending upon the composition of the particular sequence, however, the minimum values may be adjusted and are set as indicated above.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, condition, or event (for example, DMD) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein associated with the disease, disorder, and/or condition; (4) habits and/or lifestyles associated with development of the disease, disorder, condition, and/or event (5) having undergone, planning to undergo, or requiring a transplant. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION OF CERTAIN EMBODIMENTS

The present invention provides, among other things, methods and compositions for treating complement-mediated disorders, including Hereditary angioedema (HAE), using rhC1-INH as a protein therapeutic.

Various aspects of the invention are described in detail in the following sections. The use of sections is not meant to limit the invention. Each section can apply to any aspect of the invention. In this application, the use of "or" means "and/or" unless stated otherwise. The disclosures of all of the art cited herein are incorporated by reference in their entirety.

C1-INH

Human C1-INH is an important anti-inflammatory plasma protein with a wide range of inhibitory and non-inhibitory biological activities. By sequence homology, structure of its C-terminal domain, and mechanism of protease inhibition, it belongs to the serpin superfamily, the largest class of plasma protease inhibitors, which also includes antithrombin, al-proteinase inhibitor, plasminogen activator inhibitor, and many other structurally similar proteins that regulate diverse physiological systems. C1-INH is an inhibitor of proteases in the complement system, the contact system of kinin generation, and the intrinsic coagulation pathway. Cai, S. & Davis, A. E., Complement Regulatory Protein C1 Inhibitor Binds to Selectins and Interferes with Endothelial-Leukocyte Adhesion, *J Immunol,* 171:4786-4791 (2003). Specifically, C1-INH has been shown to inhibit C1r and C1s of the complement system. C1-INH is also a major regulator of coagulation factors XI and XII, as well as kallikrein and other serine proteases of the coagulation and fibrinolytic systems including tissue type plasminogen activator and plasmin.

Low plasma content of C1-INH or its dysfunction results in the activation of both complement and contact plasma cascades, and may affect other systems as well. A decrease in C1-INH plasma content to levels lower than 55 μg/mL (~25% of normal) has been shown to induce spontaneous activation of C1.

A schematic depicting the structure of C1-INH is provided in FIG. 1. The signal peptide, N-terminal domain, and serpin domain are shown. The 22 amino acid signal peptide is required for secretion and cleaved from the rest of the C1-INH protein. C1-INH has two domains: a C-terminal domain having 365 amino acids, which is a typical serpin domain, and an N-terminal domain having 113 amino acids. The protein is stabilized by two disulfide bridges which connect the domains. These disulfide bridges are formed by Cys101 of the N-terminal domain which forms a disulfide bond with Cys406 of the C-terminal (serpin) domain and Cys108 of the N-terminal domain which forms a disulfide bond with Cys183 of C-terminal domain. The serpin domain is responsible for the protease activity of C1-INH. P1-P1' denotes the Arg444-Thr445 scissile bond.

More than 26% of the weight of the glycosylated protein is carbohydrate. The glycans are unevenly distributed over human C1-INH. The N-terminus is heavily glycosylated, having three N-linked (shown as long vertical lines with diamond heads) and at least seven O-linked (shown as short vertical lines) carbohydrate groups. Three N-attached glycans are attached to asparagine residues Asn216, Asn231, and Asn330 in the serpin domain (shown as long vertical lines with diamond heads). Although the functional role of the exceptionally long and heavily glycosylated N-terminal domain is still unclear, it may be essential for the protein's conformational stability, recognition, affinity to endotoxins and selectins, and clearance. The intrinsic heterogeneity of the carbohydrate moiety greatly contributes to the heterogeneity of the whole C1-INH, one of the reasons why production of an rhC1-INH mimicking the properties of plasma-derived C1-INH is difficult.

As used herein, rhC1-INH proteins suitable for the present invention comprise any wild-type and modified human C1-INH polypeptides (e.g., C1-INH proteins with amino acid mutations, deletions, truncations, and/or insertions) that retain substantial C1-INH biological activity. Typically, rhC1-INH protein is produced using recombinant technology.

Typically, a suitable rhC1-INH protein has an in vivo half-life of or greater than about 12 hours, 18 hours, 24 hours, 36 hours, 2 days, 2.5 days, 3 days, 3.5 days, 4 days, 4.5 days, 5 days, 5.5 days, 6 days, 6.5 days, 7 days, 7.5 days, 8 days, 8.5 days, 9 days, 9.5 days, or 10 days. In some embodiments, an rhC1-INH protein has an in vivo half-life of between 0.5 and 10 days, between 1 day and 10 days, between 1 day and 9 days, between 1 day and 8 days, between 1 day and 7 days, between 1 day and 6 days, between 1 day and 5 days, between 1 day and 4 days, between 1 day and 3 days, between 2 days and 10 days, between 2 days and 9 days, between 2 days and 8 days, between 2 days and 7 days, between 2 days and 6 days, between 2 days and 5 days, between 2 days and 4 days, between 2 day and 3 days, between 2.5 days and 10 days, between 2.5 days and 9 days, between 2.5 days and 8 days, between 2.5 days and 7 days, between 2.5 days and 6 days, between 2.5 days and 5 days, between 2.5 days and 4 days, between 3 days and 10 days, between 3 days and 9 days, between 3 days and 8 days, between 3 days and 7 days, between 3 days and 6 days, between 3 days and 5 days, between 3 days and 4 days, between 3.5 days and 10 days, between 3.5 days and 9 days, between 3.5 days and 8 days, between 3.5 days and 7 days, between 3.5 days and 6 days, between 3.5 days and 5 days, between 3.5 days and 4 days, between 4 days and 10 days, between 4 days and 9 days, between 4 days and 8 days, between 4 days and 7 days, between 4 days and 6 days, between 4 days and 5 days, between 4.5 days and 10 days, between 4.5 days and 9 days, between 4.5 days and 8 days, between 4.5 days and 7 days, between 4.5 days and 6 days, between 4.5 days and 5 days, between 5 days and 10 days, between 5 days and 9 days, between 5 days and 8 days, between 5 days and 7 days, between 5 days and 6 days, between 5.5 days and 10 days, between 5.5 days and 9 days, between 5.5 days and 8 days, between 5.5 days and 7 days, between 5.5 days and 6 days, between 6 days and 10 days, between 7 days and 10 days, between 8 days and 10 days, between 9 days and 10 days.

In some embodiments, the purified recombinant rhC1-INH has a half-life similar to or longer than the half-life of plasma-derived human C1 esterase inhibitor. In some embodiments, the purified recombinant rhC1-INH has a half-life comparable to or longer than the half-life of plasma-derived human C1 esterase inhibitor. In some embodiments, the purified recombinant rhC1-INH has a half-life equivalent to or longer than the half-life of plasma-derived human C1 esterase inhibitor. In some embodiments, the purified recombinant rhC1-INH has a half-life bioequivalent to or longer than the half-life of plasma-derived human C1 esterase inhibitor. In some embodiments, the purified recombinant rhC1-INH has a half-life the same as the half-life of plasma-derived human C1 esterase inhibitor. In some embodiments, the purified recombinant rhC1-INH has a half-life in the range of 50%-150% of the half-life of plasma-derived human C1 esterase inhibitor. In some embodiments, the purified recombinant rhC1-INH has a half-life in the range of 60%-130% of the half-life of plasma-derived human C1 esterase inhibitor. In some embodiments, the purified recombinant rhC1-INH has a half-life in the range of 70%-130% of the half-life of plasma-derived human C1 esterase inhibitor. In some embodiments, the purified recombinant rhC1-INH has a half-life in the range of 80%-120% of the half-life of plasma-derived human C1 esterase inhibitor. In some embodiments, the purified recombinant rhC1-INH has a half-life in the range of 80%-130% of the half-life of plasma-derived human C1 esterase inhibitor. In some embodiments, the purified recombinant rhC1-INH has a half-life in the range of 80%-140% of the half-life of plasma-derived human C1 esterase inhibitor. In some embodiments, the purified recombinant rhC1-INH has a half-life in the range of 80%-150% of the half-life of plasma-derived human C1 esterase inhibitor.

In some embodiments, an rhC1-INH polypeptide suitable for the present invention includes an amino acid sequence at least 50% (e.g., at least 55%, 60%, 65%, 70%, 75%, 80%, 85%, 90%, 95%, 96%, 97%, 98%, 99%, or 100%) identical to the wild-type human C1-INH protein (amino acids 1-478) (amino acids 1-97 are underlined):

(SEQ ID NO: 1)
<u>NPNATSSSSQDPESLQDRGEGKVATTVISKMLFVEPILEVSSLPTTNST</u>

<u>TNSATKITANTTDEPTTQPTTEPTTQPTIQPTQPTTQLPTDSPTQPTTG</u>

SFCPGPVTLCSDLESHSTEAVLGDALVDFSLKLYHAFSAMKKVETNMAF

SPFSIASLLTQVLLGAGENTKTNLESILSYPKDFTCVHQALKGFTTKGV

TSVSQIFHSPDLAIRDTFVNASRTLYSSSPRVLSNNSDANLELINTWVA

KNTNNKISRLLDSLPSDTRLVLLNAIYLSAKWKTTFDPKKTRMEPFHFK

NSVIKVPMMNSKKYPVAHFIDQTLKAKVGQLQLSHNLSLVILVPQNLKH

RLEDMEQALSPSVFKAIMEKLEMSKFQPTLLTLPRIKVTTSQDMLSIME

KLEFFDFSYDLNLCGLTEDPDLQVSAMQHQTVLELTETGVEAAAASAIS

VARTLLVFEVQQPFLFVLWDQQHKFPVFMGRVYDPRA.

In some embodiments, an rhC1-INH polypeptide suitable for the present invention includes an amino acid sequence at least 50% (e.g., at least 55%, 60%, 65%, 70%, 75%, 80%, 85%, 90%, 95%, 96%, 97%, 98%, 99%, or 100%) identical to a human C1-INH protein (amino acids 1-478) having an E165Q mutation (mutated amino acid bolded and underlined):

(SEQ ID NO: 2)
NPNATSSSSQDPESLQDRGEGKVATTVISKMLFVEPILEVSSLPTTNST

TNSATKITANTTDEPTTQPTTEPTTQPTIQPTQPTTQLPTDSPTQPTTG

SFCPGPVTLCSDLESHSTEAVLGDALVDFSLKLYHAFSAMKKVETNMAF

SPFSIASLLTQVLLGAG<u>E</u>NTKTNLESILSYPKDFTCVHQALKGFTTKGV

TSVSQIFHSPDLAIRDTFVNASRTLYSSSPRVLSNNSDANLELINTWVA

KNTNNKISRLLDSLPSDTRLVLLNAIYLSAKWKTTFDPKKTRMEPFHFK

NSVIKVPMMNSKKYPVAHFIDQTLKAKVGQLQLSHNLSLVILVPQNLKH

RLEDMEQALSPSVFKAIMEKLEMSKFQPTLLTLPRIKVTTSQDMLSIME

KLEFFDFSYDLNLCGLTEDPDLQVSAMQHQTVLELTETGVEAAAASAIS

VARTLLVFEVQQPFLFVLWDQQHKFPVFMGRVYDPRA.

In some embodiments, an rhC1-INH polypeptide suitable for the present invention includes an amino acid sequence at least 50% (e.g., at least 55%, 60%, 65%, 70%, 75%, 80%, 85%, 90%, 95%, 96%, 97%, 98%, 99%, or 100%) identical to the truncated wild-type human C1-INH protein (amino acids 98-478):

(SEQ ID NO: 3)
GSFCPGPVTLCSDLESHSTEAVLGDALVDFSLKLYHAFSAMKKVETNMA

FSPFSIASLLTQVLLGAGENTKTNLESILSYPKDFTCVHQALKGFTTKG

VTSVSQIFHSPDLAIRDTFVNASRTLYSSSPRVLSNNSDANLELINTWV

AKNTNNKISRLLDSLPSDTRLVLLNAIYLSAKWKTTFDPKKTRMEPFHF

KNSVIKVPMMNSKKYPVAHFIDQTLKAKVGQLQLSHNLSLVILVPQNLK

HRLEDMEQALSPSVFKAIMEKLEMSKFQPTLLTLPRIKVTTSQDMLSIM

EKLEFFDFSYDLNLCGLTEDPDLQVSAMQHQTVLELTETGVEAAAASAI

SVARTLLVFEVQQPFLFVLWDQQHKFPVFMGRVYDPRA.

In some embodiments, an rhC1-INH polypeptide suitable for the present invention includes an amino acid sequence at least 50% (e.g., at least 55%, 60%, 65%, 70%, 75%, 80%, 85%, 90%, 95%, 96%, 97%, 98%, 99%, or 100%) identical to the truncated wild-type human C1-INH protein (amino acids 98-478) having an E165Q mutation (mutated amino acid bolded and underlined):

(SEQ ID NO: 4)
GSFCPGPVTLCSDLESHSTEAVLGDALVDFSLKLYHAFSAMKKVETNMA

FSPFSIASLLTQVLLGAG<u>E</u>NTKTNLESILSYPKDFTCVHQALKGFTTKG

VTSVSQIFHSPDLAIRDTFVNASRTLYSSSPRVLSNNSDANLELINTWV

AKNTNNKISRLLDSLPSDTRLVLLNAIYLSAKWKTTFDPKKTRMEPFHF

KNSVIKVPMMNSKKYPVAHFIDQTLKAKVGQLQLSHNLSLVILVPQNLK

HRLEDMEQALSPSVFKAIMEKLEMSKFQPTLLTLPRIKVTTSQDMLSIM

EKLEFFDFSYDLNLCGLTEDPDLQVSAMQHQTVLELTETGVEAAAASAI

SVARTLLVFEVQQPFLFVLWDQQHKFPVFMGRVYDPRA.

As disclosed herein, SEQ ID NO:1 represents the canonical amino acid sequence for the human C1-INH protein. In some embodiments, a C1-INH polypeptide may be a truncated C1-INH such as SEQ ID NO:3 or SEQ ID NO:4. In some embodiments, a suitable rhC1-INH polypeptide may be a homologue or an analogue of a wild-type or naturally-occurring protein. For example, a homologue or an analogue of human wild-type or naturally-occurring C1-INH polypeptide may contain one or more amino acid or domain substitutions, deletions, and/or insertions as compared to a wild-type or naturally-occurring C1-INH protein (e.g., SEQ ID NO:1), while retaining substantial C1-INH protein activity (e.g., SEQ ID NO:2). Thus, in some embodiments, an rhC1-INH polypeptide suitable for the present invention is substantially homologous to wild-type human C1-INH protein (SEQ ID NO:1).

In some embodiments, an rhC1-INH polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, an rhC1-INH polypeptide suitable for the present invention is substantially identical to wild-type human C1-INH protein (SEQ ID NO:1). In some embodiments, an rhC1-INH polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1.

In some embodiments, a recombinant human C1-INH polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:2. In some embodiments, an rhC1-INH polypeptide suitable for the present invention is substantially identical to a human C1-INH protein of SEQ ID NO:2. In some embodiments, an rhC1-INH polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:2.

Homologues or analogues of human C1-INH proteins can be prepared according to methods for altering polypeptide sequence known to one of ordinary skill in the art such as are found in references that compile such methods. In some embodiments, conservative substitutions of amino acids include substitutions made among amino acids within the following groups: (a) M, I, L, V; (b) F, Y, W; (c) K, R, H; (d) A, G; (e) S, T; (f) Q, N; and (g) E, D. In some embodiments, a "conservative amino acid substitution" refers to an amino acid substitution that does not alter the relative charge or size characteristics of the protein in which the amino acid substitution is made.

In some embodiments, an rhC1-INH polypeptide suitable for the present invention contains one or more amino acid deletions, insertions or replacement as compared to a wild-type human C1-INH protein of SEQ ID NO:1 or a C1-INH protein of SEQ ID NO:2. For example, a suitable rhC1-INH polypeptide may be truncated, such as the polypeptide of SEQ ID NO:3 or SEQ ID NO:4.

In some embodiments, a C1-INH polypeptide may be a truncated C1-INH while retaining substantial C1-INH protein activity, such as SEQ ID NO:3 or SEQ ID NO:4. Thus, in some embodiments, an rhC1-INH polypeptide suitable for the present invention is substantially homologous to SEQ ID NO:3 or SEQ ID NO:4. In some embodiments, an rhC1-INH polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:3 or SEQ ID NO:4. In some embodiments, an rhC1-INH polypeptide suitable for the present invention is substantially identical to SEQ ID NO:3 or SEQ ID NO:4. In some embodiments, an rhC1-INH polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:3 or SEQ ID NO:4.

An rhC1-INH protein suitable for the present invention exhibits the therapeutic effect of C1-INH by, for example, enhancing or increasing half-life, stability, potency, and/or delivery of rhC1-INH protein, or reducing or eliminating immunogenicity, clearance, or toxicity. In some embodiments, the rhC1-INH protein has a half-life similar to or longer than plasma-derived C1-INH. In some embodiments, the rhC1-INH protein has activity similar to or greater than plasma-derived C1-INH.

Exemplary Recombinant C1-INH Proteins

In particular embodiments, a suitable rhC1-INH protein comprises an amino acid sequence at least 50%, 55%, 60%, 65%, 70%, 75%, 80%, 85%, 90%, 91%, 92%, 93%, 94%, 95%, 96%, 97%, 98%, 99% or 100% identical to the wild-type human C1-INH polypeptide of SEQ ID NO:1, or a C1-INH polypeptide of SEQ ID NO:2, or a truncated C1-INH polypeptide of SEQ ID NO:3 or SEQ ID NO:4. In some embodiments, a suitable rhC1-INH protein has an in vivo half-life ranging from about 0.5-10 days (e.g., about 0.5-5.5 days, about 0.5-5 days, about 1-5 days, about 1.5-5 days, about 1.5-4.5 days, about 1.5-4.0 days, about 1.5-3.5 days, about 1.5-3 days, about 1.5-2.5 days, about 2-6 days, about 2-5.5 days, about 2-5 days, about 2-4.5 days, about 2-4 days, about 2-3.5 days, about 2-3 days). In some embodiments, a suitable rhC1-INH protein has an in vivo half-life ranging from about 2-10 days (e.g., ranging from about 2.5-10 days, from about 3-10 days, from about 3.5-10 days, from about 4-10 days, from about 4.5-10 days, from about 5-10 days, from about 3-8 days, from about 3.5-8 days, from about 4-8 days, from about 4.5-8 days, from about 5-8 days, from about 3-6 days, from about 3.5-6 days, from about 4-6 days, from about 4.5-6 days, from about 5-6 days).

In some embodiments, a suitable rhC1-INH protein has an amino acid sequence at least 50%, 55%, 60%, 65%, 70%, 75%, 80%, 85%, 90%, 91%, 92%, 93%, 94%, 95%, 96%, 97%, 98%, 99% or more homologous or identical to SEQ ID NO:1, SEQ ID NO:2, SEQ ID NO:3, or SEQ ID NO:4.

An rhC1-INH protein suitable for the present invention is stable for extended periods of time at various concentrations. In some embodiments, the purified recombinant rhC1-INH protein is stable as a liquid product at concentrations exceeding about 20 mg/mL, 30 mg/mL, 40 mg/mL, 50 mg/mL, 60 mg/mL. 70 mg/mL, 80 mg/mL, 90 mg/mL, 100 mg/mL or more.

Glycosylation/Glycan Mapping (Profile)

The rhC1-INH protein or polypeptide produced according to the present invention has distinct characteristics such as sialic acid content and glycan map. In some embodiments, the recombinantly expressed C1-INH protein or polypeptide has a glycosylation profile similar to that of plasma-derived C1-INH. In some embodiments, the recombinantly expressed C1-INH protein or polypeptide has a glycosylation profile such that the recombinantly expressed C1-INH protein exhibits a half-life similar to that of plasma-derived C1-INH. In some embodiments, the recombinantly expressed C1-INH protein or polypeptide has a glycosylation profile such that the recombinantly expressed C1-INH protein exhibits a half-life greater than that of plasma-derived C1-INH.

In some embodiments, a purified rhC1-INH protein may be characterized by their proteoglycan composition, typically referred to as glycan mapping. Without wishing to be bound by any theory, it is thought that glycan linkage along with the shape and complexity of the branch structure may impact in vivo clearance, bioavailability, and/or efficacy.

Typically, a glycan map may be determined by enzymatic digestion and subsequent chromatographic analysis. Various enzymes may be used for enzymatic digestion including, but not limited to, suitable glycosylases, peptidases (e.g., Endopeptidases, Exopeptidases), proteases, and phosphatases. In some embodiments, a suitable enzyme is alkaline phosphatase. In some embodiments, a suitable enzyme is neuraminidase. Glycans may be detected by chromatographic analysis. For example, glycans may be detected by High Performance Anion Exchange Chromatography with Pulsed Amperometric Detection (HPAE-PAD) or size exclusion High Performance Liquid Chromatography (HPLC). The quantity of glycan represented by each peak on a glycan map may be calculated using a standard curve of glycan according to methods known in the art and disclosed herein.

In some embodiments, a purified C1-INH according to the present invention is characterized with a glycan map. The relative amount of glycan corresponding to each peak group may be determined based on the peak group area relative to the corresponding peak group area in a predetermined reference standard. Various reference standards for glycan mapping are known in the art and can be used to practice the present invention. In some embodiments, the purified rhC1-INH is characterized with a glycan map comprising five or fewer peak groups selected from the peak groups indicative of neutral, mono-sialylated, di-sialylated, tri-sialylated, or tetra-sialylated rhC1-INH protein.

In some embodiments, the purified rhC1-INH has a glycosylation profile comprising at least one of the following: neutral glycan species, mono-sialylated species, di-sialylated species, tri-sialylated species and/or tetra-sialylated species. In some embodiments, the purified rhC1-INH has a glycosylation profile comprising neutral glycan species, mono-sialylated species, di-sialylated species, tri-sialylated species and tetra-sialylated species. In some embodiments, purified recombinant rhC1-INH has a glycosylation profile comprising between about 10% and about 20% neutral glycan species. In some embodiments, the purified recombinant rhC1-INH has a glycosylation profile comprising no more than about 50%, 45%, 40%, 35%, 30%, 25%, 20%, 15%, 10%, or 5% neutral glycan species. In some embodiments, purified recombinant rhC1-INH has a glycosylation profile comprising between about 5% and about 30% neutral glycan species. In some embodiments, purified recombinant rhC1-INH has a glycosylation profile comprising between about 5% and about 25% neutral glycan species. In some embodiments, purified recombinant rhC1-INH has a glycosylation profile comprising between about 10% and about 30% mono-sialylated species. In some embodiments, purified recombinant rhC1-INH has a glycosylation profile comprising between about 30% and about 50% di-sialylated species. In some embodiments, purified recombinant rhC1-INH has a glycosylation profile comprising between about 15% and about 35% tri-sialylated species. In some embodiments, purified recombinant rhC1-INH has a glycosylation profile comprising between about 5% and about 15% tetra-sialylated species. In some embodiments, rhC1-INH protein comprises, on average, at least about 80% charged glycans per molecule (e.g., greater than about 85%, 90%, 95% or 99% glycans per molecule). In some embodiments, the purified recombinant rhC1-INH has a glycosylation profile comprising no more than about 30% neutral glycan species and a sialylated glycan species such that the purified rhC1-INH has a half-life similar to or longer than plasma derived C1-INH. In some embodiments, the purified recombinant rhC1-INH has a glycosylation profile comprising no more than 30% neutral glycan species, between about 20% and about 30% mono-sialylated glycan species, between about 30% and about 40% di-sialylated glycan species, between about 10% and about 20% tri-sialylated glycan species, and between about 5% and about 10% tetra-sialylated glycan species.

In some embodiments, the purified recombinant rhC1-INH contains less than about 20%, 15%, 10%, 5%, or 0% of one or more of mannose, α-galactose, N-glycolylneuraminic acid (NGNA), and/or oligomannose-type glycosylation. In some embodiments, the purified recombinant rhC1-INH contains no more than about 20%, 15%, 10%, 5%, or 0% of one or more of mannose, α-galactose, N-glycolylneuraminic acid (NGNA), and/or oligomannose-type glycosylation. In some embodiments, the purified recombinant rhC1-INH has a glycosylation profile that is not immunogenic. In some embodiments, the purified recombinant rhC1-INH has a glycosylation profile that does not increase serum clearance rate when compared with plasma-derived human C1-INH. In some embodiments, the purified recombinant rhC1-INH has a glycosylation profile that decreases serum clearance rate when compared with plasma-derived human C1-INH. In some embodiments, the purified recombinant rhC1-INH has a glycosylation profile that decreases serum clearance rate when compared with conestat alfa.

In some embodiments, cells engineered to express rhC1-INH can also be engineered to increase sialylation of the expressed rhC1-INH. In some embodiments, the cells are engineered to express a heterologous enzyme to increase sialylation. In some embodiments, the cells are engineered to express a mutant heterologous enzyme to increase sialylation. In some embodiments, the cells are engineered to overexpress an endogenous enzyme to increase sialylation. In some embodiments, the cells are engineered to express a mutated endogenous enzyme to increase sialylation. In some embodiments, the cells are engineered to reduce or prevent expression of endogenous enzymes that reduce, inhibit, or degrade sialylation (e.g., with an antisense construct).

Various methods of manipulating the glycosylation profile of proteins are known in the art. These methods as well as others yet to be discovered are contemplated by the instant invention. Methods of manipulating the glycosylation profile of C1-INH proteins and polypeptides of the invention include in vitro, in situ, and in vivo methods. In some embodiments the glycosylation profile of expressed proteins or polypeptides is altered through post-expression chemical modification of the expressed protein or polypeptide. In some embodiments the cell culture conditions are manipulated to achieve expression of proteins having a desired glycosylation profile. These cell culture conditions include control of the production and culture process including length of culture, additives to culture medium, and/or co-expression of genes to enhance glycosylation. Selection of host cells and specific clones of transfected host cells may also be used to enhance glycosylation. Some methods of enhancing glycosylation include purification processes to enrich for proteins or polypeptides having the desired glycosylation profile.

The half-life of C1-INH may be affected by the glycosylation profile. For example, Ruconest® (Pharming N.V.), a recombinant C1-INH polypeptide that is less sialylated and/or has a different sialylation distribution from plasma-derived human C1-INH has been shown to have a dramatically shorter half-life than plasma-derived human C1-INH. See, e.g., Davis, B. & Bernstein, J. A., Conestat alfa for the treatment of angioedema attacks, *Ther Clin Risk Manag.* 7: 265-273 (2011); Koles, K. et al., Influence of lactation parameters on the N-glycosylation of recombinant human C1 esterase inhibitor isolated from the milk of transgenic rabbits, *Glycobiology*, 14(11):979-986 (2004); Koles, K. et al., N- and O-glycans of recombinant human C1 esterase inhibitor expressed in the milk of transgenic rabbits, *Glycobiology*, 14(1):51-64 (2004). Although Ruconest® has the same amino acid sequence as human plasma derived C1-INH, since it is made in rabbits, its glycosylation profile is very different from that of human plasma-derived C1-INH. The result is that Ruconest® has an extremely short half-life of about 2.4-2.7 hours. See Ruconest® FDA Label and Prescribing Information. In contrast, human plasma-derived C1-INH has been shown to have a mean half-life in the range of about 56-62 hours. See Cinryze® Prescribing Information. As discussed herein, cells of the invention may be engineered to improve the glycosylation profile of the expressed rhC1-INH protein such that an rhC1-INH of the invention has a half-life similar to or longer than plasma-derived C1-INH.

Sialylation/Sialic Acid Content

In some embodiments, the recombinantly expressed C1-INH protein or polypeptide has a sialylation profile similar to that of plasma-derived C1-INH. In some embodiments, the recombinantly expressed C1-INH protein or polypeptide has a sialylation profile such that the recombinantly expressed C1-INH protein exhibits a half-life similar to that of plasma-derived C1-INH. In some embodiments, the recombinantly expressed C1-INH protein or polypeptide has a sialylation profile such that the recombinantly expressed C1-INH protein exhibits a half-life greater than that of plasma-derived C1-INH. In some embodiments, the purified recombinant human C1 esterase inhibitor (rhC1-INH or C1-INH) comprises on average, at least about 10, 11, 12, 13, or 14 sialylated glycan residues per molecule. In some embodiments, the purified recombinant human C1 esterase inhibitor (rhC1-INH or C1-INH) comprises on average, at least about 15, 16, 17, 18, 19, 20, 21, 22, 23, 24, 25, 26, 27, 28, or 29 sialylated glycan residues per molecule. In some embodiments, the purified recombinant human C1 esterase inhibitor (rhC1-INH or C1-INH) comprises on average, at least about 30, 31, 32, 33, 34, 35, 36, 37, 38, 39, or 40 sialylated glycan residues per molecule.

Various methods of manipulating the sialylation profile of proteins are known in the art. These methods as well as others yet to be discovered are contemplated by the instant invention. Methods of manipulating the sialylation profile of C1-INH proteins and polypeptides of the invention include in vitro, in situ, and in vivo methods. In some embodiments the sialylation profile of expressed proteins or polypeptides is altered through post-expression chemical modification of the expressed protein or polypeptide. In some embodiments the cell culture conditions are manipulated to achieve expression of proteins having a desired sialylation profile. These cell culture conditions include control of the production and culture process including length of culture, additives to culture medium, and/or co-expression of genes to enhance sialylation. Selection of host cells and specific clones of transfected host cells may also be used to enhance sialylation. Some methods of enhancing sialylation include purification processes to enrich for proteins or polypeptides having the desired sialylation profile.

Production of Recombinant C1-INH Proteins

An rhC1-INH protein suitable for the present invention may be produced by any available means. For example, an rhC1-INH protein may be recombinantly produced by utilizing a host cell system engineered to express an rhC1-INH protein-encoding nucleic acid. Alternatively or additionally, an rhC1-INH protein may be produced by activating endogenous genes. Alternatively or additionally, an rhC1-INH protein may be partially or fully prepared by chemical synthesis.

Where proteins are recombinantly produced, any expression system can be used. To give but a few examples, known expression systems include, for example, E. coli, egg, baculovirus, plant, yeast, or mammalian cells.

In some embodiments, rhC1-INH proteins suitable for the present invention are produced in mammalian cells. Non-limiting examples of mammalian cells that may be used in accordance with the present invention include BALB/c mouse myeloma line (NSO/1, ECACC No: 85110503); human retinoblasts (PER.C6, CruCell, Leiden, The Netherlands); monkey kidney CV1 line transformed by SV40 (COS-7, ATCC CRL 1651); human embryonic kidney line (HEK293 or 293 cells subcloned for growth in suspension culture, Graham et al., J. Gen Virol., 36:59, 1977); human fibrosarcoma cell line (e.g., HT1080); baby hamster kidney cells (BHK21, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

In some embodiments, the present invention provides rhC1-INH proteins produced from human cells. In some embodiments, the present invention provides rhC1-INH proteins produced from CHO cells, HT1080 cells or HEK cells.

Typically, cells that are engineered to express an rhC1-INH protein may comprise a transgene that encodes an rhC1-INH protein described herein. It should be appreciated that the nucleic acids encoding rhC1-INH protein may contain regulatory sequences, gene control sequences, promoters, non-coding sequences and/or other appropriate sequences for expressing the rhC1-INH protein. Typically, the coding region is operably linked with one or more of these nucleic acid components.

The coding region of a transgene may include one or more silent mutations to optimize codon usage for a particular cell type. For example, the codons of a C1-INH transgene may be optimized for expression in a vertebrate cell. In some embodiments, the codons of a C1-INH transgene may be optimized for expression in a mammalian cell. In some embodiments, the codons of a C1-INH transgene may be optimized for expression in a human cell. In some embodiments, the codons of a C1-INH transgene may be optimized for expression in a CHO cell.

Nucleic Acids Encoding Recombinant C1-Inhibitor Proteins

In some embodiments, nucleic acid molecules are provided comprising nucleic acid sequences encoding for a recombinant gene of interest (herein referred to as a transgene) such as a C1-inhibitor protein described in various embodiments herein. In some embodiments, the nucleic acid encoding a transgene may be modified to provide increased expression of the encoded C1-inhibitor protein, which is also referred to as codon optimization. For example, the nucleic acid encoding a transgene can be modified by altering the open reading frame for the coding sequence. As used herein, the term "open reading frame" is synonymous with "ORF" and means any nucleotide sequence that is potentially able to encode a protein, or a portion of a protein. An open reading frame usually begins with a start codon (represented as, e.g. AUG for an RNA molecule and ATG in a DNA molecule in the standard code) and is read in codon-triplets until the frame ends with a STOP codon (represented as, e.g. UAA, UGA or UAG for an RNA molecule and TAA, TGA or TAG in a DNA molecule in the standard code). As used herein, the term "codon" means a sequence of three nucleotides in a nucleic acid molecule that specifies a particular amino acid during protein synthesis; also called a triplet or codon-triplet. For example, of the 64 possible codons in the standard genetic code, two codons, GAA and GAG encode the amino acid Glutamine whereas the codons AAA and AAG specify the amino acid Lysine. In the standard genetic code three codons are stop codons, which do not specify an amino acid. As used herein, the term "synonymous codon" means any and all of the codons that code for a single amino acid. Except for Methionine and Tryptophan, amino acids are coded by two to six synonymous codons. For example, in the standard genetic code the four synonymous codons that code for the amino acid Alanine are GCA, GCC, GCG and GCU, the two synonymous codons that specify Glutamine are GAA and GAG and the two synonymous codons that encode Lysine are AAA and AAG.

In some embodiments, a nucleic acid encoding the open reading frame of a C1-inhibitor protein may be modified using standard codon optimization methods. Various commercial algorithms for codon optimization are available and can be used to practice the present invention. Typically, codon optimization does not alter the encoded amino acid sequences. In some embodiments, codon optimization may lead to amino acids alteration such as substitution, deletion or insertion. Typically, such amino acid alteration does not substantially alter the protein activity.

Exemplary nucleic acid sequences encode for C1-inhibitor proteins having an amino acid sequence at least 50%, 55%, 60%, 65%, 70%, 75%, 80%, 85%, 90%, 91%, 92%, 93%, 94%, 95%, 96%, 97%, 98%, 99% or more identical or homologous to SEQ ID NO:1, SEQ ID NO:2, SEQ ID NO:3, or SEQ ID NO:4.

In some embodiments, a nucleotide change may alter a synonymous codon within the open reading frame in order to agree with the endogenous codon usage found in a particular heterologous cell selected to express C1-inhibitor protein. Alternatively or additionally, a nucleotide change may alter the G+C content within the open reading frame to better match the average G+C content of open reading frames found in endogenous nucleic acid sequence present in the heterologous host cell. A nucleotide change may also alter a polymononucleotide region or an internal regulatory or structural site found within a C1-inhibitor protein sequence. Thus, a variety of modified or optimized nucleotide sequences are envisioned including, without limitation, nucleic acid sequences providing increased expression of C1-inhibitor proteins in a prokaryotic cell; yeast cell; insect cell; and in a mammalian cell.

Typically, a modified nucleic acid encodes a C1-inhibitor protein with or without amino acid sequence alteration. In the event there is amino acid alteration, such alteration typically does not substantially decrease the C1-inhibitor protein activity. In some embodiments, such alteration increases and/or enhances the C1-inhibitor protein activity. Activity may refer to the following non-limiting list of parameters: increased half-life, increased/elevated protein expression by host cells, increased stability of expressed protein, increased solubility of expressed protein, decreased aggregation of expressed protein, simpler formulation of expressed protein, simpler purification of expressed protein, increased tolerance of expressed protein to changes in pH, increased ability of protein to tolerate high and low pH conditions, expressed protein that is suitable for formulating at high concentrations.

Expression Vectors

A nucleic acid sequence encoding a C1-inhibitor protein as described in the present application, can be molecularly cloned (inserted) into a suitable vector for propagation or expression in a host cell. A wide variety of expression vectors can be used to practice the present invention, including, without limitation, a prokaryotic expression vector; a yeast expression vector; an insect expression vector and a mammalian expression vector. Exemplary vectors suitable for the present invention include, but are not limited to, viral based vectors (e.g., AAV based vectors, retrovirus based vectors, plasmid based vectors). In some embodiments, a nucleic acid sequence encoding a C1-inhibitor protein can be inserted into a suitable vector. Typically, a nucleic acid encoding a C1-inhibitor protein is operably linked to various regulatory sequences or elements.

Regulatory Sequences or Elements

Various regulatory sequences or elements may be incorporated in an expression vector suitable for the present invention. Exemplary regulatory sequences or elements include, but are not limited to, promoters, enhancers, repressors or suppressors, 5' untranslated (or non-coding) sequences, introns, 3' untranslated (or non-coding) sequences.

As used herein, a "Promoter" or "Promoter sequence" is a DNA regulatory region capable of binding an RNA polymerase in a cell (e.g., directly or through other promoter bound proteins or substances) and initiating transcription of a coding sequence. A promoter sequence is, in general, bound at its 3' terminus by the transcription initiation site and extends upstream (5' direction) to include the minimum number of bases or elements necessary to initiate transcription at any level. The promoter may be operably associated with or operably linked to the expression control sequences, including enhancer and repressor sequences or with a nucleic acid to be expressed. In some embodiments, the promoter may be inducible. In some embodiments, the inducible promoter may be unidirectional or bi-directional. In some embodiments, the promoter may be a constitutive promoter. In some embodiments, the promoter can be a hybrid promoter, in which the sequence containing the transcriptional regulatory region is obtained from one source and the sequence containing the transcription initiation region is obtained from a second source. Systems for linking control elements to coding sequence within a transgene are well known in the art (general molecular biological and recombinant DNA techniques are described in Sambrook, Fritsch, and Maniatis, *Molecular Cloning: A Laboratory Manual*, Second Edition, Cold Spring Harbor Laboratory Press, Cold Spring Harbor, NY, 1989, which is incorporated herein by reference). Commercial vectors suitable for inserting a transgene for expression in various host cells under a variety of growth and induction conditions are also well known in the art.

In some embodiments, a specific promoter may be used to control expression of the transgene in a mammalian host cell such as, but are not limited to, SRα-promoter (see Takebe et al., *Molec. and Cell. Bio.* 8:466-472 (1988)), the human CMV immediate early promoter (Boshart et al., *Cell* 41:521-530 (1985); Foecking et al., *Gene* 45:101-105 (1986)), human CMV promoter, the human CMV5 promoter, the murine CMV immediate early promoter, the EF1-α-promoter, a hybrid CMV promoter for liver specific expression (e.g., made by conjugating CMV immediate early promoter with the transcriptional promoter elements of either human α-1-antitrypsin (HAT) or albumin (HAL) promoter), or promoters for hepatoma specific expression (e.g., wherein the transcriptional promoter elements of either human albumin (HAL; about 1000 bp) or human α-1-antitrypsin (HAT, about 2000 bp) are combined with a 145 long enhancer element of human α-1-microglobulin and bikunin precursor gene (AMBP); HAL-AMBP and HAT-AMBP; the SV40 early promoter region (see Benoist at al., *Nature* 290:304-310 (1981)), the *Orgyia pseudotsugata* immediate early promoter, the herpes thymidine kinase promoter (see Wagner at al., *Proc. Natl. Acad. Sci. USA* 78:1441-1445 (1981)); or the regulatory sequences of the metallothionein gene (see Brinster et al., *Nature* 296:39-42 (1982)). In some embodiments, the mammalian promoter is a constitutive promoter such as, but not limited to, the hypoxanthine phosphoribosyl transferase (HPTR) promoter, the adenosine deaminase promoter, the pyruvate kinase promoter, the beta-actin promoter as well as other constitutive promoters known to those of ordinary skill in the art.

In some embodiments, a specific promoter may be used to control expression of a transgene in a prokaryotic host cell such as, but are not limited to, the β-lactamase promoter (see Villa-Komaroff et al., *Proc. Natl. Acad. Sci. USA* 75:3727-3731 (1978)); the tac promoter (see DeBoer et al., *Proc. Natl. Acad. Sci. USA* 80:21-25 (1983)); the T7 promoter, the T3 promoter, the M13 promoter or the M16 promoter; in a yeast host cell such as, but are not limited to, the GAL1, GAL4 or GAL10 promoter, the ADH (alcohol dehydrogenase) promoter, PGK (phosphoglycerol kinase) promoter, alkaline phosphatase promoter, glyceraldehyde-3-phosphate dehydrogenase III (TDH3) promoter, glyceraldehyde-3-phosphate dehydrogenase II (TDH2) promoter, glyceraldehyde-3-phosphate dehydrogenase I (TDH1) promoter, pyruvate kinase (PYK), enolase (ENO), or triose phosphate isomerase (TPI).

In some embodiments, the promoter may be a viral promoter, many of which are able to regulate expression of a transgene in several host cell types, including mammalian cells. Viral promoters that have been shown to drive constitutive expression of coding sequences in eukaryotic cells include, for example, simian virus promoters, herpes simplex virus promoters, papilloma virus promoters, adenovirus promoters, human immunodeficiency virus (HIV) promoters, Rous sarcoma virus promoters, cytomegalovirus (CMV) promoters, the long terminal repeats (LTRs) of Moloney murine leukemia virus and other retroviruses, the thymidine kinase promoter of herpes simplex virus as well as other viral promoters known to those of ordinary skill in the art.

In some embodiments, the gene control elements of an expression vector may also include 5' non-transcribing and 5' non-translating sequences involved with the initiation of transcription and translation, respectively, such as a TATA box, capping sequence, CAAT sequence, Kozak sequence and the like. Enhancer elements can optionally be used to increase expression levels of a polypeptide or protein to be expressed. Examples of enhancer elements that have been shown to function in mammalian cells include the SV40 early gene enhancer, as described in Dijkema et al., EMBO J. (1985) 4: 761 and the enhancer/promoter derived from the long terminal repeat (LTR) of the Rous Sarcoma Virus (RSV), as described in Gorman et al., Proc. Natl. Acad. Sci. USA (1982b) 79:6777 and human cytomegalovirus, as described in Boshart et al., Cell (1985) 41:521. Genetic control elements of an expression vector will also include 3' non-transcribing and 3' non-translating sequences involved with the termination of transcription and translation. Respectively, such as a poly polyadenylation (polyA) signal for stabilization and processing of the 3' end of an mRNA transcribed from the promoter. Poly A signals included, for example, the rabbit beta globin polyA signal, bovine growth hormone polyA signal, chicken beta globin terminator/polyA signal, or SV40 late polyA region.

Selectable Markers

Expression vectors will preferably but optionally include at least one selectable marker. In some embodiments, the selectable maker is a nucleic acid sequence encoding a resistance gene operably linked to one or more genetic regulatory elements, to bestow upon the host cell the ability to maintain viability when grown in the presence of a cytotoxic chemical and/or drug. In some embodiments, a selectable agent may be used to maintain retention of the expression vector within the host cell. In some embodiments, the selectable agent may be used to prevent modification (i.e. methylation) and/or silencing of the transgene sequence within the expression vector. In some embodiments, a selectable agent is used to maintain episomal expression of the vector within the host cell. In some embodiments, the selectable agent is used to promote stable integration of the transgene sequence into the host cell genome. In some embodiments, an agent and/or resistance gene may include, but is not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), zeomycin, mycophenolic acid, or glutamine synthetase (GS, U.S. Pat. Nos. 5,122,464; 5,770,359; 5,827,739) for eukaryotic host cell; tetracycline, ampicillin, kanamycin, or chloramphenicol for a prokaryotic host cell; and URA3, LEU2, HIS3, LYS2, HIS4, ADE8, CUP1, or TRP1 for a yeast host cell.

Expression vectors may be transfected, transformed or transduced into a host cell. As used herein, the terms "transfection," "transformation" and "transduction" all refer to the introduction of an exogenous nucleic acid sequence into a host cell. In some embodiments, expression vectors containing nucleic acid sequences encoding for a C1-inhibitor protein are transfected, transformed or transduced into a host cell.

Examples of transformation, transfection and transduction methods, which are well known in the art, include liposome delivery, i.e., Lipofectamine™ (Gibco BRL) Method of Hawley-Nelson, *Focus* 15:73 (1193), electroporation, CaPO$_4$ delivery method of Graham and van der Erb, *Virology*, 52:456-457 (1978), DEAE-Dextran medicated delivery, microinjection, biolistic particle delivery, polybrene mediated delivery, cationic mediated lipid delivery, transduction, and viral infection, such as, e.g., retrovirus, lentivirus, adenovirus adeno-associated virus and Baculovirus (Insect cells). General aspects of cell host transformations have been described in the art, such as by Axel in U.S. Pat. No. 4,399,216; Sambrook, supra, Chapters 1-4 and 16-18; Ausubel, supra, chapters 1, 9, 13, 15, and 16. For various techniques for transforming mammalian cells, see Keown et al., *Methods in Enzymology* (1989), Keown et al., *Methods in Enzymology*, 185:527-537 (1990), and Mansour et al., *Nature*, 336:348-352 (1988).

Once introduced inside cells, expression vectors may be integrated stably in the genome or exist as extra-chromosomal constructs. Vectors may also be amplified and multiple copies may exist or be integrated in the genome. In some embodiments, cells of the invention may contain 1, 2, 3, 4, 5, 6, 7, 8, 9, 10, 15, 20 or more copies of nucleic acids encoding a C1-inhibitor protein. In some embodiments, cells of the invention may contain multiple copies (e.g., 2, 3, 4, 5, 6, 7, 8, 9, 10, 15, 20 or more) of nucleic acids encoding C1-inhibitor protein and one or more proteins which enhance glycosylation, preferably by increased sialylation, of the expressed C1-inhibitor protein. Sialylation can also be manipulated through the various methods described herein. Without wishing to be bound by any theory, decreased sialylation was found to be associated with increased heparin binding of the disclosed constructs, thereby preventing the C1-INH binding site from binding to targets. Heparin binding also increases likelihood of internalization into the lysosome, thereby increasing the rate of clearance.

Host Cells

As used herein, the term "host cells" refers to cells that can be used to produce recombinant C1-inhibitor protein. In particular, host cells are suitable for producing recombinant C1-inhibitor protein at a large scale. Suitable host cells can be derived from a variety of organisms, including, but not limited to, mammals, plants, birds (e.g., avian systems), insects, yeast, and bacteria. In some embodiments, host cells are mammalian cells. In some embodiments, a suitable host cell is engineered to improve the glycosylation profile of the expressed rhC1-INH protein. In some embodiments of the invention, the rhC1-INH polypeptide has a the same or similar glycosylation profile to the analogous portions of native plasma-derived C1-INH. In some embodiments, the C1-INH polypeptide has at least 50%, 55%, 60%, 65%, 70%, 75%, 80%, 85%, 90%, 91%, 92%, 93%, 94%, 95%, 96%, 97%, 98%, 99% glycans equivalent to native plasma-derived C1-INH. In some embodiments, the glycosylation profile of the rhC1-INH protein has a humanized glycosylation profile. In some embodiments, the rhC1-INH protein has increased sialylation compared to native plasma-derived C1-INH.

Improvement of the glycosylation profile may refer to increasing sialylation and/or humanizing the glycosylation profile, e.g., expressing in an engineered cell an rhC1-INH protein comprising a C1-INH polypeptide, thereby producing a glycosylation profile more similar to native human C1-INH than a C1-INH polypeptide expressed in a non-engineered cell. Improvement may also refer to increasing, enhancing, and/or optimizing the glycosylation profile of the C1-INH compared to Ruconest.

Various methods of changing, controlling, manipulating, improving, enhancing, and/or optimizing the glycosylation profile of proteins are known in the art. The glycosylation profile characteristics that may be optimized include the number of glycan residues, location of glycan residue attachment, manner of glycan attachment (e.g., type of bond), process of glycan attachment, and identity of glycan residues attached to the protein or polypeptide. The glycosylation profile of any portion of the proteins of the invention are contemplated as suitable targets for glycosylation optimization. These methods of controlling the glycosylation profile, as well as others yet to be discovered that a person of skill would understand as having utility in view of the instant disclosure in optimizing glycosylation of the proteins of the invention, are contemplated. Methods of changing, controlling, manipulating, improving, enhancing, and/or optimizing the glycosylation profile of C1-INH proteins and polypeptides of the invention include in vitro, in situ, and in vivo methods.

In some embodiments the glycosylation profile of expressed proteins or polypeptides is altered through post-translational and/or chemical modification of the expressed protein or polypeptide.

In some embodiments, the C1-INH protein that has undergone post-translational and/or chemical modification has a glycosylation profile that is changed, improved, enhanced, humanized, and/or optimized compared to a C1-INH protein having the same sequence that has not undergone said post-translational and/or chemical modification. In some embodiments, the C1-INH protein that has undergone post-translational and/or chemical modification has a sialylation profile that is changed, improved, enhanced, humanized, and/or optimized compared to a C1-INH protein having the same sequence that has not undergone said post-translational and/or chemical modification.

In some embodiments, the C1-INH protein is expressed from a cell line engineered to enhance glycosylation has a glycosylation profile that is changed, improved, enhanced, humanized, and/or optimized compared to a C1-INH protein having the same sequence that is expressed from the same cell line that has not been engineered to enhance glycosylation. In some embodiments, the C1-INH protein is expressed from a cell line engineered to enhance sialylation has a sialylation profile that is changed, improved, enhanced, humanized, and/or optimized compared to a C1-INH protein having the same sequence that is expressed from the same cell line that has not been engineered to enhance sialylation.

In some embodiments, the C1-INH protein is expressed from a cell line cultured under conditions to enhance glycosylation has a glycosylation profile that is changed, improved, enhanced, humanized, and/or optimized compared to a C1-INH protein having the same sequence that is expressed from a cell line cultured under conditions to enhance glycosylation. In some embodiments, the C1-INH protein is expressed from a cell line cultured under conditions to enhance sialylation has a sialylation profile that is changed, improved, enhanced, humanized, and/or optimized compared to a C1-INH protein having the same sequence that is expressed from a cell line cultured under conditions to enhance sialylation.

In some embodiments the C1-INH protein has a glycosylation profile that is changed, improved, enhanced, humanized, and/or optimized compared to Ruconest. In some embodiments the C1-INH protein has a glycosylation profile that is changed, improved, enhanced, humanized, and/or optimized compared to human plasma-derived C1-INH.

In some embodiments the cell culture conditions are manipulated to achieve expression of proteins having a desired glycosylation profile. These cell culture conditions include control of the production and culture process including length of culture, additives to culture medium, co-expression of genes to enhance glycosylation via increased glycosylation, and/or engineering of cells to knock out, prevent expression of, inactivate, or disrupt enzymes associated with glycan degradation (e.g., sialyladase). Suitable methods for manipulation of glycosylation include, but are not limited to, those described in, e.g., U.S. Pat. Nos. 5,047,335; 5,096,816; 5,705,364; 7,645,609; 8,273,723; 8,524,477; 8,617,878; 8,871,723; PCT Publication Nos. WO2006/106348; WO2007/095506; WO2008/025856; WO2010/007214; WO2010/099394; and WO2013/093760, the disclosures of which are incorporated herein by reference.

Selection of host cells and specific clones of transfected host cells may also be used to enhance glycosylation. Some methods of enhancing glycosylation include purification processes to enrich for proteins or polypeptides having the desired glycosylation profile.

Various methods of manipulating the sialylation profile of proteins are known in the art. These methods as well as others yet to be discovered are contemplated by the instant invention. Methods of manipulating the sialylation profile of C1-INH proteins and polypeptides of the invention include in vitro, in situ, and in vivo methods. In some embodiments the sialylation profile of expressed proteins or polypeptides is altered through post-expression chemical modification of the expressed protein or polypeptide. In some embodiments the cell culture conditions are manipulated to achieve expression of proteins having a desired sialylation profile. These cell culture conditions include control of the production and culture process including length of culture, additives to culture medium, and/or co-expression of genes to enhance sialylation. Selection of host cells and specific clones of transfected host cells may also be used to enhance sialylation. Some methods of enhancing sialylation include purification processes to enrich for proteins or polypeptides having the desired sialylation profile.

Sialylation can also be manipulated through the various methods described herein. Without wishing to be bound by any theory, decreased sialylation was found to be associated with increased heparin binding of the disclosed constructs, thereby preventing the C1-INH binding site from binding to targets. Heparin binding also increases likelihood of internalization into the lysosome, thereby increasing the rate of clearance.

Mammalian Cell Lines

Any mammalian cell or cell type susceptible to cell culture, and to expression of polypeptides, may be utilized in accordance with the present invention as a host cell. Non-limiting examples of mammalian cells that may be used in accordance with the present invention include human embryonic kidney 293 cells (HEK293), HeLa cells; BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells +/−DHFR (CHO, Urlaub and Chasin, Proc. Natl. Acad. Sci. USA, 77:4216 (1980)); mouse sertoli cells (TM4, Mather, Biol. Reprod., 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); MRC 5 cells; FS4 cells; and a human hepatoma line (Hep G2). In some embodiments, a suitable mammalian cell is not an endosomal acidification-deficient cell.

Additionally, any number of commercially and non-commercially available hybridoma cell lines that express polypeptides or proteins may be utilized in accordance with the present invention. One skilled in the art will appreciate that hybridoma cell lines might have different nutrition requirements and/or might require different culture conditions for optimal growth and polypeptide or protein expression, and will be able to modify conditions as needed.

Non-Mammalian Cell Lines

Any non-mammalian derived cell or cell type susceptible to cell culture, and to expression of polypeptides, may be utilized in accordance with the present invention as a host cell. Non-limiting examples of non-mammalian host cells and cell lines that may be used in accordance with the present invention include cells and cell lines derived from *Pichia pastoris, Pichia methanolica, Pichia angusta, Schizosacccharomyces pombe, Saccharomyces cerevisiae,* and *Yarrowia lipolytica* for yeast; *Sodoptera frugiperda, Trichoplusis ni, Drosophila melangoster* and *Manduca sexta* for insects; and *Escherichia coli, Salmonella typhimurium, Bacillus subtilis, Bacillus lichenifonnis, Bacteroides fragilis, Clostridia perfringens, Clostridia difficile* for bacteria; and *Xenopus laevis* from amphibian.

Adaptable to Adherent vs Suspension Growth

In certain embodiments, a host cell is selected for generating a cell line based on certain preferable attributes or growth under particular conditions chosen for culturing cells. It will be appreciated by one skilled in the art, such attributes may be ascertained based on known characteristic and/or traits of an established line (i.e. a characterized commercially available cell line) or though empirical evaluation. In some embodiments, a cell line may be selected for its ability to grow on a feeder layer of cells. In some embodiments, a cell line may be selected for its ability to grow in suspension. In some embodiments, a cell line may be selected for its ability to grow as an adherent monolayer of cells. In some embodiments, such cells can be used with any tissue culture vessel or any vessel treated with a suitable adhesion substrate. In some embodiments, a suitable adhesion substrate is selected from the group consisting of collagen (e.g. collagen I, II, II, or IV), gelatin, fibronectin, laminin, vitronectin, fibrinogen, BD Matrigel™, basement membrane matrix, dermatan sulfate proteoglycan, Poly-D-Lysine and/or combinations thereof. In some embodiments, an adherent host cell may be selected and modified under specific growth conditions to grow in suspension. Such methods of modifying an adherent cell to grown in suspension are known in the art. For example, a cell may be conditioned to grow in suspension culture, by gradually removing animal serum from the growth media over time.

Cell Line Selection and Evaluation

According to the present invention, a cell engineered to express rhC1-INH protein is selected for its ability to produce the rhC1-INH protein at commercially viable scale. In particular, engineered cells according to the present invention are able to produce rhC1-INH protein at a high level and/or with high enzymatic activity. In some embodiments, desirable cells, once cultivated under a cell culture condition (e.g., a standard large scale suspension or adherent culture condition), can produce C1-INH protein in an amount of or greater than about 5 picogram/cell/day (e.g., greater than about 10, 15, 20, 25, 30, 35, 40, 45, 50, 55, 60, 65, 70, 75, 80, 85, 90, 95, or 100 picogram/cell/day). In some embodiments, desired cells, once cultivated under a cell culture condition (e.g., a standard large scale suspension or adherent culture condition), are able to produce C1-INH protein in an amount ranging from about 5-100 picogram/cell/day (e.g., about 5-90 picogram/cell/day, about 5-80 picogram/cell/day, about 5-70 picogram/cell/day, about 5-60 picogram/cell/day, about 5-50 picogram/cell/day, about 5-40 picogram/cell/day, about 5-30 picogram/cell/day, about 10-90 picogram/cell/day, about 10-80 picogram/cell/day, about 10-70 picogram/cell/day, about 10-60 picogram/cell/day, about 10-50 picogram/cell/day, about 10-40 picogram/cell/day, about 10-30 picogram/cell/day, about 20-90 picogram/cell/day, about 20-80 picogram/cell/day, about 20-70 picogram/cell/day, about 20-60 picogram/cell/day, about 20-50 picogram/cell/day, about 20-40 picogram/cell/day, about 20-30 picogram/cell/day).

Cell Culture Medium and Condition

Various cell culture medium and conditions may be used to produce an rhC1-INH protein using engineered cells according to the present invention. For example, an rhC1-INH protein may be produced in serum-containing or serum-free medium. In some embodiments, an rhC1-INH protein is produced in serum-free medium. In some embodiments, an rhC1-INH protein is produced in an animal free medium, i.e., a medium that lacks animal-derived components. In some embodiments, an rhC1-INH protein is produced in a chemically defined medium. As used herein, the term "chemically-defined nutrient medium" refers to a medium of which substantially all of the chemical components are known. In some embodiments, a chemically defined nutrient medium is free of animal-derived components such as serum, serum derived proteins (e.g., albumin or fetuin), and other components. In some embodiments, a chemically-defined medium comprises one or more proteins (e.g., protein growth factors or cytokines). In some embodiments, a chemically-defined nutrient medium comprises one or more protein hydrolysates. In some embodiments, a chemically-defined nutrient medium is a protein-free media, i.e., a serum-free media that contains no proteins, hydrolysates or components of unknown composition.

In some embodiments, a chemically defined medium may be supplemented by one or more animal derived components. Such animal derived components include, but are not limited to, fetal calf serum, horse serum, goat serum, donkey serum, human serum, and serum derived proteins such as albumins (e.g., bovine serum albumin or human serum albumin).

Various cell culture conditions may be used to produce rhC1-INH proteins at large scale including, but not limited to, roller bottle cultures, bioreactor batch cultures, perfusion cultures, and bioreactor fed-batch cultures. In some embodiments, rhC1-INH protein is produced by cells cultured in suspension. In some embodiments, rhC1-INH protein is produced by adherent cells. In some embodiments, perfusion culture is used to control glycosylation of expressed protein. Exemplary methods of perfusion culture include, but are not limited to, those described in, e.g., U.S. Pat. No. 6,528,286 and PCT Publication No. WO1996/039488A1, the disclosures of which are incorporated herein by reference.

Exemplary cell media and culture conditions are described in the Examples sections. The examples are not intended to be limiting.

Culture Initiation

A desired cell expressing C1-INH protein can first be propagated in an initial culture by any of the variety of methods well-known to one of ordinary skill in the art. The cell is propagated by growing it at a temperature and in a medium that is conducive to the survival, growth and viability of the cell. The initial culture volume can be of any size, but is often smaller than the culture volume of the production bioreactor used in the final production, and frequently cells are passaged several times of increasing culture volume prior to seeding the production bioreactor. The cell culture can be agitated or shaken to increase oxygenation of the medium and dispersion of nutrients to the cells. Alternatively or additionally, special sparging devices that are well known in the art can be used to increase and control oxygenation of the culture.

The starting cell density can be chosen by one of ordinary skill in the art. In accordance with the present invention, the starting cell density can be as low as a single cell per culture volume. In some embodiments, starting cell densities can range from about $1 \times 10^2$ viable cells per mL to about $1 \times 10^3$, $1 \times 10^4$, $1 \times 10^5$, $1 \times 10^6$ viable cells per mL and higher.

Initial and intermediate cell cultures may be grown to any desired density before seeding the next intermediate or final production bioreactor. In some embodiments, final viability before seeding the production bioreactor is greater than about 70%, 75%, 80%, 85%, 90%, 95%, or more. The cells may be removed from the supernatant, for example, by low-speed centrifugation. It may also be desirable to wash the removed cells with a medium before seeding the next bioreactor to remove any unwanted metabolic waste products or medium components. The medium may be the medium in which the cells were previously grown or it may be a different medium or a washing solution selected by the practitioner of the present invention.

The cells may then be diluted to an appropriate density for seeding the production bioreactor. In some embodiments, the cells are diluted into the same medium that will be used in the production bioreactor. Alternatively, the cells can be diluted into another medium or solution, depending on the needs and desires of the practitioner of the present invention or to accommodate particular requirements of the cells themselves, for example, if they are to be stored for a short period of time prior to seeding the production bioreactor.

Growth Phase

Typically, once the production bioreactor has been seeded as described above, the cell culture is maintained in the initial growth phase under conditions conducive to the survival, growth and viability of the cell culture. In accordance with the present invention, the production bioreactor can be any volume that is appropriate for large-scale production of proteins. See the "Bioreactor" subsection below.

The temperature of the cell culture in the growth phase is selected based primarily on the range of temperatures at which the cell culture remains viable. The temperature of the growth phase may be maintained at a single, constant temperature, or within a range of temperatures. For example, the temperature may be steadily increased or decreased during the growth phase. In general, most mammalian cells grow well within a range of about 25° C. to 42° C. (e.g., 30° C. to 40° C., about 30° C. to 37° C., about 35° C. to 40° C.). In some embodiments, the mammalian cells are cultured at a temperature ranging from about 30-37° C. (e.g., about 31-37° C., about 32-37° C., about 33-37° C., about 34-37° C., about 35-37° C., about 36-37° C.). In some embodiments, the mammalian cells are cultured at a temperature ranging from about 30-34° C. (e.g., about 31-34° C., about 31-35° C., about 32-34° C., about 33-34° C., about 33-35° C.). Typically, during the growth phase, cells grow at about 28° C., about 30° C., about 31° C., about 32° C., about 33° C., about 34° C., about 35° C., about 36° C., about 37° C., about 38° C., about 39° C., or about 40° C.

The cells may be grown during the initial growth phase for a greater or lesser amount of time, depending on the needs of the practitioner and the requirement of the cells themselves. In one embodiment, the cells are grown for a period of time sufficient to achieve a viable cell density that is a given percentage of the maximal viable cell density that the cells would eventually reach if allowed to grow undisturbed. For example, the cells may be grown for a period of time sufficient to achieve a desired viable cell density of 1, 5, 10, 15, 20, 25, 30, 35, 40, 45, 50, 55, 60, 65, 70, 75, 80, 85, 90, 95 or 99 percent of maximal viable cell density.

In some embodiment, the cells are allowed to grow for a defined period of time. For example, depending on the starting concentration of the cell culture, the temperature at which the cells are grown, and the intrinsic growth rate of the cells, the cells may be grown for 0, 1, 2, 3, 4, 5, 6, 7, 8, 9, 10, 11, 12, 13, 14, 15, 16, 17, 18, 19, 20 or more days. In some cases, the cells may be allowed to grow for a month or more.

In some embodiments, the cells are allowed to grow to a desired viable cell density. For example, a desired viable cell density by the end of growth phase is greater than about $1.0 \times 10^6$ viable cells/mL, $1.5 \times 10^6$ viable cells/mL, $2.0 \times 10^6$ viable cells/mL, $2.5 \times 10^6$ viable cells/mL, $5 \times 10^6$ viable cells/mL, $10 \times 10^6$ viable cells/mL, $20 \times 10^6$ viable cells/mL, $30 \times 10^6$ viable cells/mL, $40 \times 10^6$ viable cells/mL, or $50 \times 10^6$ viable cells/mL.

The cell culture may be agitated or shaken during the initial culture phase in order to increase oxygenation and dispersion of nutrients to the cells. In accordance with the present invention, one of ordinary skill in the art will understand that it can be beneficial to control or regulate certain internal conditions of the bioreactor during the initial growth phase, including but not limited to pH, temperature, oxygenation, etc. For example, pH can be controlled by supplying an appropriate amount of acid or base and oxygenation can be controlled with sparging devices that are well known in the art. In some embodiments, a desired pH for the growth phase ranges from about 6.8-7.5 (e.g., about 6.9-7.4, about 6.9-7.3, about 6.95-7.3, about 6.95-7.25, about 7.0-7.3, about 7.0-7.25, about 7.0-7.2, about 7.0-7.15, about 7.05-7.3, about 7.05-7.25, about 7.05-7.15, about 7.05-7.20, about 7.10-7.3, about 7.10-7.25, about 7.10-7.20, about 7.10-7.15). In some embodiments, a desired pH for the growth phase is about 6.8, 6.85, 6.9, 6.95, 7.0, 7.05, 7.1, 7.15, 7.2, 7.25, 7.3, 7.35, 7.4, 7.45, or 7.5.

In some embodiments, a desired dissolved oxygen set point for the growth phase ranges from about 0%-70%, about 5%-60%, about 25%-50%, about 20%-40%, about 30%-60%. In some embodiments, a desired dissolved oxygen set point for the growth phase is about 5%, 10%, 15%, 20%, 25%, 30%, 35%, 40%, 45%, 50%, 55%, or 60%.

Transition Phase

In some embodiments, when the cells are ready for the production phase, the culture conditions may be changed to maximize the production of the recombinant protein of interest. Such culture condition change typically takes place in a transition phase. In some embodiments, such change may be a shift in one or more of a number of culture conditions including, but not limited to, temperature, pH, osmolarity, and medium. In one embodiment, the pH of the culture is shifted. For example, the pH of the medium may be increased or decreased from growth phase to the production phase. In some embodiments, this change in pH is rapid. In some embodiments, this change in pH occurs slowly over a prolonged period of time. In some embodiments, the change in pH regulated by the addition of sodium bicarbonate. In some embodiments, the change in pH is initiated at the start of the transition phase and is maintained during the subsequent production phase.

In one embodiments, the glucose concentration of the cell culture medium is shifted. According to this embodiment, upon initiation of the transition phase, the glucose concentration within the cell culture is adjusted to a rate higher than 7.5 mM.

In some embodiments, the temperature is shifted up or down from the growth phase to production phase. For example, the temperature may be shifted up or down from growth phase to the production phase by about 0.1° C., 0.2° C., 0.3° C., 0.4° C., 0.5° C., 1.0° C., 1.5° C., 2.0° C., 2.5° C., 3.0° C., 3.5° C., 4.0° C., 4.5° C., 5.0° C., 5.5° C., 6.0° C., 6.5° C., 7.0° C., 7.5° C., 8.0° C., or more.

Production Phase

In accordance with the present invention, once the cell culture reaches a desired cell density and viability, with or without a transition phase, the cell culture is maintained for a subsequent production phase under culture conditions conducive to the survival and viability of the cell culture and appropriate for expression of C1-INH protein at commercially adequate levels.

In some embodiments, during the production phase, the culture is maintained at a temperature or temperature range that is lower than the temperature or temperature range of the growth phase. For example, during the production phase, cells may express rhC1-INH protein well within a range of about 25° C. to 35° C. (e.g., about 28° C. to 35° C., about 30° C. to 35° C., about 32° C. to 35° C.). In some embodiments, during the production phase, cells may express rhC1-INH protein well at a temperature of about 25° C., about 26° C., about 27° C., about 28° C., about 29° C., about 30° C., about 31° C., about 32° C., about 33° C., about 34° C., about 35° C., about 36° C., about 37° C. In other embodiments, during the production phase, the culture is maintained at a temperature or temperature range that is higher than the temperature or temperature range of the growth phase.

Additionally or alternatively, during the production phase, the culture is maintained at a pH or pH range that is different (lower or higher) than the pH or pH range of the growth phase. In some embodiments, the medium for the production phase has a pH ranging from about 6.8-7.5 (e.g., about 6.9-7.4, about 6.9-7.3, about 6.95-7.3, about 6.95-7.25, about 7.0-7.3, about 7.0-7.25, about 7.0-7.2, about 7.0-7.15, about 7.05-7.3, about 7.05-7.25, about 7.05-7.15, about 7.05-7.20, about 7.10-7.3, about 7.10-7.25, about 7.10-7.20, about 7.10-7.15). In some embodiments, the medium has a pH of about 6.8, 6.85, 6.9, 6.95, 7.0, 7.05, 7.1, 7.15, 7.2, 7.25, 7.3, 7.35, 7.4, 7.45, or 7.5.

In some embodiments, a desired dissolved oxygen set point for the production phase ranges from about 0%-70%, about 5%-60%, about 25%-50%, about 20%-40%, about 30%-60%. In some embodiments, a desired dissolved oxygen set point for the production phase is about 5%, 10%, 15%, 20%, 25%, 30%, 35%, 40%, 45%, 50%, 55%, or 60%.

In some embodiments, the cells may be maintained within a desired viable cell density range throughout the production. For example, during the production phase of the cell culture, a desired viable cell density may range from about $1.0\text{-}50\times10^6$ viable cells/mL during the production phase (e.g., about $1.0\text{-}40\times10^6$ viable cells/mL, about $1.0\text{-}30\times10^6$ viable cells/mL, about $1.0\text{-}20\times10^6$ viable cells/mL, about $1.0\text{-}10\times10^6$ viable cells/mL, about $1.0\text{-}5\times10^6$ viable cells/mL, about $1.0\text{-}4.5\times10^6$ viable cells/mL, about $1.0\text{-}4\times10^6$ viable cells/mL, about $1.0\text{-}3.5\times10^6$ viable cells/mL, about $1.0\text{-}3\times10^6$ viable cells/mL, about $1.0\text{-}2.5\times10^6$ viable cells/mL, about $1.0\text{-}2.0\times10^6$ viable cells/mL, about $1.0\text{-}1.5\times10^6$ viable cells/mL, about $1.5\text{-}10\times10^6$ viable cells/mL, about $1.5\text{-}5\times10^6$ viable cells/mL, about $1.5\text{-}4.5\times10^6$ viable cells/mL, about $1.5\text{-}4\times10^6$ viable cells/mL, about $1.5\text{-}3.5\times10^6$ viable cells/mL, about $1.5\text{-}3.0\times10^6$ viable cells/mL, about $1.5\text{-}2.5\times10^6$ viable cells/mL, about $1.5\text{-}2.0\times10^6$ viable cells/mL).

In some embodiments, the cells may be maintained for a period of time sufficient to achieve a viable cell density of 1, 5, 10, 15, 20, 25, 30, 35, 40, 45, 50, 55, 60, 65, 70, 75, 80, 85, 90, 95 or 99 percent of maximal viable cell density. In some cases, it may be desirable to allow the viable cell density to reach a maximum. In some embodiments, it may be desirable to allow the viable cell density to reach a maximum and then allow the viable cell density to decline to some level before harvesting the culture. In some embodiments, the total viability at the end of the production phase is less than about 90%, 85%, 80%, 75%, 70%, 65%, 60%, 55%, 50%, 45%, 40%, 35%, 30%, 25%, 20%, 15%, 10%, 5%.

In some embodiments, the cells are allowed to grow for a defined period of time during the production phase. For example, depending on the concentration of the cell culture at the start of the subsequent growth phase, the temperature at which the cells are grown, and the intrinsic growth rate of the cells, the cells may be grown for about 5-90 days (e.g., about 5-80 days, about 5-70 days, about 5-60 days, about 5-50 days, about 5-40, about 5-30 days, about 5-20 days, about 5-15 days, about 5-10 days, about 10-90 days, about 10-80 days, about 10-70 days, about 10-60 days, about 10-50 days, about 10-40 days, about 10-30 days, about 10-20 days, about 15-90 days, about 15-80 days, about 15-70 days, about 15-60 days, about 15-50 days, about 15-40 days, about 15-30 days). In some embodiments, the production phase is lasts for about 5, 10, 15, 20, 25, 30, 35, 40, 45, 50, 55, 60, 65, 70, 75, 80, 85, or 90 days.

In some embodiments, the cells are maintained in the production phase until the titer to the rhC1-INH protein reaches a maximum. In other embodiments, the culture may be harvested prior to this point. For example, in some embodiments, the cells are maintained in the production phase until the titer to the rhC1-INH protein reaches a desired titer. Thus, a desired average harvest titer to the rhC1-INH protein may be of at least 6 mg per liter per day (mg/L/day) (e.g., at least 8, 10, 12, 14, 16, 18, 20, 25, 30, 35, 40, 45, 50, 55, 60, 65, 70, 75, 80, 85, 90, 95, 100, 150, 200, 250, 300, 350, 400, 450, or 500 mg/L/day, or more). In some embodiments, a desired average harvest titer to the rhC1-INH protein may range from about 6-500 mg/L/day (e.g., about 6-400 mg/L/day, about 6-300 mg/L/day, about 6-200 mg/L/day, about 6-100 mg/L/day, about 6-90 mg/L/day, about 6-80 mg/L/day, about 6-70 mg/L/day, about 6-60 mg/L/day, about 6-50 mg/L/day, about 6-40 mg/L/day, about 6-30 mg/L/day, about 10-500 mg/L/day, about 10-400 mg/L/day, about 10-300 mg/L/day, about 10-200 mg/L/day, about 10-100 mg/L/day, about 10-90 mg/L/day, about 10-80 mg/L/day, about 10-70 mg/L/day, about 10-60 mg/L/day, about 10-50 mg/L/day, about 10-40 mg/L/day, about 10-30 mg/L/day, about 20-500 mg/L/day, about 20-400 mg/L/day, about 20-300 mg/L/day, about 20-200 mg/L/day, about 20-100 mg/L/day, about 20-90 mg/L/day, about 20-80 mg/L/day, about 20-70 mg/L/day, about 20-60 mg/L/day, about 20-50 mg/L/day, about 20-40 mg/L/day, about 20-30 mg/L/day). In some embodiments, it may be beneficial or necessary to supplement the cell culture during the production phase with nutrients or other medium components that have been depleted or metabolized by the cells. For example, it might be advantageous to supplement the cell culture with nutrients or other medium components observed to have been depleted during the cell culture. Alternatively or additionally, it may be beneficial or necessary to supplement the cell culture prior to the production phase. As non-limiting examples, it may be beneficial or necessary to supplement the cell culture with redox-modulators, growth modulators (e.g., hormones and/or other growth factors), glycosylation modulators, particular ions (e.g., sodium, chloride, calcium, magnesium, manganese, phosphate), buffers, vitamins, nucleosides or nucleotides, trace elements (inorganic compounds usually present at very low final concentrations), amino acids, lipids, peptones, yeast extracts, plant hydrolysates, soy hydrolysates, serum, lipid supplements, nucleotide sugars, nucleotide sugar precursors, ammonia, glucosamine, uridine, sialic acid precursors, N-acetylmannosamine, glucose, galactose, amino acids (e.g., glutamine, cysteine, isoleucine, leucine, tryptophan, valine, asparagine, aspartic acid, glutamate), sugars (e.g., glucose, galactose, sialic acid), or energy sources.

These supplementary components may all be added to the cell culture at one time, or they may be provided to the cell culture in a series of additions. In some embodiments, the supplementary components are provided to the cell culture at multiple times in proportional amounts. In other embodiments, the cell culture is fed continually with these supplementary components. Typically, this process is known as perfusion and a cell culture involving perfusion is known as "perfusion culture." As used herein, the term "perfusion culture" refers to a method of culturing cells in which additional components are provided continuously or semi-continuously to the culture subsequent to the beginning of the culture process. A portion of the cells and/or components in the medium are typically harvested on a continuous or semi-continuous basis and are optionally purified.

In some embodiments, the medium is continuously exchanged by a perfusion process during the production phase. Typically, volume of fresh medium relative to working volume of reactor per day (VVD) is defined as perfusion rate. Various perfusion rates may be used in according to the present invention. In some embodiments, a perfusion process has a perfusion rate such that the total volume added to the cell culture be kept to a minimal amount. In some embodiments, the perfusion process has a perfusion rate ranging from about 0.5-2 volume of fresh medium/working volume of reactor/day (VVD) (e.g., about 0.5-1.5 VVD, about 0.75-1.5 VVD, about 0.75-1.25 VVD, about 1.0-2.0 VVD, about 1.0-1.9 VVD, about 1.0-1.8 VVD, about 1.0-1.7 VVD, about 1.0-1.6 VVD, about 1.0-1.5 VVD, about 1.0-1.4 VVD, about 1.0-1.3 VVD, about 1.0-1.2 VVD, about 1.0-1.1 VVD). In some embodiments, the perfusion process has a perfusion rate of about 0.5, 0.55, 0.6, 0.65, 0.7, 0.75, 0.8, 0.85, 0.9, 0.95, 1.0, 1.05, 1.10, 1.15, 1.2, 1.25, 1.3, 1.35, 1.4, 1.45, 1.5, 1.55, 1.6, 1.65, 1.7, 1.75, 1.8, 1.85, 1.9, 1.95, or 2.0 VVD.

A perfusion process may also be characterized by volume of fresh medium added per cell per day, which is defined as cell specific perfusion rate. Various cell specific perfusion rates may be used. In some embodiments, the perfusion process has a cell specific perfusion rate ranging from about 0.05-5 nanoliter per cell per day (nL/cell/day) (e.g., about 0.05-4 nL/cell/day, about 0.05-3 nL/cell/day, about 0.05-2 nL/cell/day, about 0.05-1 nL/cell/day, about 0.1-5 nL/cell/day, about 0.1-4 nL/cell/day, about 0.1-3 nL/cell/day, about 0.1-2 nL/cell/day, about 0.1-1 nL/cell/day, about 0.15-5 nL/cell/day, about 0.15-4 nL/cell/day, about 0.15-3 nL/cell/day, about 0.15-2 nL/cell/day, about 0.15-1 nL/cell/day, about 0.2-5 nL/cell/day, about 0.2-4 nL/cell/day, about 0.2-3 nL/cell/day, about 0.2-2 nL/cell/day, about 0.2-1 nL/cell/day, about 0.25-5 nL/cell/day, about 0.25-4 nL/cell/day, about 0.25-3 nL/cell/day, about 0.25-2 nL/cell/day, about 0.25-1 nL/cell/day, about 0.3-5 nL/cell/day, about 0.3-4 nL/cell/day, about 0.3-3 nL/cell/day, about 0.3-2 nL/cell/day, about 0.3-1 nL/cell/day, about 0.35-5 nL/cell/day, about 0.35-4 nL/cell/day, about 0.35-3 nL/cell/day, about 0.35-2 nL/cell/day, about 0.35-1 nL/cell/day, about 0.4-5 nL/cell/day, about 0.4-4 nL/cell/day, about 0.4-3 nL/cell/day, about 0.4-2 nL/cell/day, about 0.4-1 nL/cell/day, about 0.45-5 nL/cell/day, about 0.45-4 nL/cell/day, about 0.45-3 nL/cell/day, about 0.45-2 nL/cell/day, about 0.45-1 nL/cell/day, about 0.5-5 nL/cell/day, about 0.5-4 nL/cell/day, about 0.5-3 nL/cell/day, about 0.5-2 nL/cell/day, about 0.5-1 nL/cell/day). In some embodiments, the perfusion process has a cell specific perfusion rate of about 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 nL/cell/day.

The cell culture may be agitated or shaken during the production phase in order to increase oxygenation and dispersion of nutrients to the cells. In accordance with the present invention, one of ordinary skill in the art will understand that it can be beneficial to control or regulate certain internal conditions of the bioreactor during the growth phase, including but not limited to pH, temperature, oxygenation, etc. For example, pH can be controlled by supplying an appropriate amount of acid or base and oxygenation can be controlled with sparging devices that are well known in the art. One or more antiform agents may also be provided.

Same culture medium may be used throughout the production process including the growth phase, production phase and profusion. In some embodiments, at least two different media are used in the production of rhC1-INH. For example, a nutrient medium formulated for cell growth is often used to support growth of the cells throughout the cell growth phase, and nutrient medium formulated for protein production is used during the production phase of the process to support expression and harvesting of C1-INH. In either case, the nutrient medium may or may not contain serum or other animal-derived components (e.g., fetuin).

According to the present invention, the cells are typically grown in suspension. However, the cells may be attached to a substrate. In one example, cells may be attached to microbead or particles which are suspended in the nutrient medium.

Bioreactors

The invention also provides bioreactors that are useful for producing rhC1-INH. Bioreactors may be perfusion, batch, fed-batch, repeated batch, or continuous (e.g. a continuous stirred-tank reactor models), for example. Typically, the bioreactors comprise at least one vessel designed and are configured to house medium (e.g., a chemically defined nutrient medium). The vessel also typically comprises at least one inlet designed and configured to flow fresh nutrient medium into the vessel. The vessel also typically comprises at least one outlet designed and configured to flow waste medium out of the vessel. In some embodiments, the vessel may further comprise at least one filter designed and configured to minimize the extent to which isolated cells in the vessel are passed out through the at least one outlet with waste medium. The bioreactor may also be fitted with one or more other components designed to maintain conditions suitable for cell growth. For example, the bioreactor may be fitted with one or more circulation or mixing devices designed and configured to circulate or mix the nutrient medium within the vessel. Typically, the isolated cells that are engineered to express rhC1-INH are suspended in the nutrient medium. Therefore, in some cases, the circulation device ensures that the isolated cells remain in suspension in the nutrient medium. In some cases, the cells are attached to a substrate. In some cases, the cells are attached to one or more substrates (e.g., microbeads) that are suspended in the nutrient medium. The bioreactor may comprise one or more ports for obtaining a sample of the cell suspension from the vessel. The bioreactor may be configured with one or more components for monitoring and/or controlling conditions of the culture, including conditions such as gas content (e.g., air, oxygen, nitrogen, carbon dioxide), flow rates, temperature, pH and dissolved oxygen levels, and agitation speed/circulation rate.

Vessels of any appropriate size may be used in the bioreactors. Typically, the vessel size is suitable for satisfying the production demands of manufacturing rhC1-INH. In some embodiments, the vessel is designed and configured to contain up to 1 L, up to 10 L, up to 100 L, up to 500 L, up to 1000 L, up to 1500 L, up to 2000 L, or more of the nutrient medium. In some embodiments, the volume of the production bioreactor is at least 10 L, at least 50 L, 100 L, at least 200 L, at least 250 L, at least 500 L, at least 1000 L, at least 1500 L, at least 2000 L, at least 2500 L, at least 5000 L, at least 8000 L, at least 10,000 L, at least 12,000 L, at least 15,000 L, or at least 20,000 L or more, or any volume in between. The production bioreactor may be constructed of any material that is conducive to cell growth and viability that does not interfere with expression or stability or activity of the produced C1-INH protein. Exemplary material may include, but not be limited to, glass, plastic, or metal.

In some embodiments, cells may be cultured in a chemically defined medium that is housed in a vessel of a bioreactor. The culture methods often involve perfusing fresh nutrient medium into the vessel through the at least one inlet and bleeding waste nutrient medium out from vessel through the at least one outlet. Bleeding is performed at a rate of up to about 0.1 vessel volume per day, about 0.2 vessel volume per day, about 0.3 vessel volume per day, about 0.4 vessel volume per day, about 0.5 vessel volume per day, about 1 vessel volume per day, about 1.5 vessel volumes per day or more. The methods also involve harvesting nutrient medium that comprises rhC1-INH. Harvesting may be performed at a rate of up to about 0.1 vessel volume per day, about 0.2 vessel volume per day, about 0.3 vessel volume per day, about 0.4 vessel volume per day, about 0.5 vessel volume per day, about 1 vessel volume per day, about 1.5 vessel volumes per day or more. Perfusing is also performed, typically at a rate equivalent to the sum of the bleeding rate and the harvesting rate. For example, perfusion rate may be greater than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0 vessel volume per day. In some embodiments, perfusion rate is less than about 5.0, 4.5, 4.0, 3.5, 3.0, 2.5, 2.0, 1.5, 1.4, 1.3, 1.2, 1.1, 1.0, 0.9, 0.8, 0.7, 0.6, 0.5 vessel volume per day. Exemplary perfusion rates are described throughout the specification.

Monitoring Culture Conditions

In certain embodiments of the present invention, the practitioner may find it beneficial or necessary to periodically monitor particular conditions of the growing cell culture. Monitoring cell culture conditions allows the practitioner to determine whether the cell culture is producing recombinant polypeptide or protein at suboptimal levels or whether the culture is about to enter into a suboptimal production phase. In order to monitor certain cell culture conditions, it will be necessary to remove small aliquots of the culture for analysis.

As non-limiting example, it may be beneficial or necessary to monitor temperature, pH, cell density, cell viability, integrated viable cell density, osmolarity, or titer or activity of the expressed C1-INH protein. Numerous techniques are well known in the art that will allow one of ordinary skill in the art to measure these conditions. For example, cell density may be measured using a hemocytometer, a Coulter counter, or Cell density examination (CEDEX). Viable cell density may be determined by staining a culture sample with Trypan blue. Since only dead cells take up the Trypan blue, viable cell density can be determined by counting the total number of cells, dividing the number of cells that take up the dye by the total number of cells, and taking the reciprocal. Alternatively, the level of the expressed C1-INH protein can be determined by standard molecular biology techniques such as Coomassie staining of SDS-PAGE gels, Western blotting, Bradford assays, Lowry assays, Biuret assays, and UV absorbance. It may also be beneficial or necessary to monitor the post-translational modifications of the expressed C1-INH protein, including phosphorylation and glycosylation.

Exemplary cell media and culture conditions are described in the Examples sections. The examples are not intended to be limiting.

Purification of Expressed C1-INH Protein

Various methods may be used to purify or isolate C1-INH protein produced according to various methods described herein. In some embodiments, the expressed C1-INH protein is secreted into the medium and thus cells and other solids may be removed, as by centrifugation or filtering for example, as a first step in the purification process. Alternatively or additionally, the expressed C1-INH protein is bound to the surface of the host cell. In some embodiments, the host cells expressing the polypeptide or protein are lysed for purification. Lysis of mammalian host cells can be achieved by any number of means well known to those of ordinary skill in the art, including physical disruption by glass beads and exposure to high pH conditions.

The C1-INH protein may be isolated and purified by standard methods including, but not limited to, chromatography (e.g., ion exchange, affinity, size exclusion, and hydroxyapatite chromatography), gel filtration, centrifugation, or differential solubility, ethanol precipitation or by any other available technique for the purification of proteins (see, e.g., Scopes, *Protein Purification Principles and Practice* 2nd Edition, Springer-Verlag, New York, 1987; Higgins, S. J. and Hames, B. D. (eds.), *Protein Expression: A Practical Approach*, Oxford Univ Press, 1999; and Deutscher, M. P., Simon, M. I., Abelson, J. N. (eds.), *Guide to Protein Purification: Methods in Enzymology* (Methods in Enzymology Series, Vol 182), Academic Press, 1997, all incorporated herein by reference). For immunoaffinity chromatography in particular, the protein may be isolated by binding it to an affinity column comprising antibodies that were raised against that protein and were affixed to a stationary support. Alternatively, affinity tags such as an influenza coat sequence, poly-histidine, or glutathione-S-transferase can be attached to the protein by standard recombinant techniques to allow for easy purification by passage over the appropriate affinity column. Protease inhibitors such as phenyl methyl sulfonyl fluoride (PMSF), leupeptin, pepstatin, or aprotinin may be added at any or all stages in order to reduce or eliminate degradation of the polypeptide or protein during the purification process. Protease inhibitors are particularly desired when cells must be lysed in order to isolate and purify the expressed polypeptide or protein.

Exemplary purification methods that avoid the problems associated with purification of C1-INH proteins are described in the Examples sections below. Suitable resins for purification include, but are not limited to, anion exchange resin, albumin affinity resin, C1 esterase inhibitor affinity resin, and protein A resin. In some embodiments, a purification method that does not require a drop in pH is preferred. In some embodiments, a purification method that does not require an acidic pH for elution is preferred. In other embodiments, a stabilizer that prevents aggregation is utilized. In some embodiments, the stabilizer that prevents aggregation is used in a method requiring a drop in pH. Non-limiting examples of suitable stabilizers include EDTA.

Suitable methods for purification of the C1-INH proteins of the invention include, but are not limited to, those described in, e.g., U.S. Pat. Nos. 5,276,141; 7,384,754; 8,802,816; PCT Publication Nos. WO2012107572; and WO2013009526, the disclosures of which are incorporated herein by reference.

Reduction of Contaminants

Figure 14:
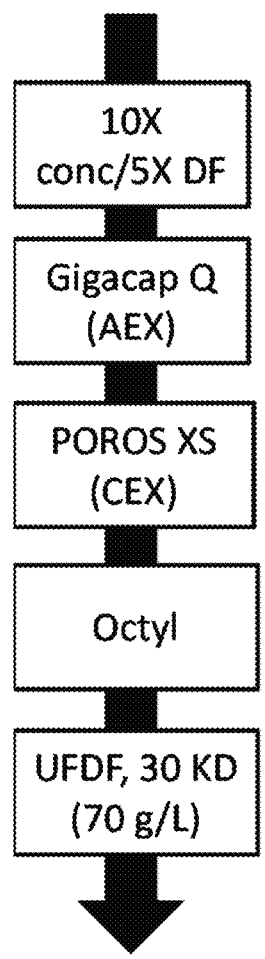
FIG. 14 depicts a schematic of an rhC1-INH protein purification process.

The present disclosure also provides methods to reduce non-target protein contaminants or impurities in a downstream process. In one embodiment, the downstream process is of rhC1-INH. Non-target protein contaminants include, for example, contaminating DNA, RNA, host cell proteins (HCP), and/or viruses, and/or any other substance that is not the target protein. In one embodiment, non-target protein contaminants are reduced by introducing an additional purification step to the rhC1-INH downstream process. An example of one downstream process for rhC1-INH, without the additional purification step, is depicted in FIG. 14.

Reduction of DNA, HCP, and/or virus contaminants can occur at any stage of the downstream process. In one embodiment, an Anion Exchange (AEX) membrane absorber is used to reduce contaminants. Examples of AEX membrane absorbers can include Sartobind Q, Sartobind STIC, and/or Natrix. In one embodiment, the reduction of DNA and/or host cell protein contaminants occurs by the introduction of an AEX membrane step after the POROS XS purification step depicted in FIG. 14. In one embodiment, the reduction of DNA, host cell protein, and/or virus contaminants occurs by the introduction of a Sartobind Q membrane absorber step after the POROS XS purification step in the downstream process depicted in FIG. 14. In one embodiment, the reduction of DNA contaminants occurs by the introduction of a Sartobind Q membrane absorber step after the POROS XS purification step in the downstream process depicted in FIG. 14. In one embodiment, the reduction of host cell protein contaminants occurs by the introduction of a Sartobind Q membrane absorber step after the POROS XS purification step in the downstream process depicted in FIG. 14. In one embodiment, the reduction of DNA contaminants occurs by the introduction of a Sartobind STIC membrane absorber step after the POROS XS purification step in the downstream process depicted in FIG. 14. In one embodiment, the reduction of host cell protein contaminants occurs by the introduction of a Sartobind STIC membrane absorber step after the POROS XS purification step in the downstream process depicted in FIG. 14.

Introducing the additional contaminant purification step can affect rhC1-INH yield and purity. In one embodiment, increased rhC1-INH yield and purity is obtained with the use of Sartobind Q AEX membrane, in comparison to the use of Sartobind STIC or Natrix membranes. In one embodiment, increased rhC1-INH yield and purity is obtained with the use of Sartobind Q AEX membrane following the POROS XS downstream process step.

Reduction of contaminants can be further improved by manipulating pH and/or conductivity parameters during the AEX membrane purification step. For example, lowering conductivity to about 5 mS/cm increases the reduction of contaminants, such as contaminating DNA, HCP and/or virus. In one embodiment, increased reduction of contaminants is achieved by having a conductivity of about 0.5-20 mS/cm. For example, the conductivity can be about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, or 20 mS/cm, or any number in between. In one embodiment, increased reduction of contaminants is achieved by having a conductivity of about 0.5-8 mS/cm. For example, the conductivity can be about 0.5, 1.0, 1.5, 2.0, 2.5, 3.0, 3.5, 4.0, 4.5, 5.0, 5.5, 6.0, 6.5, 7.0, 7.5, or 8.0 mS/cm, or any number in between. In one embodiment, increased reduction of contaminants is achieved by having a conductivity of about 3.0-6.0 mS/cm. For example, the conductivity can be about 3.0, 3.5, 4.0, 4.5, 5.0, 5.5, 6.0, or any number in between.

In one embodiment, increased reduction of contaminants is achieved by having a pH of about 5.0-9.0 in the AEX membrane purification step. For example, the pH can be about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0. In one embodiment, increased reduction of contaminants is achieved by having a pH of about 5.0-7.5. For example, the pH can be about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5.

Pharmaceutical Compositions

The present invention further provides a pharmaceutical composition containing an rhC1-INH protein described herein and a physiologically acceptable carrier or excipient. The carrier and rhC1-INH protein can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring, and/or aromatic substances and the like) which do not deleteriously react with the active compounds or interfere with their activity. In a preferred embodiment, a water-soluble carrier suitable for intravenous administration is used.

A suitable pharmaceutical composition or medicament, if desired, can also contain minor amounts of wetting or emulsifying agents, or pH buffering agents. A composition can be a liquid solution, suspension, emulsion, tablet, pill, capsule, sustained release formulation, or powder. A composition can also be formulated as a suppository, with traditional binders and carriers such as triglycerides. Oral formulations can include standard carriers such as pharmaceutical grades of mannitol, lactose, starch, magnesium stearate, polyvinyl pyrrolidone, sodium saccharine, cellulose, magnesium carbonate, etc.

A pharmaceutical composition or medicament can be formulated in accordance with the routine procedures as a pharmaceutical composition adapted for administration to human beings. For example, in some embodiments, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

An rhC1-INH protein described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

A preferred formulation comprises 50 mM NaPO4 (pH 7.2), 50 mM Sorbitol, and 150 mM Glycine. In some embodiments, the formulation comprises about 50 mM NaPO4 (about pH 7.2), about 50 mM Sorbitol, and about 150 mM Glycine. For example, in some embodiments the formulation comprises about 20, 25, 30, 35, 40, 45, 50, 55, 60, 65, 70, 75, or 80 mM NaPO4 (pH 7.2); the NaPO4 pH is about 6.5, 6.6, 6.7, 6.8, 6.9, 7.0, 7.1, 7.2, 7.3, 7.4, 7.5, 7.6, 7.7, 7.8, 7.9, or 8.0; the sorbitol concentration is about 20, 25, 30, 35, 40, 45, 50, 55, 60, 65, 70, 75, or 80 mM; and the glycine concentration is about 75, 80, 85, 90, 95, 100, 105, 110, 115, 120, 125, 130, 135, 140, 145, 150, 155, 160, 165, 170, 175, 180, 190, 195, or 200 mM.

Another preferred formulation comprises 70 mg/mL rhC1-INH in 150 mM glycine, 50 mM sorbitol, and 50 mM sodium phosphate buffer at pH 7.1. In some embodiments the formulation comprises about 70 mg/mL rhC1-INH in about 150 mM glycine, about 50 mM sorbitol, and about 50 mM sodium phosphate buffer at about pH 7.1 For example, in some embodiments, the rhC1-INH concentration is about 45, 50, 55, 60, 65, 70, 75, 80, 85, 90, 95, or 100 mg/mL; the glycine concentration is about 75, 80, 85, 90, 95, 100, 105, 110, 115, 120, 125, 130, 135, 140, 145, 150, 155, 160, 165, 170, 175, 180, 190, 195, or 200 mM; the sorbitol concentration is about 20, 25, 30, 35, 40, 45, 50, 55, 60, 65, 70, 75, or 80 mM; the sodium phosphate buffer is about 20, 25, 30, 35, 40, 45, 50, 55, 60, 65, 70, 75, or 80 mM; the pH of the sodium phosphate buffer is about 6.5, 6.6, 6.7, 6.8, 6.9, 7.0, 7.1, 7.2, 7.3, 7.4, 7.5, 7.6, 7.7, 7.8, 7.9, or 8.0.

Another preferred formulation comprises rhC1-INH in 150 mM glycine, 50 mM sorbitol, 150 mM Arg-HCl and 50 mM sodium phosphate buffer at pH 7.1. In one aspect, the formulation has increased stability at 2° C.-8° C. and 25° C. In some embodiments, the formulation comprises rhC1-INH in about 150 mM glycine, about 50 mM sorbitol, about 150 mM Arg-HCl and about 50 mM sodium phosphate buffer at pH 7.1. For example, in some embodiments the formulation comprises rhC1-INH at a concentration of about 45, 50, 55, 60, 65, 70, 75, 80, 85, 90, 95, or 100 mg/mL; the glycine concentration is about 75, 80, 85, 90, 95, 100, 105, 110, 115, 120, 125, 130, 135, 140, 145, 150, 155, 160, 165, 170, 175, 180, 190, 195, or 200 mM; the sorbitol concentration is about 20, 25, 30, 35, 40, 45, 50, 55, 60, 65, 70, 75, or 80 mM; the Arg-HCL concentration is about 75, 80, 85, 90, 95, 100, 105, 110, 115, 120, 125, 130, 135, 140, 145, 150, 155, 160, 165, 170, 175, 180, 190, 195, or 200 mM; the sodium phosphate concentration is about 20, 25, 30, 35, 40, 45, 50, 55, 60, 65, 70, 75, or 80 mM; the pH of the sodium phosphate buffer is about 6.5, 6.6, 6.7, 6.8, 6.9, 7.0, 7.1, 7.2, 7.3, 7.4, 7.5, 7.6, 7.7, 7.8, 7.9, or 8.0.

The formulations may be liquid, or may be lyophilized and reconstituted prior to administration.

Routes of Administration

An rhC1-INH protein described herein (or a composition or medicament containing an rhC1-INH protein described herein) is administered by any appropriate route. In some embodiments, an rhC1-INH protein or a pharmaceutical composition containing the same is administered systemically. Systemic administration may be intravenous, intradermal, intracranial, intrathecal, inhalation, transdermal (topical), intraocular, intramuscular, subcutaneous, intramuscular, oral, and/or transmucosal administration. In some embodiments, an rhC1-INH protein or a pharmaceutical composition containing the same is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, the thigh region, abdominal region, gluteal region, or scapular region. In some embodiments, an rhC1-INH protein or a pharmaceutical composition containing the same is administered intravenously. In some embodiments, an rhC1-INH protein or a pharmaceutical composition containing the same is administered orally. In some embodiments, an rhC1-INH protein or a pharmaceutical composition containing the same is administered intracranially. In some embodiments, an rhC1-INH protein or a pharmaceutical composition containing the same is administered intrathecally. More than one route can be used concurrently, if desired.

In some embodiments, an rhC1-INH protein or a pharmaceutical composition containing the same is administered to a subject by intrathecal administration. As used herein, the term "intrathecal administration" or "intrathecal injection" refers to an injection into the spinal canal (intrathecal space surrounding the spinal cord). Various techniques may be used including, without limitation, lateral cerebroventricular injection through a burrhole or cisternal or lumbar puncture or the like. In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between the third and fourth lumbar (lower back) vertebrae and, more inclusively, the L2-S1 region of the spine.

In some embodiments, an rhC1-INH protein or a pharmaceutical composition containing the same is administered to the subject by subcutaneous (i.e., beneath the skin) administration. For such purposes, the formulation may be injected using a syringe. However, other devices for administration of the formulation are available such as injection devices (e.g., the Inject-ease™ and Genject™ devices); injector pens (such as the GenPen™); needleless devices (e.g., MediJector™ and BioJector™); and subcutaneous patch delivery systems.

In some embodiments, intrathecal administration may be used in conjunction with other routes of administration (e.g., intravenous, subcutaneously, intramuscularly, parenterally, transdermally, or transmucosally (e.g., orally or nasally)).

The present invention contemplates single as well as multiple administrations of a therapeutically effective amount of an rhC1-INH protein or a pharmaceutical composition containing the same described herein. An rhC1-INH protein or a pharmaceutical composition containing the same can be administered at regular intervals, depending on the nature, severity and extent of the subject's condition (e.g., hereditary angioedema). In some embodiments, a therapeutically effective amount of an rhC1-INH protein or a pharmaceutical composition containing the same may be administered periodically at regular intervals (e.g., once every year, once every six months, once every five months, once every three months, bimonthly (once every two months), monthly (once every month), biweekly (once every two weeks), weekly, daily or continuously).

In some embodiments, administration results only in a localized effect in an individual, while in other embodiments, administration results in effects throughout multiple portions of an individual, for example, systemic effects. Typically, administration results in delivery of an rhC1-INH protein to one or more target tissues. In some embodiments, the rhC1-INH protein is delivered to one or more target tissues including, but not limited to, heart, brain, skin, blood, spinal cord, striated muscle (e.g., skeletal muscle), smooth muscle, kidney, liver, lung, and/or spleen. In some embodiments, the rhC1-INH protein is delivered to the heart. In some embodiments, the rhC1-INH protein is delivered to the central nervous system, particularly the brain and/or spinal cord. In some embodiments, the rhC1-INH protein is delivered to triceps, tibialis anterior, soleus, gastrocnemius, biceps, trapezius, deltoids, quadriceps, and/or diaphragm.

Dosage Forms and Dosing Regimen

In some embodiments, a composition is administered in a therapeutically effective amount and/or according to a dosing regimen that is correlated with a particular desired outcome (e.g., with prophylaxis of a complement-mediated chronic disease, such as HAE).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, severity of cardiac defect and/or level of risk of cardiac defect, etc., or combinations thereof). Such doses or amounts can be determined by those of ordinary skill. In some embodiments, an appropriate dose or amount is determined in accordance with standard clinical techniques. Alternatively or additionally, in some embodiments, an appropriate dose or amount is determined through use of one or more in vitro or in vivo assays to help identify desirable or optimal dosage ranges or amounts to be administered.

In various embodiments, an rhC1-INH protein is administered at a therapeutically effective amount. Generally, a therapeutically effective amount is sufficient to achieve a meaningful benefit to the subject (e.g., prophylaxis, treating, modulating, curing, preventing and/or ameliorating the underlying disease or condition). Generally, the amount of a therapeutic agent (e.g., an rhC1-INH protein) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges. In some particular embodiments, appropriate doses or amounts to be administered may be extrapolated from dose-response curves derived from in vitro or animal model test systems.

In some embodiments, a composition is provided as a pharmaceutical formulation. In some embodiments, a pharmaceutical formulation is or comprises a unit dose amount for administration in accordance with a dosing regimen correlated with achievement of the reduced incidence or risk of an HAE attack.

In some embodiments, a formulation comprising an rhC1-INH protein described herein administered as a single dose. In some embodiments, a formulation comprising an rhC1-INH protein described herein is administered at regular intervals. Administration at an "interval," as used herein, indicates that the therapeutically effective amount is administered periodically (as distinguished from a one-time dose). The interval can be determined by standard clinical techniques. In some embodiments, a formulation comprising an rhC1-INH protein described herein is administered bimonthly, monthly, twice monthly, triweekly, biweekly, weekly, twice weekly, thrice weekly, daily, twice daily, or every six hours. The administration interval for a single individual need not be a fixed interval, but can be varied over time, depending on the needs of the individual.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific protein employed; the duration of the treatment; and like factors as is well known in the medical arts.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

In some embodiments, a formulation comprising an rhC1-INH protein described herein is administered at regular intervals indefinitely. In some embodiments, a formulation comprising an rhC1-INH protein described herein is administered at regular intervals for a defined period.

It is to be further understood that for any particular subject, specific dosage regimens should be adjusted over time according to the individual need and the professional judgment of the person administering or supervising the administration of the enzyme replacement therapy and that dosage ranges set forth herein are exemplary only and are not intended to limit the scope or practice of the claimed invention.

Combination Therapy

In some embodiments, an rhC1-INH protein is administered in combination with one or more known therapeutic agents (e.g., corticosteroids) currently used for treatment of a complement-mediated disease. In some embodiments, the known therapeutic agent(s) is/are administered according to its standard or approved dosing regimen and/or schedule. In some embodiments, the known therapeutic agent(s) is/are administered according to a regimen that is altered as compared with its standard or approved dosing regimen and/or schedule. In some embodiments, such an altered regimen differs from the standard or approved dosing regimen in that one or more unit doses is altered (e.g., reduced or increased) in amount, and/or in that dosing is altered in frequency (e.g., in that one or more intervals between unit doses is expanded, resulting in lower frequency, or is reduced, resulting in higher frequency).

Disorders

In some embodiments, the recombinant proteins provided by the invention are suitable for acute attacks associated with complement-mediated disorders, e.g., NMOSD, AMR, or HAE events. These attacks may be long or short. In some embodiments, the disease or disorder is chronic. In some embodiments the compositions and methods of the invention are used prophylactically. Exemplary complement-mediated disease that may be treated using the compositions and methods disclosed herein include, but are not limited to, hereditary angioedema, antibody mediated rejection, neuromyelitis optica spectrum disorders, traumatic brain injury, spinal cord injury, ischemic brain injury, burn injury, toxic epidermal necrolysis, multiple sclerosis, amyotrophic lateral sclerosis (ALS), Parkinson's disease, stroke, chronic inflammatory demyelinating polyneuropathy (CIDP), myasthenia gravis, multifocal motor neuropathy.

EXAMPLES

Other features, objects, and advantages of the present invention are apparent in the examples that follow. It should be understood, however, that the examples, while indicating embodiments of the present invention, are given by way of illustration only, not limitation. Various changes and modifications within the scope of the invention will become apparent to those skilled in the art from the examples.

Example 1: Transient Expression of Recombinant Human C1-INH

The amino acid sequence of human plasma derived C1-INH was used to create a CHO-optimized nucleotide sequence. This sequence was then inserted into a pXLG6 expression vector and transfected into CHO cells.

Two different methods of transfection (HD1 and HD2) and two different culture temperatures (31° C. and 37° C.) were tested. For both HD1 and HD2, on the day of transfection, the cells were passaged into fresh Growth Medium and a mixture of Polyethyleneimine Linear MW 25,000 (PEI) and DNA was added to the cells. All of the transfections showed good viability and good transfection efficiency. C1-INH activity and antigen ELISA assays were used to determine the titers of active protein in cell culture supernatant.

C1 inhibitor was expressed at high levels (>200 mg/L) for all conditions tested. The combination of HD2 and Feed unexpectedly resulted in very high expression levels (>600 mg/L). At 37° C., this condition can reach more than 1000 mg/L by day 5, which is surprisingly high considering the short time frame available for the expression. At 31° C., the observed titers are generally lower but still above 600 mg/L.

Example 2: Establishment of Stable Clones Producing C1-Inhibitor

A CHO cell line adapted to suspension culture and serum free growth conditions was used as the parent cell line to generate and develop cell lines stably expressing recombinant human C1-INH.

The parental CHO cell line was transfected with pXLG6-C1-INH by chemical transfection using both HD1 and HD2. Recombinant cell pools were selected over several days with puromycin and tested for their rhC1-INH expression levels. Clonal populations were then generated by limiting dilutions of the pools. Pool Nos. 1 and 12 were chosen for use in producing clonal cell lines due to the combination of high expression level and high Activity/Antigen ratios.

Starting from Pool Nos. 1 and 12, single cell cloning was performed using a limiting dilution method in 96-well plates. Cell density, viability, and productivity were measured on a regular basis. Clone Nos. 1 and 31 were selected for further development based on high productivity, quality of rhC1-INH expressed, and stability.

Example 3: Cell Culture Optimization

To identify a robust combination of clone/medium, e.g., high volumetric productivity and desired degree of sialylation, for the development of a scalable production process, a media screening study of 40 commercial media was performed using Clone Nos. 1 and 31.

Depending on the cultivation medium used, Clone No. 1 was able to produce about 1000-1200 mg/L of recombinant C1-INH, while Clone No. 31 produced about 600-800 mg/L. However, the sialylation of the C1-INH produced by Clone No. 31 appeared more similar to plasma-derived C1-INH than the C1-INH produced by Clone No. 1. Accordingly, Clone No. 31 was selected for further development.

Example 4: Medium and Feed Optimization

Four feeds were studied to evaluate their effect on cell growth and C1-INH expression. These were: Feed3, PW2, Pep1510, and Pep4601, described in Table 1. Cell viability and titers were measured on day 7 and day 10 for each condition. A mixture of Feed3 and Pep1510 (Feed3:Pep1510 (v/v)=9:1) maximized both titer and viability under the culture conditions of the experiment.

TABLE 1

Feed components

| Code | Name | Manufacturer | Cat No. | Lot No. | Note |
|---|---|---|---|---|---|
| Feed 3 | immediate ADVANTAGE | Sigma (SAFC) | 8383C | 1213297 | Contains plant hydrolysates |
| Pep1510 | HyPep 1510 | Sheffield Bioscience | 5X59053 | 1320006300 | 200 g/L in water |
| Pep4601 | HyPep 4601 | Sheffield Bioscience | 5Z10419 | 70045788 | 200 g/L in water |
| PW2 | PowerFeed A | Lonza | BE02-044Q | 2MB111 | Chemically defined |
| FC | Feed C | CMC ICOS | N/A | Dec. 3, 2012 | Chemically defined |

Three media, detailed in Table 2, selected based on the results of the screening described in Example 3 were tested in combination with feeds to identify culture conditions that maximize the protein quality. The experiments were run in MaxiTubeSpin® Bioreactors (MTS) in the combinations outlined in Table 3. The cultures were monitored and supplemented to maintain adequate levels of glucose and bicarbonate.

TABLE 2

The three growth media tested with Clone No. 31.

| Code | Medium | Manufacturer | Cat No. | Lot No. |
|---|---|---|---|---|
| 22 | PowerCHO1 CD | Lonza | BE12-770Q | 0000263450; 0000293517 |
| N/A | CDCIM | CMC ICOS | N/A | #12-4821-25 (Dec. 10, 2012) |
| N/A | CDCIM + CB | CMC ICOS | N/A | Dec. 3, 2012 |

These media were tested in combination with feeds to identify culture conditions that maximize the protein quality. The experiments were run in MaxiTubeSpin® Bioreactors (MTS) under the conditions outlined in Table 3. The cultures were monitored and supplemented to maintain adequate levels of glucose and bicarbonate.

TABLE 3

Medium and feed combinations tested

| MTS | Medium | Feed |
|---|---|---|
| 1 | PowerCHO1 | No Feed |
| 2 | PowerCHO1 | No Feed |
| 3 | PowerCHO1 | Feed3 + Pep1510 (D3-33%) |
| 4 | PowerCHO1 | Feed3 + Pep1510 (D3-33%) |
| 5 | PowerCHO1 | Feed C (D3-10%, D7-10%, D9-5%, D11-5%) |
| 6 | PowerCHO1 | Feed C (D3-10%, D7-10%, D9-5%, D11-5%) |
| 7 | CDCIM | No Feed |
| 8 | CDCIM | No Feed |
| 9 | CDCIM | Feed3 + Pep1510 (D3-33%) |
| 10 | CDCIM | Feed3 + Pep1510 (D3-33%) |
| 11 | CDCIM | Feed C (D3-10%, D7-10%, D9-5%, D11-5%) |
| 12 | CDCIM | Feed C (D3-10%, D7-10%, D9-5%, D11-5%) |
| 13 | CDCIM + CB | No Feed |

TABLE 3-continued

Medium and feed combinations tested

| MTS | Medium | Feed |
|---|---|---|
| 14 | CDCIM + CB | No Feed |
| 15 | CDCIM + CB | Feed3 + Pep1510 (D3-33%) |
| 16 | CDCIM + CB | Feed3 + Pep1510 (D3-33%) |
| 17 | CDCIM + CB | Feed C (D3-10%, D7-10%, D9-5%, D11-5%) |
| 18 | CDCIM + CB | Feed C (D3-10%, D7-10%, D9-5%, D11-5%) |

On day 3, cells cultured under each condition were used to start a TubeSpin® satellite culture in order to test the effect of temperature (31° C., 34° C., and 37° C.) on protein quality and productivity. On day 10, the viable cell densities and viabilities in these satellite cultures were measured using a flow cytometer. For each condition CCS samples were taken for later analysis. The data indicated that conditions using PowerCHO 1 maximized product quantity and quality Example 5: Large-Scale Recombinant C1-Inhibitor Production A number of production runs evaluated various parameters to optimize large scale production of C1-INH by Clone No. 31. The optimal mixture for feeding the culture was found to be 9 volumes of imMEDIAte ADVANTAGE (herein referred to as "Feed3") (Sigma (SAFC), Catalog No. 8383C) for one volume of HyPep1510 (herein referred to as "Pep1510") (Sheffield Bioscience, Catalog No. 5X59053, 200 g/l in water). Using the Feed3+Pep1510 combination in conjunction with PowerCHO1 medium a yield of approximately 1.3 g/l (90% viability) on day 10 and about 2.0 g/l (87% viability) on day 14 was achieved. In order to minimize $PCO_2$ and osmolality, the pH control was HCl/carbonate. A mix of air+5% $CO_2$ was continuously sparged at 0.03 vvm and pH maintained at 7.2.

While reusing the same seeding density and pH control scheme another run of bioreactors was designed to explore the possibility of replacing Feed3, a complex, non-chemically defined feed, with PowerFeed A (herein referred to as "PW2"), (Lonza, Catalog No. BE02-044Q), a chemically defined feed. For all reactors a seeding density of $0.5 \times 10^6$ cells/ml was used. Surprisingly, as shown in Table 4, the production titer results obtained using PW2 were far below expectations.

TABLE 4

Comparison Feed3 and PW2 productivity.

| Feed type | Feed3 + Pep1510 | PW2 + Pep1510 |
|---|---|---|
| Set-Up | | |
| Starting volume | 1 L | 1 L |
| Temperature | 37° C. | 37° C. |
| pH | 7.2 | 7.2 |
| Feed volume | 1/3rd of final volume | 1/3rd of final volume |
| Performance | | |
| Maximum cell density | $4.9 \times 10^6$ cells/ml | $4.2 \times 10^6$ cells/ml |
| Titer on Day 10 | 1301 mg/l | 314 mg/l |
| Viability on Day 10 | 94% | 89% |

Two other tested medium/feed combinations produced good results: CDCIM/(Balanced Feed+Feed Supplement): 1.2 g/l (94% viability) on day 10 and 2.6 g/l (92% viability) on day 14 and CDCIM+CB/Feed C: 1.0 g/l (98% viability) on day 10 and 2.0 g/l (82% viability) on day 14.

On the whole, all conditions performed extremely well. Higher cell densities were obtained when using Cell Boost and Feed C while the highest titers were achieved—at the end of the 14 days—without Cell Boost and with Balanced Feed. On day 10, the differences in titers were not significant. Thus, for a 1 g/L process, both processes could be used.

Overall, the data generated demonstrated that an exemplary cell line of the invention can produce, in a well optimized fed-batch process, yields for the C1 Inhibitor exceeding the 2 g/liter level. Importantly, as demonstrated by the examples below, the high titer cell culture process was achieved while maintaining the desired product quality attributes: in particular the required sialyation to achieve a half-life similar to or longer than plasma derived human C1-INH.

Example 6: Purification of Recombinant C1-Inhibitor

Figure 2:
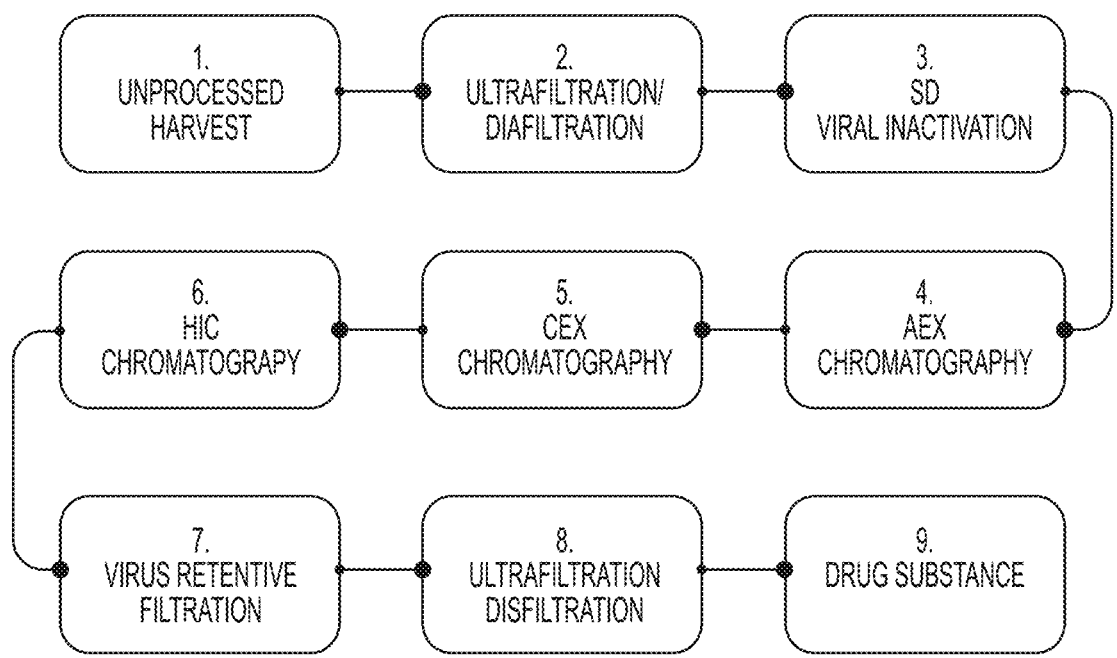
FIG. 2 is a schematic representation of the downstream process flow for rhC1-INH purification.

A process for purifying rhC1-INH expressed by cells can include concentration of the harvest, followed by viral inactivation of the concentrated harvest using solvent detergent treatment (SD), three chromatographic downstream purification steps, a viral filter reduction step, and a final concentration/diafiltration step. FIG. 2 depicts an exemplary process for rhC1-INH purification.

Exemplary chromatography operating parameters for the AEX chromatography using Gigacap Q are provided below in Table 5.

TABLE 5

Exemplary chromatography operating parameters.

| Parameter | | |
|---|---|---|
| Resin | Gigacap Q | |
| Bed Height | 7.4 cm | |
| Column Volume | 28.1 mL | |
| Flow Rate | 120 cm/hr | |
| Estimate Loading | 36 g/L | |
| Segment | Buffer | CV |
| Equilibration | 20 mM Tris, 50 mM NaCl, pH 7.5 | 3 |
| Load | Concentrated Harvest Fluid | 6 |
| EQ Wash | 20 mM Tris, 50 mM NaCl, pH 7.5 | 3 |
| Wash | 50 mM Phosphate, pH 7.0 | 5 |
| Elution | Gradient: 50 mM Phosphate, pH 7.0/50 mM Phosphate, 0.3M NaCl, pH 7.0 | 10 |

Figure 3:
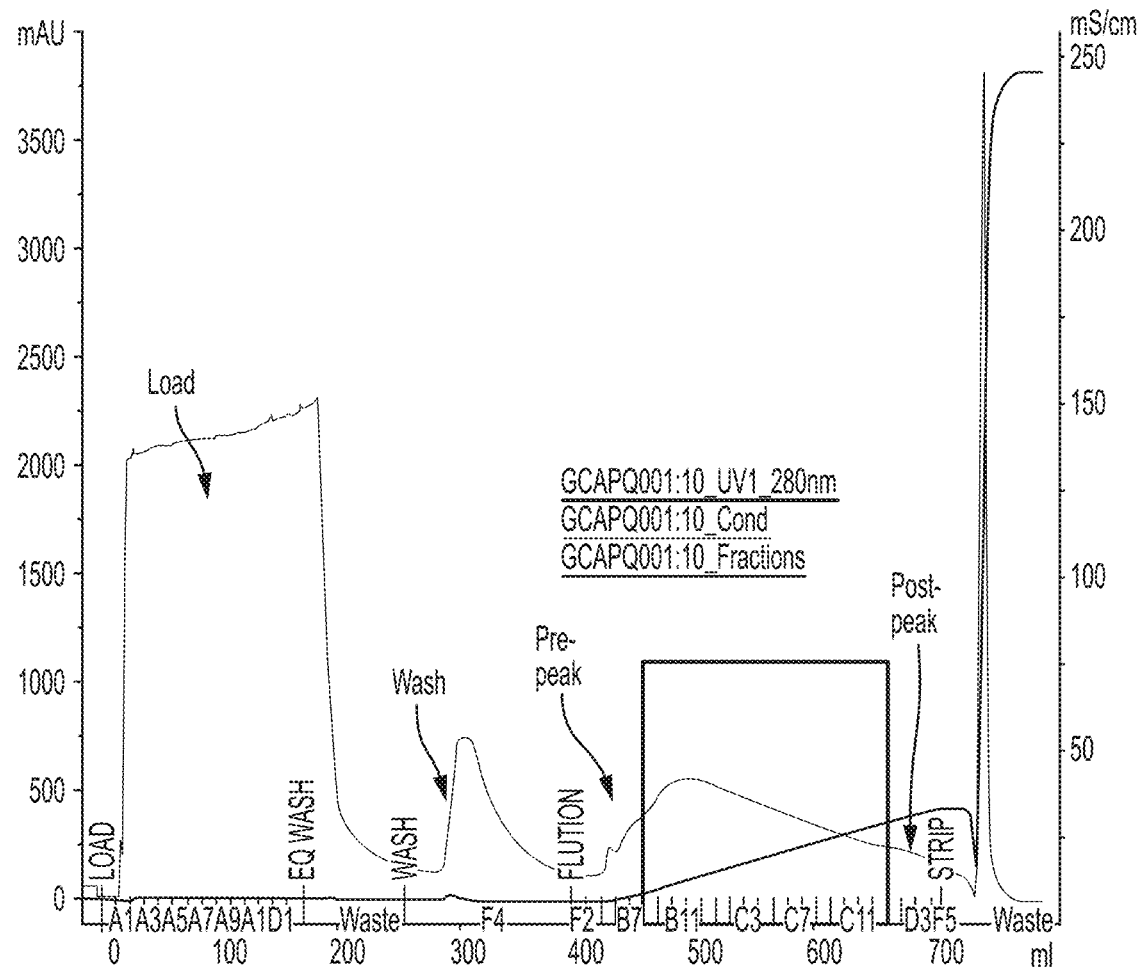
FIG. 3 depicts an exemplary Gigacap Q elution profile along with the corresponding separation of neutral and sialylated species.
Figure 4:
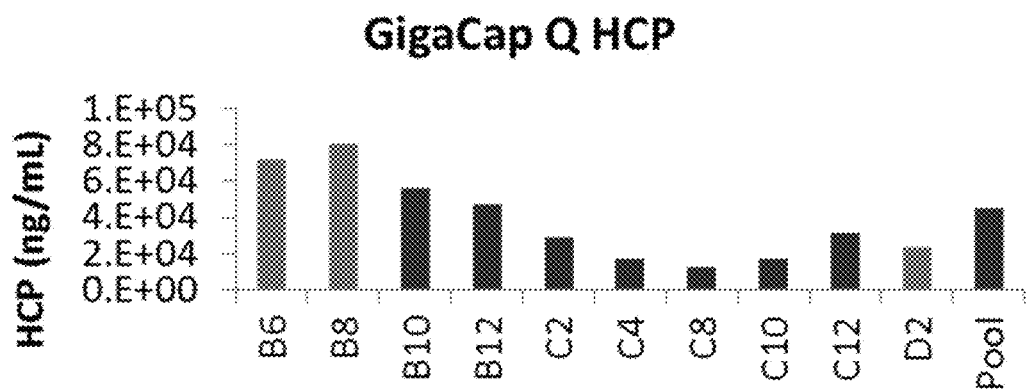
FIG. 4 depicts the ability of the anion exchange chromatography step to separate process impurities such as Host Cell Proteins (HCP).

The defined chromatography conditions are designed to enhance product quality by removing process impurities and enriching sialylated glycans. An example elution profile is shown in FIG. 3 along with the corresponding separation of neutral and sialylated species (Table 6). In addition, as shown in FIG. 4, the developed anion exchange step is able to separate process impurities such as Host Cell Proteins (HCP).

TABLE 6

Table describing exemplary separation of neutral and sialylated species

| Sample Name | 0 SA | 1 SA | 2 SA | 3 SA | 4 SA |
|---|---|---|---|---|---|
| GcapQ B6 | 28.89% | 30.82% | 24.66% | 11.36% | 4.27% |
| GcapQ B8 | 20.46% | 29.89% | 29.37% | 14.60% | 5.68% |
| GcapQ B10 | 15.56% | 27.88% | 32.68% | 17.08% | 6.80% |
| GcapQ B12 | 11.88% | 25.42% | 35.55% | 19.50% | 7.65% |
| GcapQ C2 | 9.00% | 22.65% | 37.69% | 21.51% | 9.15% |
| GcapQ C4 | 7.11% | 20.52% | 40.58% | 21.06% | 10.72% |
| GcapQ C6 | 5.72% | 17.76% | 40.21% | 24.66% | 11.64% |
| GcapQ C8 | 5.18% | 15.99% | 40.29% | 25.32% | 13.22% |
| GcapQ C10 | 5.90% | 14.96% | 39.11% | 25.02% | 15.01% |
| GcapQ C12 | 9.26% | 15.83% | 36.17% | 23.28% | 15.46% |
| GcapQ Pool | 10.05% | 21.97% | 36.87% | 21.32% | 9.79% |

Chromatography operating parameters for optimizing product quality using Cation chromatography using POROS XS are provided below in Table 7.

TABLE 7

Chromatography operating parameters.

| Parameter | | |
|---|---|---|
| Resin | POROS XS | |
| Bed Height | 14.2 cm | |
| Column Volume | 54 mL | |
| Flow Rate | 120 cm/hr | |
| Estimate Loading | 10.3 g/L | |
| Segment | Buffer | CV |
| Equilibration | 20 mM BisTris, 30 mM NaCl, pH 6.0 | 5 |
| Load | Gigacap Q Elution | 13 |
| EQ Wash | 20 mM BisTris, 30 mM NaCl, pH 6.0 | 3 |
| Elution | Gradient: 20 mM BisTris, 30 mM NaCl, pH 6.00/20 mM BisTris, 0.3M NaCl, pH 6.0 | 10 |
| Strip | 20 mM BisTris, 1M NaCl, pH 6.0 | 3 |

Figure 5:
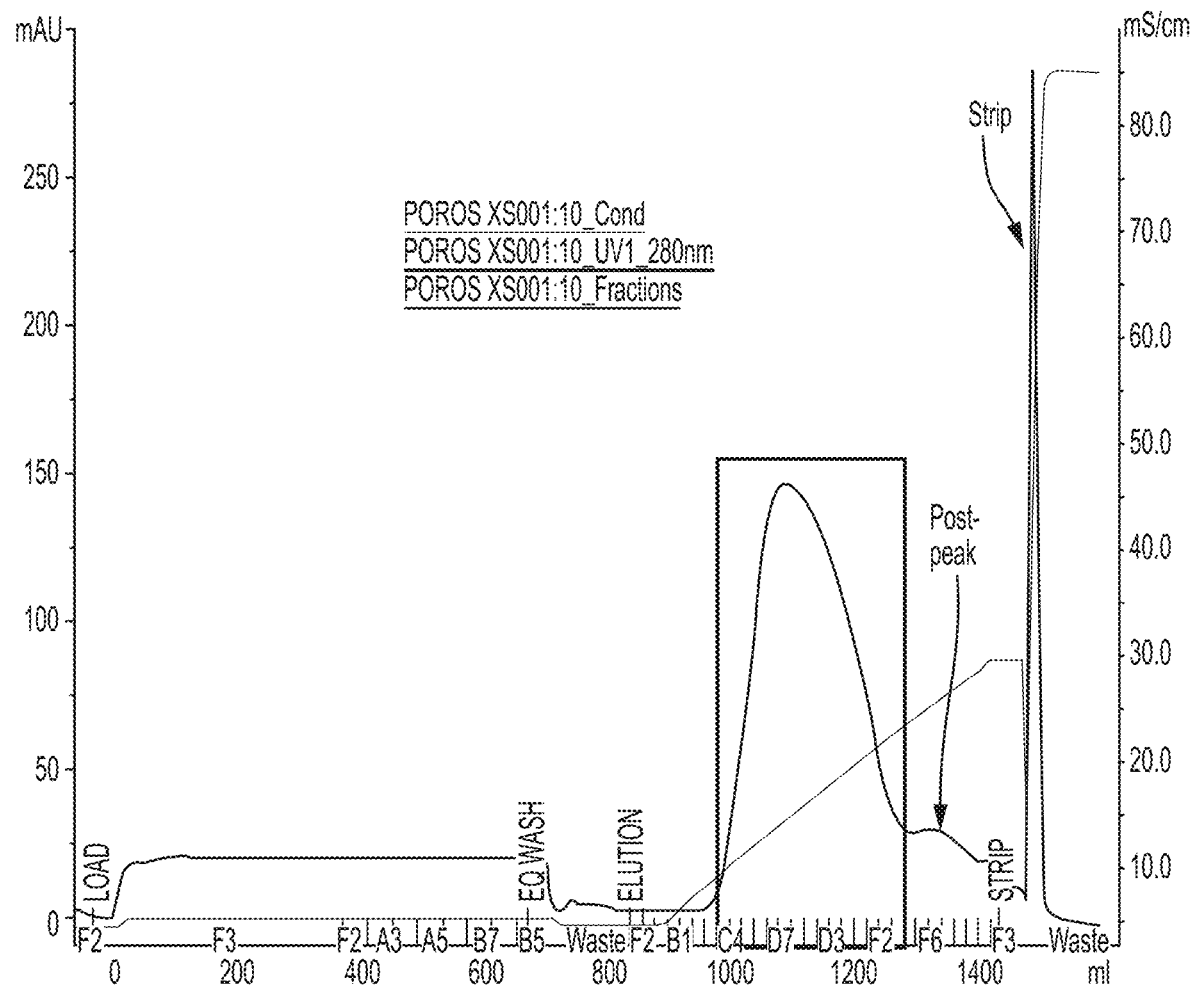
FIG. 5 depicts an exemplary Poros XS elution profile demonstrating the enrichment of the desired sialylated glycan species.
Figure 6:
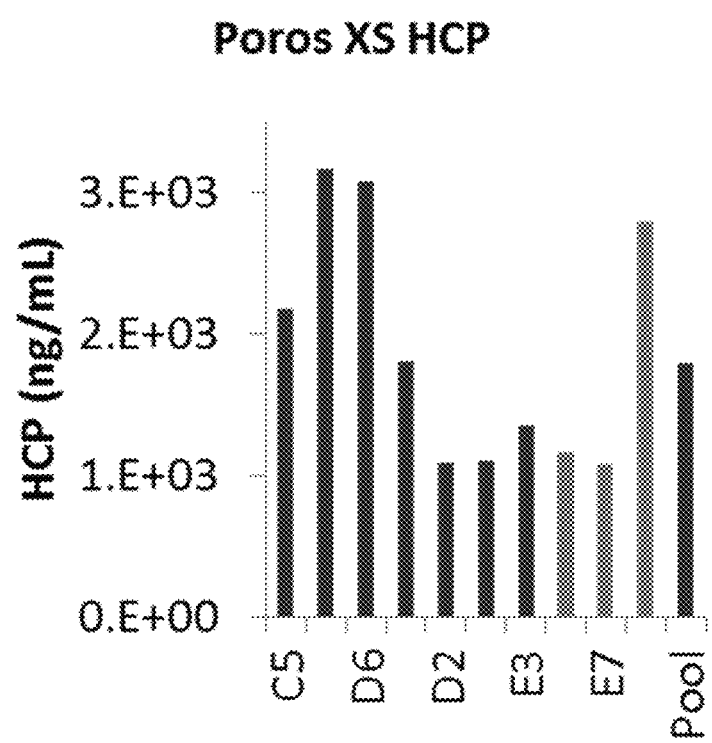
FIG. 6 shows the reduction of HCP content following Poros XS elution

The defined operating conditions are designed to enhance product quality by removing product contaminants and enriching the desired glycosylation profile. Reduction of HCP content following Poros XS elution as shown in FIG. 6. FIG. 5 depicts an exemplary Poros XS elution profile demonstrating the enrichment of the desired sialylated glycan species. Enrichment of the desired sialylated glycan species by Poros XS is shown in Table 8.

TABLE 8

Enrichment of the desired sialylated glycan species by Poros XS.

| Sample Name | 0 SA | 1 SA | 2 SA | 3 SA | 4 SA |
|---|---|---|---|---|---|
| POROS XS Fr. C7 | 3.11% | 13.61% | 40.86% | 29.43% | 12.99% |
| POROS XS Fr. D6 | 3.53% | 16.41% | 41.49% | 27.06% | 11.52% |
| POROS XS Fr. D4 | 6.19% | 21.78% | 39.59% | 23.05% | 9.40% |
| POROS XS Fr. D2 | 10.94% | 26.15% | 35.81% | 19.29% | 7.81% |
| POROS XS Fr. E1 | 17.68% | 29.93% | 31.19% | 15.26% | 5.93% |
| POROS XS pool | 8.45% | 21.40% | 37.34% | 22.82% | 10.00% |

Example 7: Glycan Analysis of Recombinant C1-Inhibitor

Approximately 50% of the intact molecular weight of C1-INH is glycan. There are six (6) N-linked sites (three in the serpin domain (Asn216, Asn231, Asn330) and 3 in the N-terminal domain (Asn3, Asn47, Asn59) and eight (8) O-linked sites, all in the N-terminal domain (Ser42, Thr25, Thr26, Thr49, Thr61, Thr66, Thr70, Thr74).

Several analytical methods were developed and/or evaluated to characterize the N-glycan and O-glycan distribution on recombinant C1-Inhibitor expressed by CHO cells according to the methods described herein. A commercially available plasma-derived human C1-INH was also run as a comparator. These methods are exemplary methods for analyzing glycosylation and are not intended to be limiting in any way.

Each method required the pre-assay steps of removal of glycans from the protein, derivatization of glycans with a fluorophore, e.g., 2-aminobenzoic acid (2-AA), removal of excess derivatization reagents by solid phase extraction, and characterization of the resulting labeled glycans.

1. N-Glycan Analysis by Mixed-Mode Normal Phase/Anion Exchange HPLC (NP/AE)

Figure 7:
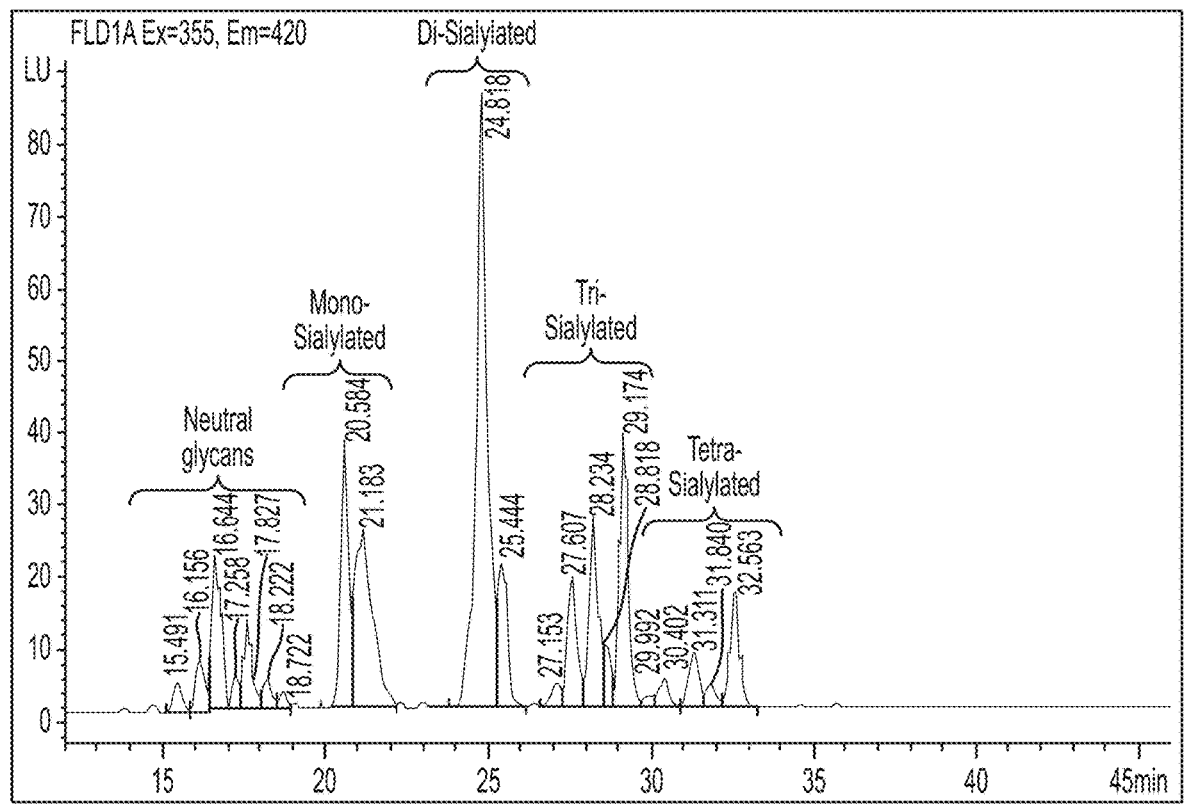
FIG. 7 depicts an example of sample integration for NGA-NP/AE of an rhC1-INH.
Figure 8:
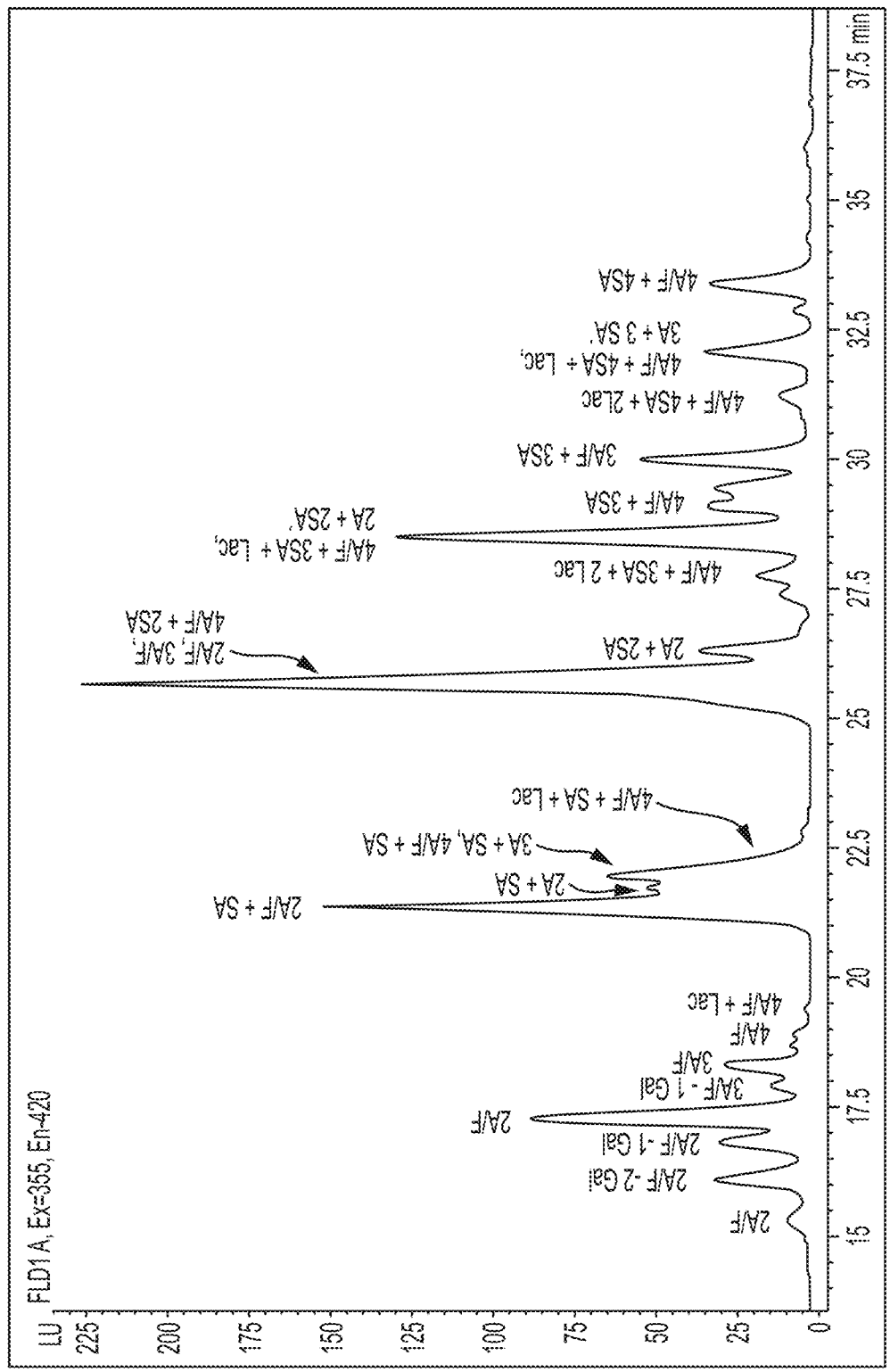
FIG. 8 depicts a labeled mixed-mode chromatogram, with peaks identified from MALDI-TOF MS analysis of a HPLC-fractionated glycan pool from an rhC1-INH.

N-glycan analysis (NGA) using mixed-mode normal phase/anion exchange chromatography (NP/AE) was used to provide a profile of the N-linked glycan content of rhC1-INH, by separation of the labeled glycans based primarily upon charge (due to sialic acid content), but also by size, oligosaccharide composition, and linkages. Eluted peaks were grouped roughly into "charge clusters" based upon sialic acid content, while peaks within the charge cluster vary in size, oligosaccharide composition, or linkages. Gradient separations were performed using a high performance liquid chromatography (HPLC) system equipped with a fluorescence detector. Integration of the resulting chromatogram allowed for reproducible quantitation of the relative N-glycan distribution, based upon sialic acid content. FIG. 7 presents an example profile for rhC1-INH, with the peak groups labeled based on sialic acid content. The identity of the peak groups observed was confirmed by off-line MALDI-TOF mass spectrometry of collected peak fractions (FIG. 8).

Figure 9:
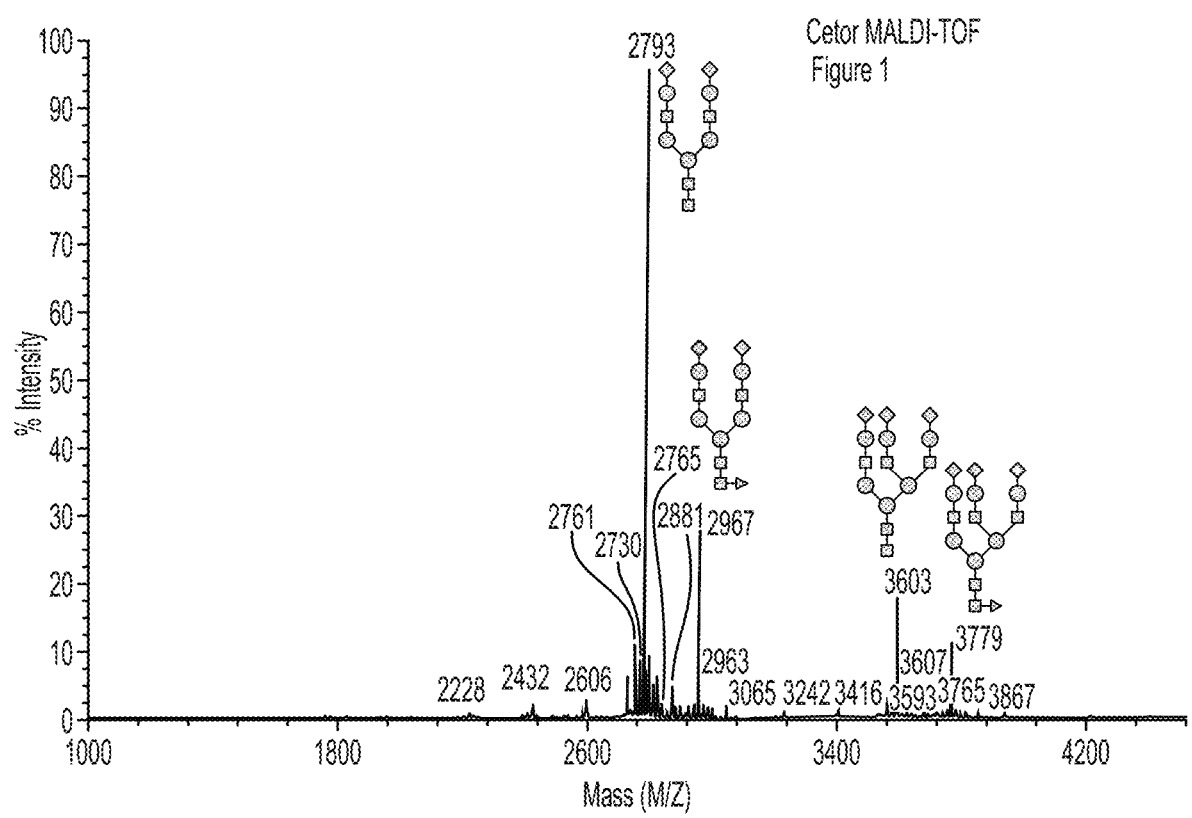
FIG. 9 depicts the glycan profile for plasma derived C1-INH.

For comparison the glycan profile for plasma derived C1-INH is shown in FIG. 9.

2. N-Glycan Analysis by Hydrophilic Interaction HPLC (HILIC)

N-glycan analysis (NGA) using Hydrophilic Interaction Liquid Chromatography (NGA-HILIC) provided a high resolution profile of the N-linked glycan content of C36, based primarily on glycan size, but also based on monosaccharide content and linkage. Gradient separations were performed using a high performance liquid chromatography system equipped with a fluorescence detector. Integration of the resulting chromatogram allowed for reproducible quantitation of relative N-glycan distribution.

Figure 10:
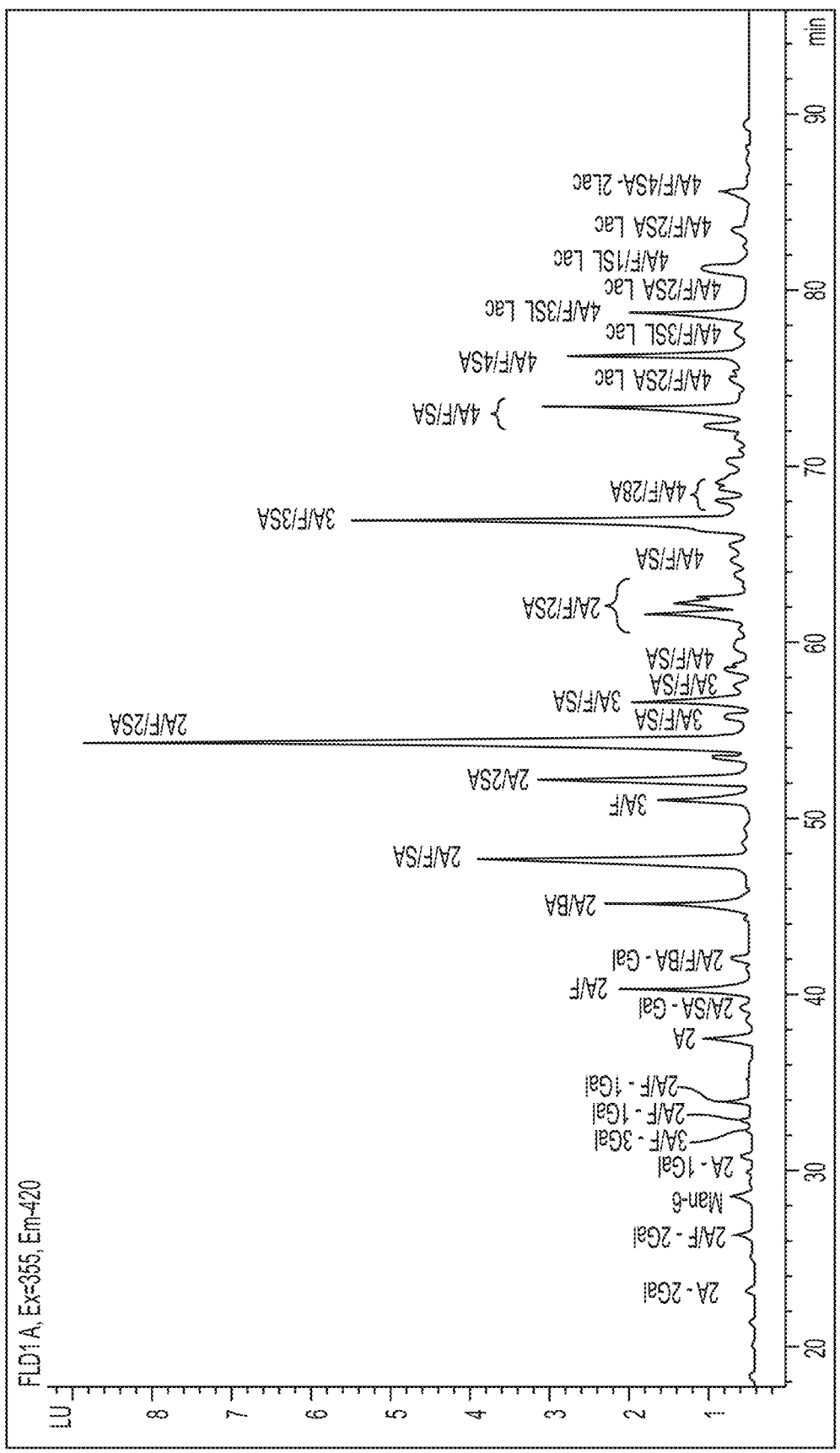
FIG. 10 shows a chromatogram for the HILIC analysis of the N-glycans of an exemplary rhC1-INH. Labeled peaks were identified by on-line LC/MS.

FIG. 10 presents a representative rhC1-INH HILIC chromatogram with peak identities obtained from on-line LC/MS evaluation. The baseline-resolved nature of the chromatogram allows calculation of the relative levels of different glycan attributes such as fucosylation, antennarity, sialylation, and terminal galactose levels.

The results obtained from NGA by mixed mode chromatography and HILIC were similar for glycans with 1 to 4 sialic acids.

3. N and O Glycan Analysis by Hydrophilic Interaction HPLC (HILIC)

O-glycan analysis was performed using ORELA release reagent (Ludger Ltd.). Chemical glycan release using the ORELA reagent results in a glycan sample composed of both asparagine-linked (N-linked) and serine/threonine-linked (O-linked) glycans. The analysis of a test sample generated with the ORELA reagent is compared with a sample generated using PNGase F, such that the total glycan profile may be compared with the N-linked-(only) glycan profile. The additional glycan peaks therefore represent the contribution from the O-linked glycosylation sites on rhC1-INH. This analysis is performed using hydrophilic interaction chromatography (HILIC).

The HILIC chromatography method allows for separation of the labeled glycans based primarily upon size, but also by monosaccharide content and linkage. As a result, the most commonly observed O-linked glycans should elute early in the chromatogram and should not co-elute with N-linked glycans. This method utilizes a UPLC column with a 1.7 µm particle size. Gradient separations may be performed using either an HPLC or UPLC system equipped with a fluorescence detector.

New peaks observed in the ORELA sample will represent O-linked glycans, which may be identified using either on-line negative-ion liquid chromatography/mass spectrometry (LC/MS) or collected and subjected to off-line matrix assisted laser desorption ionization-time of flight (MALDI-TOF) mass spectrometry.

Figure 11:
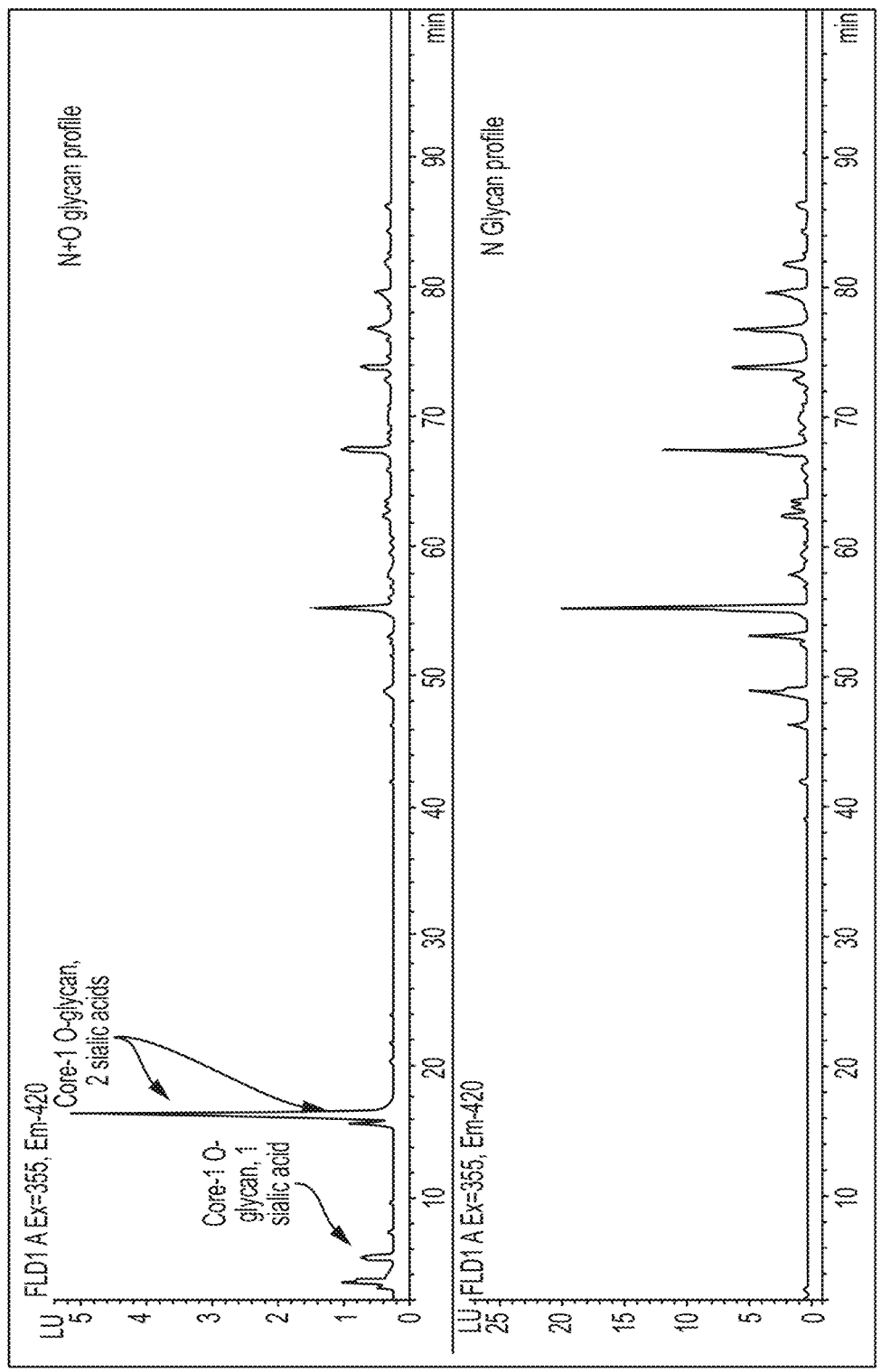
FIG. 11 presents the profiles obtained for the N-glycan profile (PNGase-F) and the N+O-glycan profile (ORELA deglycosylation) of an rhC1-INH.
Figure 12:
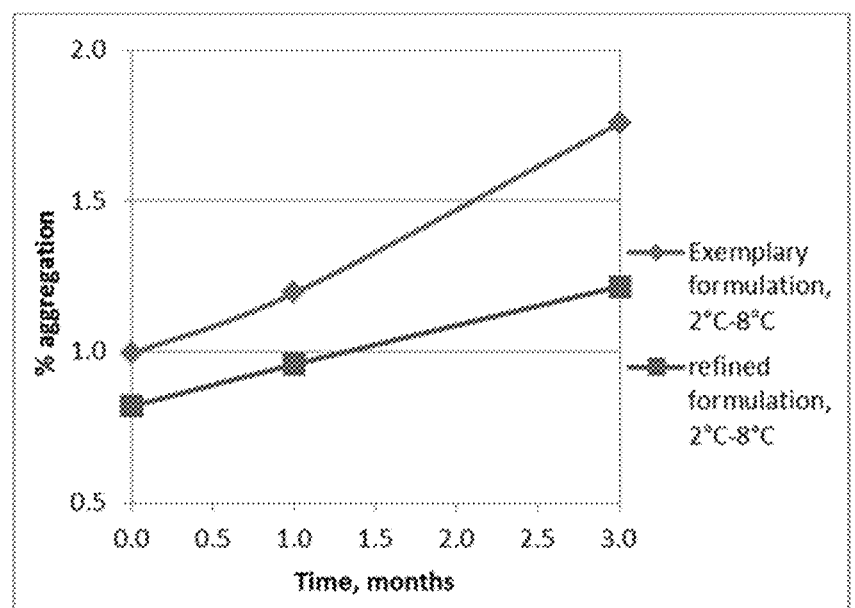
FIG. 12 is a series of graphs that indicate the stability of an rhC1-INH formulation at 2° C.-8° C. (panel A), and at 25° C. (panel B).
Figure 12:
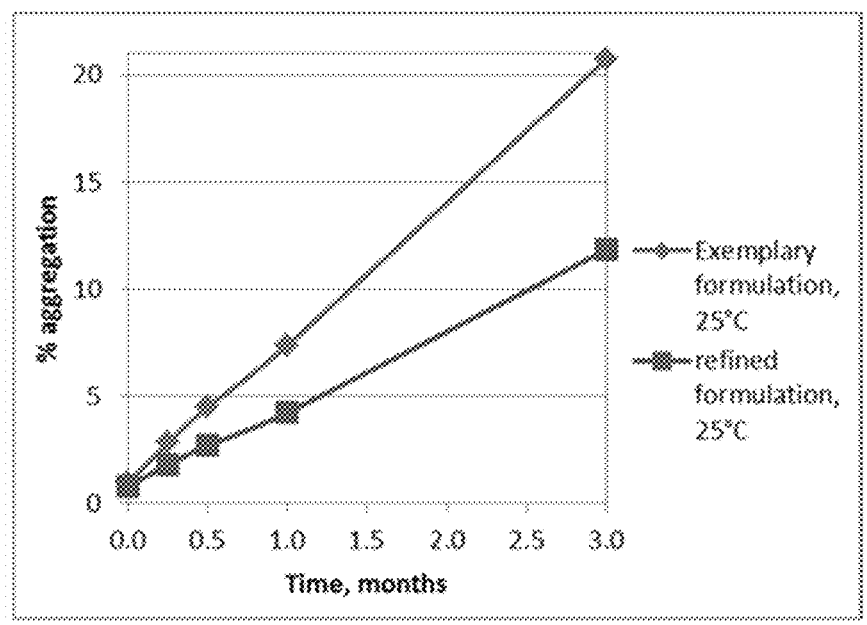

Release of the N- and O-linked glycans was performed using the ORELA release reagent, as described above. The derivatization of N- and O-linked glycans was performed using 2-AA as the fluorescent label. Evaluation of the N-linked glycan profile, with deglycosylation of N-linked glycans by PNGase-F digestion was performed for a comparison of chromatographic profiles. FIG. 11 presents the profiles obtained for the N-glycan profile (PNGase-F) and the N+O-glycan profile (ORELA deglycosylation) for a representative rhC1-INH sample. As shown in FIG. 11, a significant new peak was observed at a retention time of 16 minutes and a smaller peak at about 5 minutes. Additional peaks were observed eluting later which matched the retention times of glycans observed in the N-linked profile.

Evaluation of the identity of the new peaks was performed using on-line LC/MS analysis in negative ion mode. The results from this analysis confirmed the identification of the new peaks as Core-1 O-glycans with either 1 or 2 sialic acids (Core-1=N-acetylhexosamine+hexose (HexNAC/Hex)). It is notable that the Core-1 O-glycan with two sialic acids was observed in two peaks. The reason for this is undetermined, but may be related to differences in linkage between the glycan components. The results observed in the N+O-glycan analysis are in agreement with observations from peptide mapping of rhC1-INH after desialylation, where glycopeptides with expected O-glycosylation were observed as the HexNAC/Hex-modified form.

Example 8: Structural Analysis of rhC1-INH

The structure of an exemplary rhC1-INH protein was characterized using a variety of physiochemical methods. Primary structure and post-translational modifications were evaluated by peptide mapping LCMS, MS/MS of de-N-glycosylated rhC1-INH. The method confirmed the predicted amino acid sequence, which includes a single amino acid difference from wild-type C1-INH (E165Q). O-linked glycans were identified by this method and confirmed orthogonally via LC based glycan mapping.

Additional methods were employed to evaluate glycosylation, sialylation, and overall charge distribution. rhC1-INH glycans were shown to consist primarily of complex N-linked glycans and di- and tri-sialylated Core-1 O-linked structures through glycan mapping on the released N- and O-glycans. The analysis also shows that there were no potentially immunogenic α-galactose structures present. High levels of N-acetylneuraminic acid (NANA) were confirmed with a sialic acid content assay, and these data are consistent with the observed glycan profiles and pI distribution. The overall carbohydrate assessment also aligns with the intact mass evaluation, indicating a high degree of glycosylation on the molecule.

The average intact mass was determined by MALDI-MS, and the result was compared to the theoretical mass of the unmodified polypeptide. The difference between the theoretical and measured mass represents the carbohydrate content and is consistent with the plasma-derived C1 esterase inhibitor. The apparent molecular weight and size distribution of rhC1-INH were also investigated by SDS-PAGE and size exclusion chromatography, respectively. The higher-order structure of rhC1-INH was evaluated by DSC and was determined to be comparable to plasma derived C1 esterase inhibitor.

Recombinant C1-INH was assessed for potency using a biologically relevant enzymatic assay against the international standard and also relative to the initial development reference standard, which indicated that the recombinant molecule is fully functional. A variety of methods have been shown to be capable of monitoring these pathways. Cumulatively these studies have allowed for the elucidation of rhC1-INH structure by confirming the primary structure and providing an assessment of the biological activity, glycosylation profile, post-translational modifications, and higher order structure of the molecule. Furthermore, these studies have demonstrated that while rhC1-INH has a different glycosylation structure from plasma derived C1-INH, unexpectedly, rhC1-INH exhibits similar or better activity and similar or better pharmacokinetic properties, including half-life, than plasma derived C1-INH.

Example 9: Functional Binding Assay of Recombinant C1-Inhibitor

Activity of the rhC1-INH protein may be assessed using a chromogenic diagnostic kit, such as the TECHNO-CHROM® C1-INH reagent kit (Technoclone, Vienna, Austria). This commercial diagnostics kit was re-developed into a full-curve chromogenic assay for measuring the potency of rhC1-INH against the international standard and also relative to a reference standard.

The potency of an exemplary rhC1-INH drug substance lot was determined to be 7.2 U/mg, with a potency relative to the initial development reference standard of 121%. This chromogenic C1 esterase inhibition assay was also used to determine the potency of rhC1-INH in various samples taken from production runs and forced degradation studies described herein. Plasma derived C1-INH has been observed to have a mid-point specific activity of about 7 U/mg. The specific activity of various lots of rhC1-INH ranged from 7.1 to 7.3 U/mg. No significant difference in specific activity values for lots of rhC1-INH as compared to Cinryze® was observed.

Example 10: Formulation and Stability of Recombinant C1-Inhibitor

In one embodiment, an aqueous solution containing 70 mg/mL rhC1-INH in 150 mM glycine, 50 mM sorbitol, and 50 mM sodium phosphate buffer at pH 7.1 was prepared. The protein concentration was based on the solubility and stability profile of rhC1-INH and selected to provide maximum clinical dose. The choice of 50 mM sodium phosphate at pH 7.1 was supported by stability under thermal stress. The selection of 150 mM glycine and 50 mM sorbitol was made to attain appropriate isotonicity for intravenous and subcutaneous administration, as well as, the optimal protein stability.

This exemplary formulation was demonstrated to have adequate solubility and stability of rhC1-INH for long term storage (at least 12 months) at ≤−65° C. and for use in the clinical setting of parenteral administration by either intravenous or subcutaneous injection. This exemplary formulation was also found to be stable, as established by structural and functional (e.g., potency) analyses, at room temperature for at least one month, and stable at 2° C.-8° C. for at least six months.

The rhC1-INH formulation was further refined to optimize the stability at 2° C.-8° C. and 25° C. This refined formulation contained rhC1-INH in 150 mM glycine, 50 mM sorbitol, 150 mM Arg-HCl and 50 mM sodium phosphate buffer at pH 7.1. The aggregation profile of the refined and exemplary formulations was monitored by size exclusion chromatography (SEC) at 2° C.-8° C. and 25° C. for three months. The SEC data at these storage conditions showed that the level of high molecular weight aggregates (HMW) was significantly lower in the refined formulation. (See FIG. 13).

Example 11: In Vivo Studies of rhC1-INH

Figure 13:
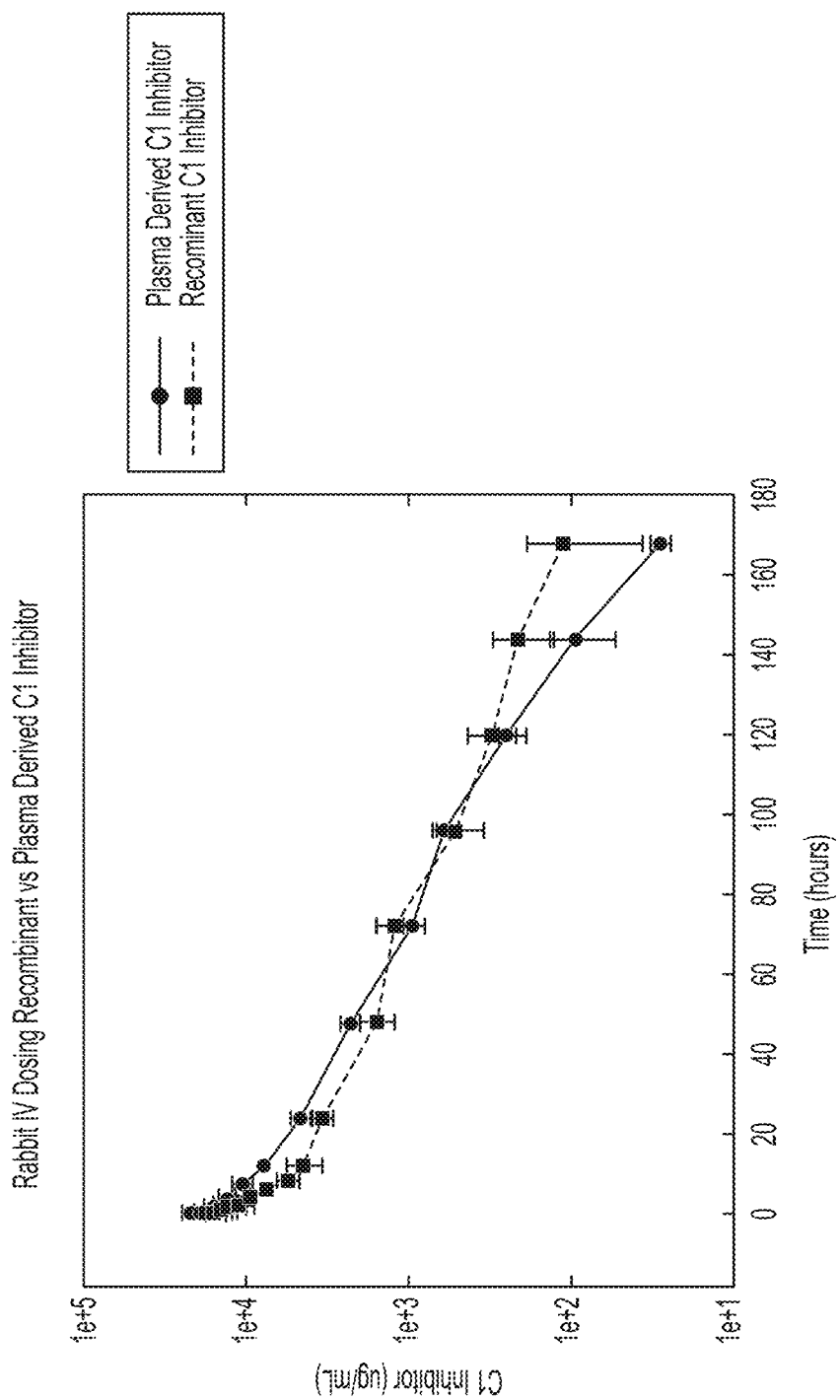
FIG. 13 shows the half-life of rhC1-INH compared with Cinryze® in rabbits.

Rabbits were injected with plasma derived C1-INH or rhC1-INH. The rhC1-INH had a glycosylation profile of 10-20% neutral glycans, about 26% mono-sialylated glycans, about 35% di-sialylated glycans, about 17% tri-sialylated glycans, and about 5% tetra-sialylated glycans. The results of the rabbit PK study are shown in FIG. 13.

Analysis of the PK data indicated that the rhC1-INH exhibited a slightly increased half-life compared to plasma derived C1-INH.

The biological potency of rhC1-INH was found to be similar to plasma derived C1-INH, as assessed by comparison of half-life and numerous complement parameters.

Accordingly, rhC1-INH is suitable for dosing in the same or similar amounts and concentrations as plasma derived C1-INH and for use in treating the same indications.

Example 12: Pre-Clinical Safety Studies

In a 14-day Rat Toxicity/TK+14-d recovery period study, rats were dosed at 500, 1000, or 2000 U/kg/day of rhC1-INH formulated as an aqueous solution containing 70 mg/mL rhC1-INH in 150 mM glycine, 50 mM sorbitol, and 50 mM sodium phosphate buffer at pH 7.1. Each group contained 10 rats. All animals survived. No rhC1-INH related effects on body weights, food consumption, or clinical pathology parameters (hematology, coagulation, serum chemistry, and urinalysis) were observed. No rhC1-INH related ophthalmic findings, macroscopic observations, alteration in organ weights, or histologic changes were observed. Anti-drug antibodies were detected but were non-neutralizing and did not impact exposure. The no observed adverse effect level (NOAEL) was 2000 U/kg/day, the highest dose tested.

In a 14-day non-human primate (NHP) Toxicity/TK+14-d recovery period study, cynomolgus monkeys were dosed at 250, 500, or 1000 U/kg/day of rhC1-INH formulated as an aqueous solution containing 70 mg/mL rhC1-INH in 150 mM glycine, 50 mM sorbitol, and 50 mM sodium phosphate buffer at pH 7.1. Each group contained 4 monkeys. All animals survived. No rhC1-INH related effects on body weight or other related clinical observations were made. No rhC1-INH related ophthalmic, electrocardiographic, macroscopic, or microscopic findings or organ weight changes were observed.

In summary the non-clinical animal data indicates that the described rhC1-INH is well tolerated and safe for evaluation in humans.

Example 13: Reduction of Contaminants

This example details the development of a contaminant (e.g. DNA and/or host cell protein) reduction step for purification of a recombinant human C1 inhibitor protein (rhC1-INH). An overview of the current downstream process is shown in FIG. 14.

Anion Exchange membrane absorbers were evaluated (Sartobind Q, Sartobind STIC, and Natrix) with regard to providing additional DNA clearance for the downstream process depicted in FIG. 14. Data are presented below that show Anion exchange (AEX) membrane absorbers (Sartobind Q and Sartobind STIC) are suitable process steps for contaminant reduction, including DNA reduction, after the third chromatography step (i.e. POROS XS (CEX)) of an rhC1-INH downstream process (see FIG. 14). Based on DNA spiking studies, detailed below, with CHO DNA, Sartobind Q had superior process yields, in comparison to Sartobind STIC. The Sartobind Q had process yields of greater than 90% and DNA clearance of greater than 4.1 log. The host cell protein clearance measured for both Sartobind Q and Sartobind STIC was minimal (<1 log).

General Materials, Methods, and Equipment
Determination of Protein Content by UV Spectrophotometry The protein concentration for all samples not containing conditioned media, was determined by using the measured absorbance at 280 nm and the extinction coefficient, $\varepsilon^{280}$=0.514 mL/(mg×cm).

TME-0499-01, Generic Chinese Hamster Ovary Cells Protein (CHOP) ELISA—3rd Generation Samples analyzed in the development process used TME-0499 to determine the amount of CHO cell protein in the samples. This method used the $3^{rd}$ generation Chinese Hamster Ovary Host Cell Protein kit manufactured by Cygnus Technologies, catalog number F550.

DNA Concentration

CHO DNA analysis was initially performed by Pico Green. This method is an ultrasensitive fluorescent nucleic acid stain. Samples that may contain dsDNA are first diluted to a final volume of 1.0 ml in TE buffer in a disposable cuvette. Dilutions of the experimental sample are performed to diminish the interfering effect of certain contaminates (e.g., NaCl). 1.0 ml of aqueous working solution of the Quant-IT PicoGreen reagent is then added to the cuvette and incubated, protected from light, for 2 to 5 minutes. The fluorescence of the sample is measured on a spectrofluorometer and standard fluorescein wavelengths (excitation ~480 nm, emission ~520 nm). Accurate quantitation is achieved by comparing the signal of the unknowns to dsDNA standards assayed at the same time. CHO DNA analysis was also performed by qPCR.

DNA Reduction Step Development

Table 9 shows historical DNA levels for process intermediates and final bulk for development of rhC1-INH. The data indicated that DNA levels were less than detectable after the first column step in the process. However, after concentration of the final bulk to up to 70 g/L, all runs had measureable levels of DNA.

Based on a typical dosing of the 70 mg/ml bulk drug substance, a target of <14 ng DNA/mg is recommended.

TABLE 9

Summary of Historical DNA Results for Process Intermediates and Final Bulk.

| Process Step | Demo Run # 2 (pg/mg) | ENGR 14-18 (pg/mg) | ENGR 14-20 (pg/mg) | GMP1/ 14-0042 (pg/mg) |
|---|---|---|---|---|
| Harvest concentrate | — | — | 3.835 | 2769 |
| GigacapQ Eluate | <22 | 37 | 6.9 | 9.5 |
| POROS XS | <11 | 8 | 77 | 1.3 |
| Octyl | <17 | <12 | <13 | 7 |
| Bulk (Target <14 pg/mg) | 5.39 | 8 | 5 | 13 |

Three anion exchange (AEX) absorbers were tested for their ability to reduce contaminants, specifically to reduce contaminating DNA. The absorbers tested were Sartobind Q, Sartobind STIC, and Natrix membrane.

POROS XS Eluate Identified as Most Suitable Position to Apply AEX Absorber

The POROS XS eluate was identified as the most suitable position to apply the AEX absorber. The POROS XS eluate, at pH 6 compared to 7.5 for the Gigacap Q eluate, was deemed more suitable as the AEX absorber load given the low pI of ~2.7-3.6 for rhC1-INH. The ideal configuration for the AEX membrane absorber is to have the rhC1-INH flow through the unit while negatively charged contaminants bind. A lower pH running condition decreased the likelihood of the protein binding to the membrane while allowing contaminants to bind. Conductivity is another reason the POROS XS eluate was selected. High load conductivity is generally not desirable for AEX membrane chromatography because it decreases the affinity of contaminants to the membrane. The POROS XS eluate conductivity is typically slightly lower than that of the GigacapQ eluate and is therefore more suitable from this perspective. Furthermore, the GigacapQ eluate is buffered with 50 mM phosphate, a divalent negatively charged buffer. High phosphate conditions are considered worst case since the high ionic strength and multiple negative charges can interfere with anion exchange chromatography.

Profile Runs for Sartobind Q, Sartobind STIC, and Natrix Membranes

Profile runs were conducted in order to determine whether an AEX absorber step could be run in flow through mode for the Sartobind Q, Sartobind STIC, and Natrix membranes.

Octyle flowthrough was used for these experiments. Octyl flowthrough was dialyzed into 20 m M Bis Tris, 30 mM NaCl, pH 6.0 and concentrated to 1 g/L. This low salt condition was used as a worst case assessment to determine whether rhC1-INH would bind under low salt conditions. Stepwise washes with increasing ionic strengths were used to identify conditions that promoted bound rhC1-INH to release. Buffer blending was used to perform the stepwise washes. Each absorber was run at the minimum load condition required for a single membrane to be used at-scale 500 L scale (e.g., >250 g rhC1-INH/L membrane for Sartobind Q and STIC, assuming 1.6 L mega size for 500 L scale).

Figure 15A:
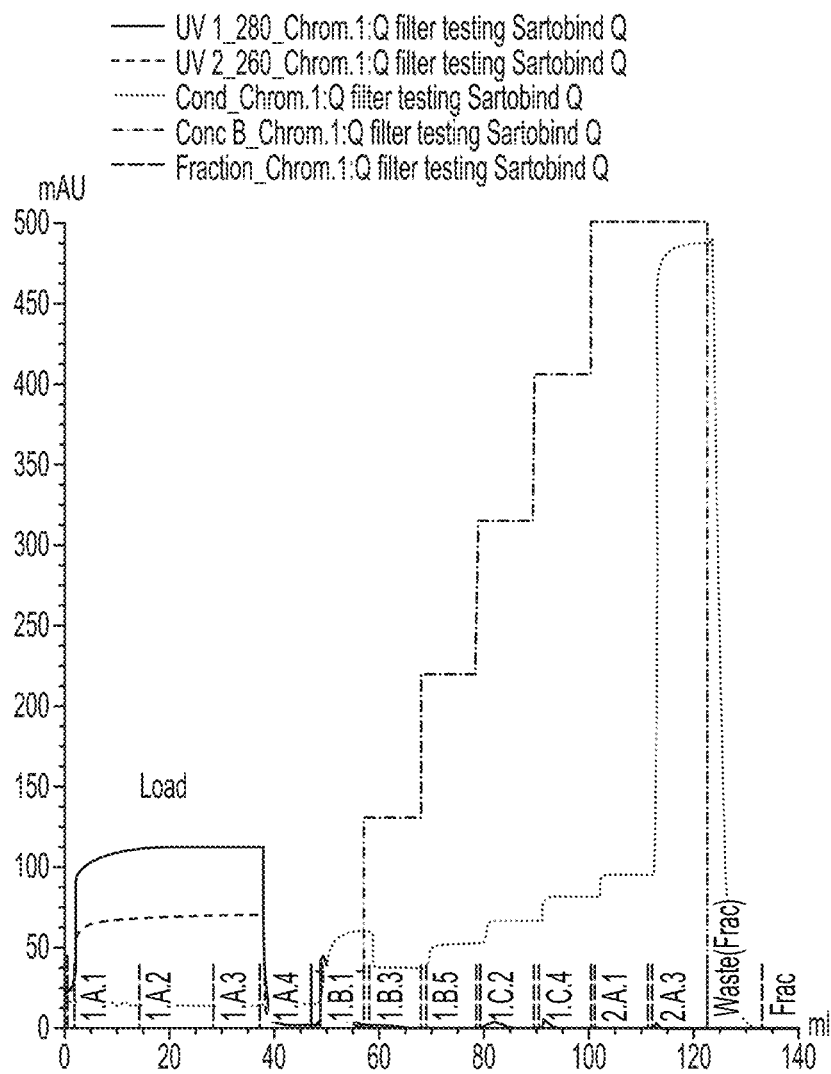
FIG. 15 depicts a series of chromatograms that show yield and associated descriptors of the following profile runs: Sartobind Q (panel A), Sartobind STIC (panel B), and Natrix (panel C).
Figure 15B:
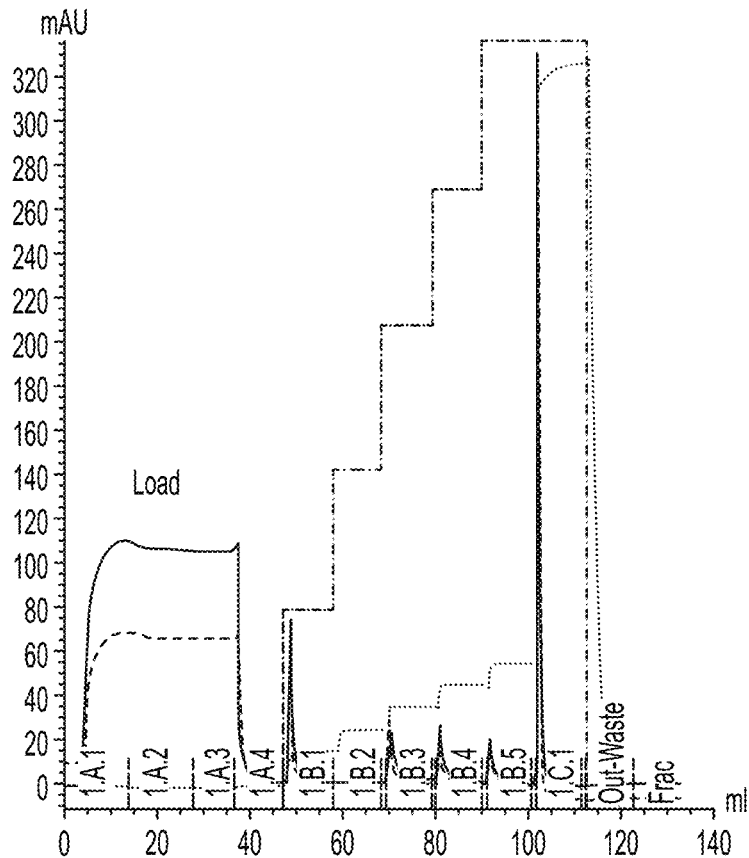
Figure 15C:
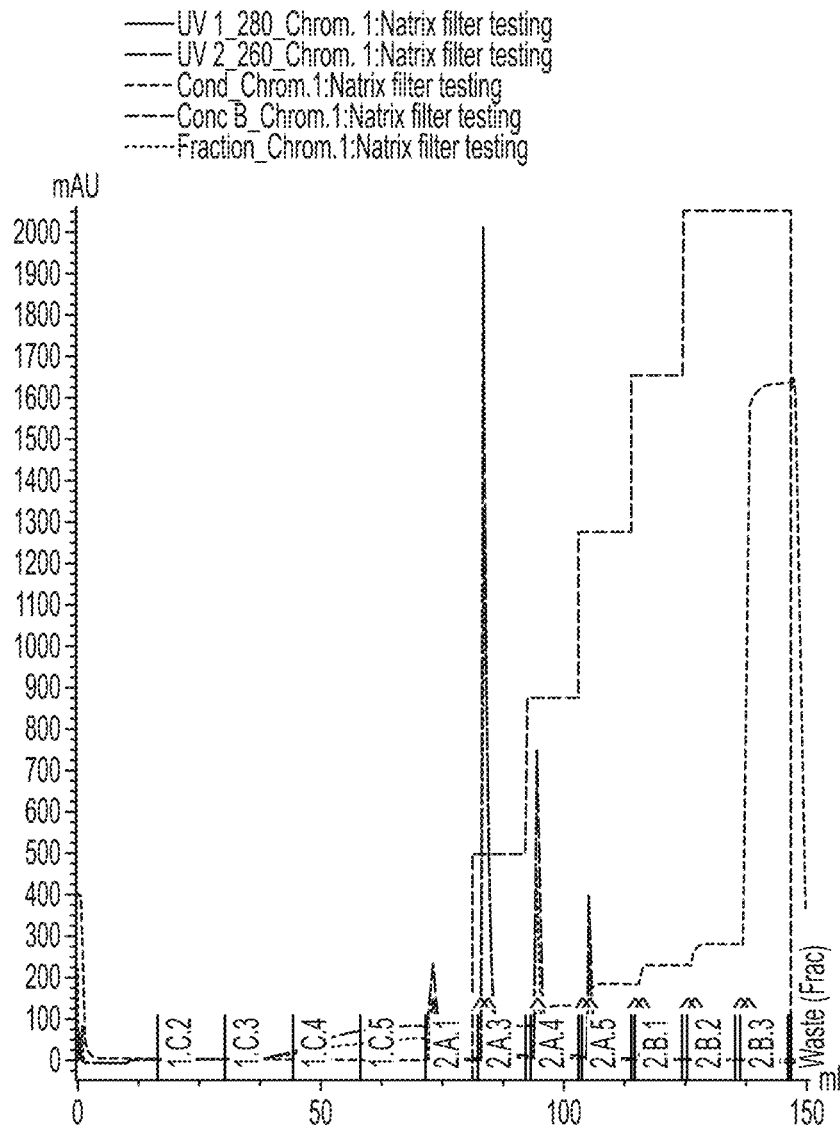

Chromatograms, exact running conditions and yields are shown in FIG. 15. The results for the Sartobind Q and Sartobind STIC showed minimal binding of C36 at salt concentrations below ~150 mM NaCl. The POROS XS chromatography resin is eluted in 20 mM Bis-Tris with a 30-300 mM NaCl salt gradient and the eluate is expected to be at a salt concentration near 150 mM. Based on these experiments the Sartobind Q and Sartobind STIC were selected as favorable candidates for further evaluation.

Conversely, product binding was observed at salt concentrations well below 150 mM for the Natrix membrane. Based on this, the Natrix membrane was eliminated from further evaluation.

Sartobind Q Results in Higher Yields in Comparison to Sartobind STIC

Product runs were performed comparing Sartobind Q and Sartobind STIC absorbers. Sartobind Q and Sartobind STIC were tested with equilibration and wash conditions that aligned with expected POROS XS elution conditions. Although AEX membrane absorbers are designed to be disposable, a high conductivity wash and strip were included in these experiments to allow quantification of material that was retained by the membrane at lower strength. The experimental conditions for these product runs are shown in Table 10 below.

TABLE 10

Experimental Conditions for Product Runs

| Parameter | |
|---|---|
| Membrane | Sartobind Q and Sartobind STIC |
| Membrane Volume | 0.08 mL (Pico size) |
| Flow Rate | 5 or 30 membrane volumes/min (MV/min) |
| Loading target | >250 g/L membrane |

| Segment | Buffer | Vol |
|---|---|---|
| Equilibration | 20 mM Bis-Tris, 100 mM NaCl, pH 6.0 | As needed |
| Load | 27 Jan. 2016 POROS XS Eluate, Cycle 1 | ~25 mL |
| EQ Wash | 20 mM Bis-Tris, 100 mM NaCl, pH 6.0 | 20 mL |
| Wash 2 | 20 mM Bis-Tris, 300 mM NaCl, pH 6.0 | 20 mL |
| Strip | 20 mM Bis Tris, 1M NaCl, pH 6.0 | 20 mL |

Figure 16A:
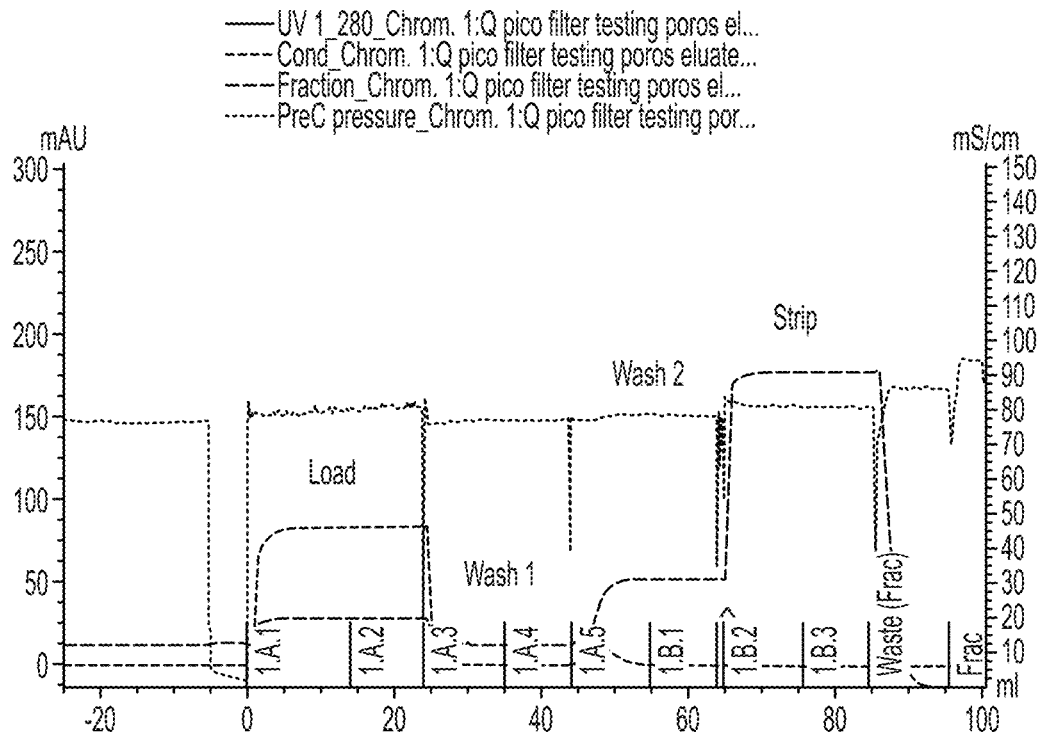
FIG. 16 depicts a series of chromatograms that show product runs for Sartobind Q (panel A), Sartobind STIC at 30 MV/min (panel B), and Sartobind STIC at 5 MV/min (panel C).
Figure 16B:
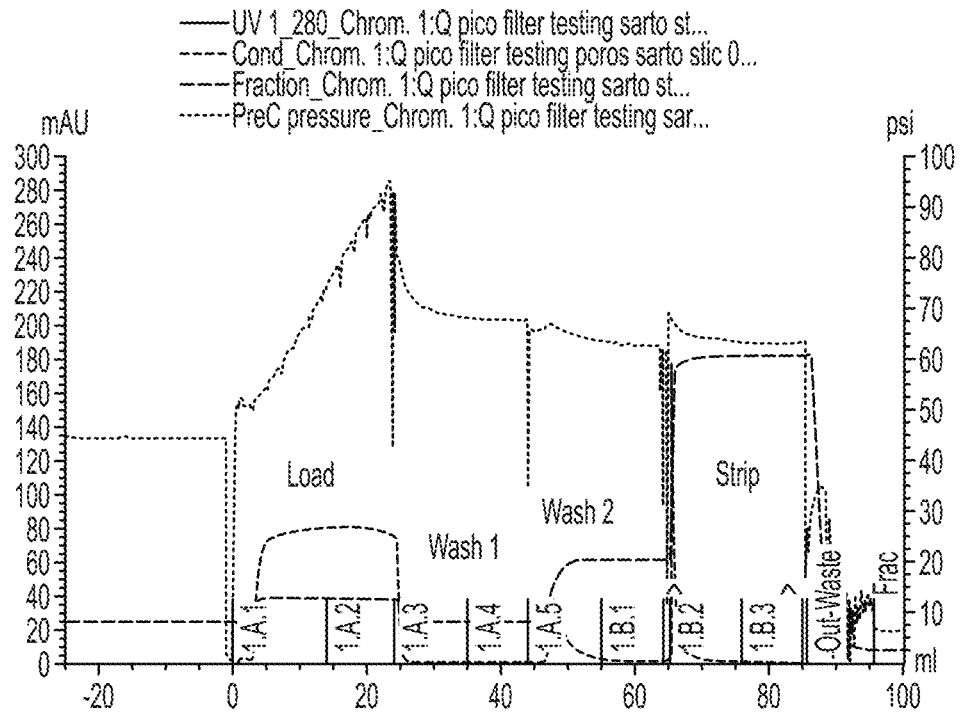
Figure 16C:
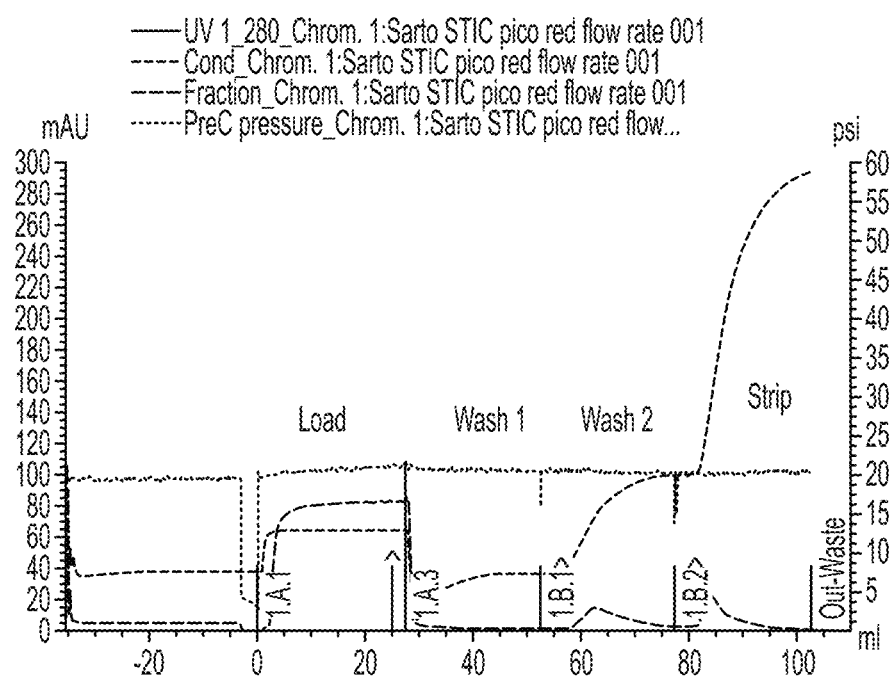

Chromatograms of the results of these experiments are shown in FIG. 16. These results are summarized in Table 11 below.

TABLE 11

Results for Product Runs - Yield and HCP Content

| Description | Flow rate (MV/min) | Load conductivity (mS/cm) | kg protein/L membrane | Yield | Protein Conc., mg/ml | HCP, ng/ml | HCP, ng/mg | Log Clearance |
|---|---|---|---|---|---|---|---|---|
| POROS XS Eluate, Cycle 1 | — | — | — | — | 0.66 | 2121.1 | 3213.8 | — |
| Sartobind Q | 30 | 19.51 | 0.245 | 95% | 0.56 | 1315.3 | 2348.8 | 0.14 |
| Sartobind STIC | 30 | 18.99 | 0.237 | 82% | — | — | — | — |
| Sartobind STIC | 5 | 18.56 | 0.259 | 91% | 0.68 | 1334.7 | 1962.8 | 0.21 |

The $A_{280}$ traces in each chromatogram show how well the protein flows through the filter during the load phase and whether bound material is released by the high conductivity wash and strip phases. The Sartobind Q had a slightly better yield compared to the STIC, corresponding to the smaller wash 2 peak and absent strip peak for the Q run. The Sartobind Q was also more robust in terms of flow characteristics; the membrane was able to operate at an inlet pressure below 35 psi at a high flow rate of 30 MV/min Conversely, pressures above 90 psi were observed when operating the STIC at 30 MV/min. In order to address this, the process flow rate was reduced to 5 MV/min. A flow rate of 5 MV/min corresponds to 8 LPM for the 1.6 L mega size membrane, which is typical for the 500 L scale. At 8 LPM the flow rate is high enough to minimize processing time and is achievable using a simple peristaltic pump. However, despite the improvement in operation at a lower flow rate, the yield for the STIC was still lower than the Sartobind Q (91% versus 95%).

Analysis of host cell protein was performed on the flow through pool by CHOP ELISA. Under ideal conditions, AEX membranes are expected to provide several logs of HCP clearance. However, the observed clearance was <1 log for both membranes. The Sartobind STIC had a slightly better clearance of 0.2 log, given the salt tolerant nature of this device. The poor HCP clearance for both absorbers could be due to the high salt conditions of the load material or the relatively high HCP content of the load (>2000 ng/ml).

These data show that the Sartobind Q had slightly higher yields compared to the Sartobind STIC (95% versus 82-91%) but the Sartobind STIC showed slightly better HCP clearance (0.21 versus 0.14). The STIC was also susceptible to pressure build-up at high flow rates. A maximum flow rate of 5 MV/min is recommended for both absorbers for manufacturing convenience and avoidance of high inlet pressures during operations.

Sartobind Q has Superior DNA Clearance in Comparison to Sartobind STIC

Sartobind Q and Sartobind STIC were tested at equilibration and wash conditions that aligned with the expected POROS XS elution conditions. A high conductivity wash and strip were again included in the experiments to allow quantification of material that was retained by the membrane at lower ionic strengths.

Lambda DNA (Thermo Fischer, Part Number: SD0011, Lot number: 1304003VS) was used for an initial spiking experiment without product (i.e., a buffer blank run), which was tested by PicoGreen. Subsequent spiking runs were done with CHO DNA (Cygnus, Part number: D552, Lot Number: 71211A, 9.4 µg/mL) and with rhC1-INH load material from previous runs. Fractions from these experiments were tested by qPCR. Run conditions for CHO DNA spiking experiments are provided in Table 12.

TABLE 12

Experimental Conditions for CHO DNA Spiking Runs

| Parameter | |
|---|---|
| Membrane | Sartobind Q and Sartobind STIC |
| Membrane Volume | 0.08 mL (Pico size) |
| Flow Rate | 5 or 30 membrane volumes/min (MV/min) |
| Loading target | >250 g/L membrane |

TABLE 12-continued

Experimental Conditions for CHO DNA Spiking Runs

| Segment | Buffer | Vol |
|---|---|---|
| Equilibration | 20 mM Bis-Tris, 100 mM NaCl, pH 6.0 | As needed |
| Load | 27 Jan. 2016 POROS XS Eluate, Cycle 1 | ~25 mL |
| EQ Wash | 20 mM Bis-Tris, 100 mM NaCl, pH 6.0 | 20 mL |
| Wash 2 | 20 mM Bis-Tris, 300 mM NaCl, pH 6.0 | 20 mL |
| Strip | 20 mM Bis Tris, 1M NaCl, pH 6.0 | 20 mL |

Figure 17:
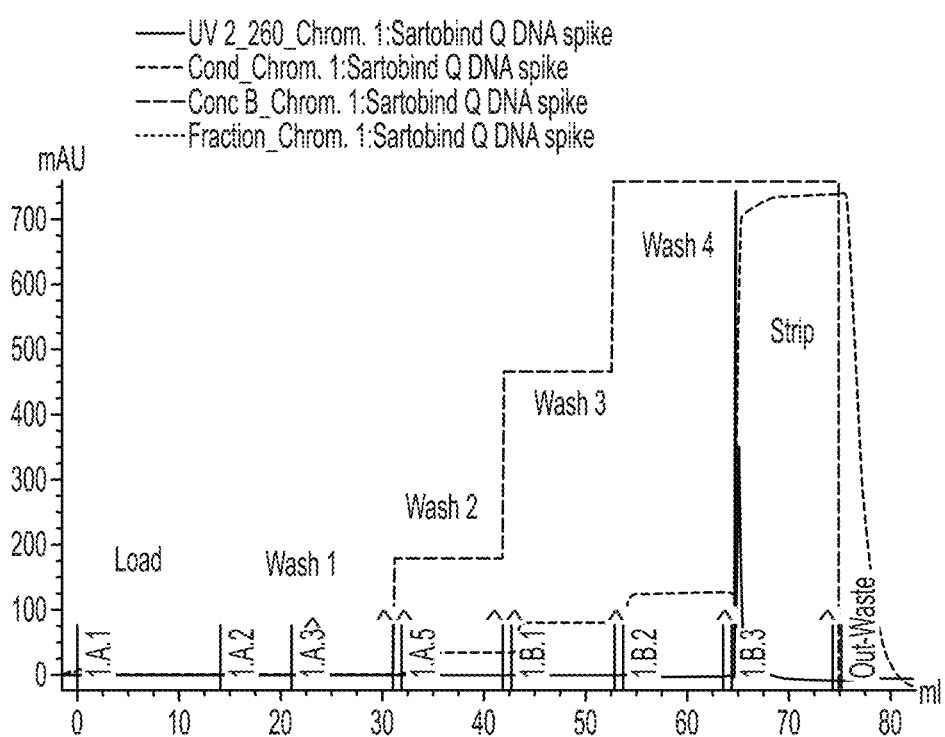
FIG. 17 depicts a chromatogram that shows a DNA spike blank run with Sartobind Q.

An initial test was done with buffers only to determine the capability of the Sartobind Q for DNA clearance. The load material consisted of 360 µL of lambda DNA stock (298 ng/µL) added to 20 mL of 20 mM Bis-Tris, 30 mM NaCl, pH 6.0. The resulting DNA concentration for the load material was measured by $A_{260}$ to be 5.5 ng/µl DNA. Several high conductivity washes were performed after the load and wash phase (see FIG. 17). Effluent fractions were collected and tested for DNA content by PicoGreen. The rhC1-INH protein was excluded from this experiment since it interferes with the PicoGreen assay. The purpose of the experiment was to estimate the levels of DNA clearance possible at the expected buffer conditions for the step. The amount of DNA measured in the unbound fraction was 0.874 pg, demonstrating a clearance of 5.1 log. DNA was bound strongly to the membrane, as evidenced by undetectable levels of DNA in subsequent high salt washes. Some DNA (26% of the load) was released from the filter with a 2 M NaCl strip.

Figure 18A:
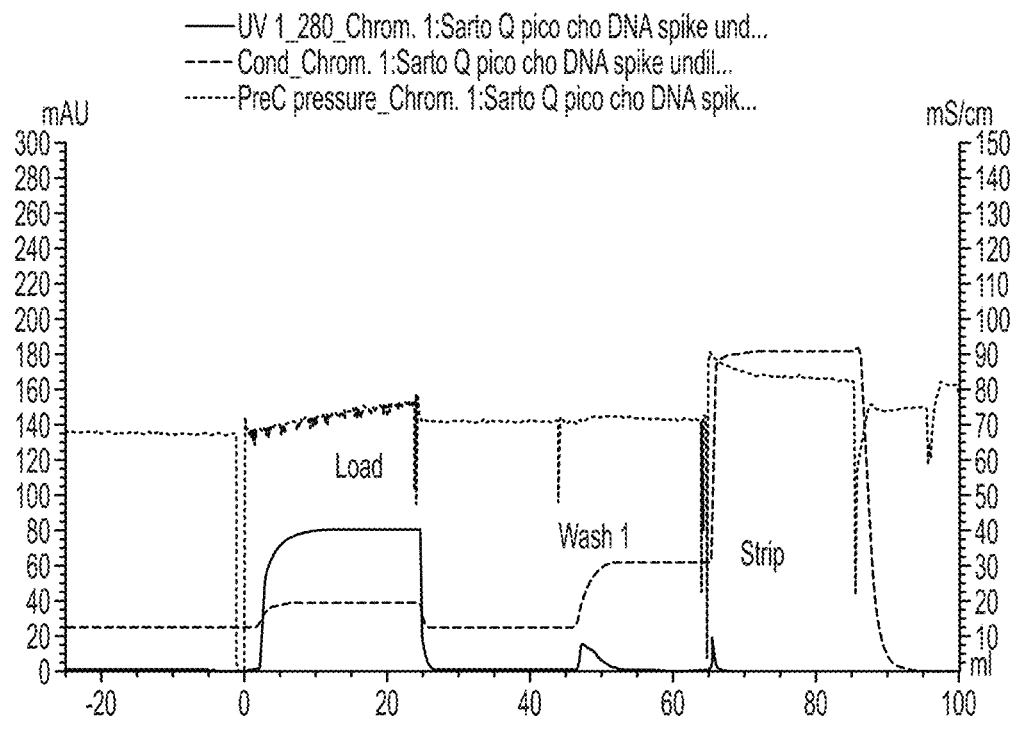
FIG. 18 depicts a series of chromatograms that show the results of a DNA spiking study followed by rhC1-INH purification.
Figure 18B:
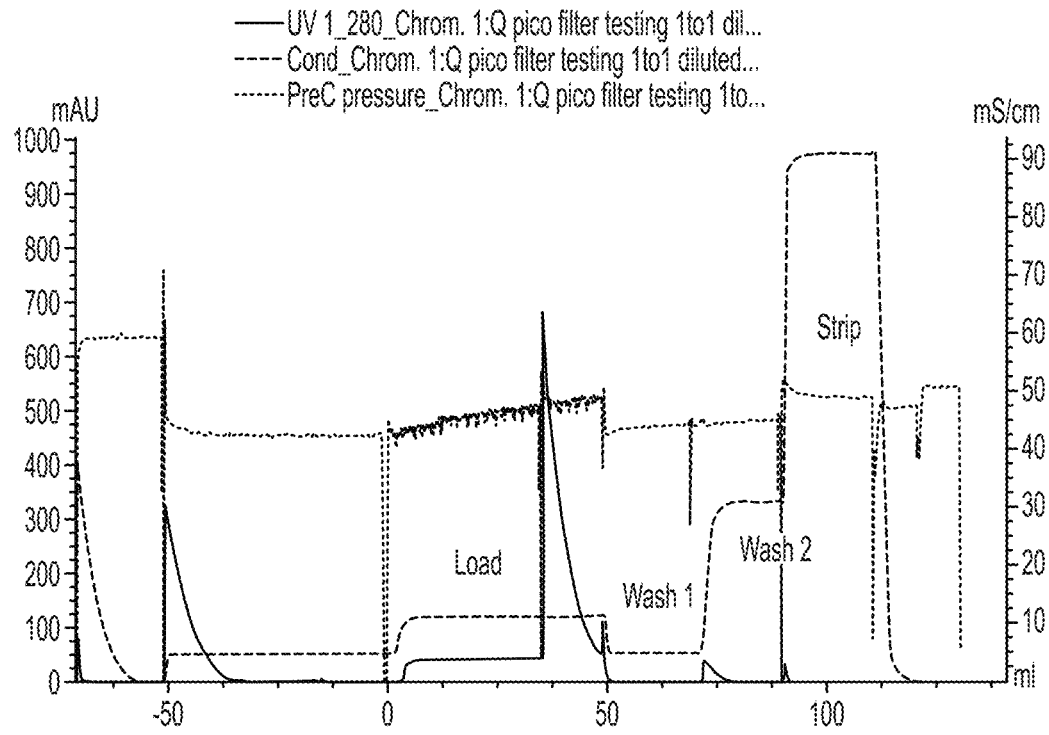
Figure 18C:
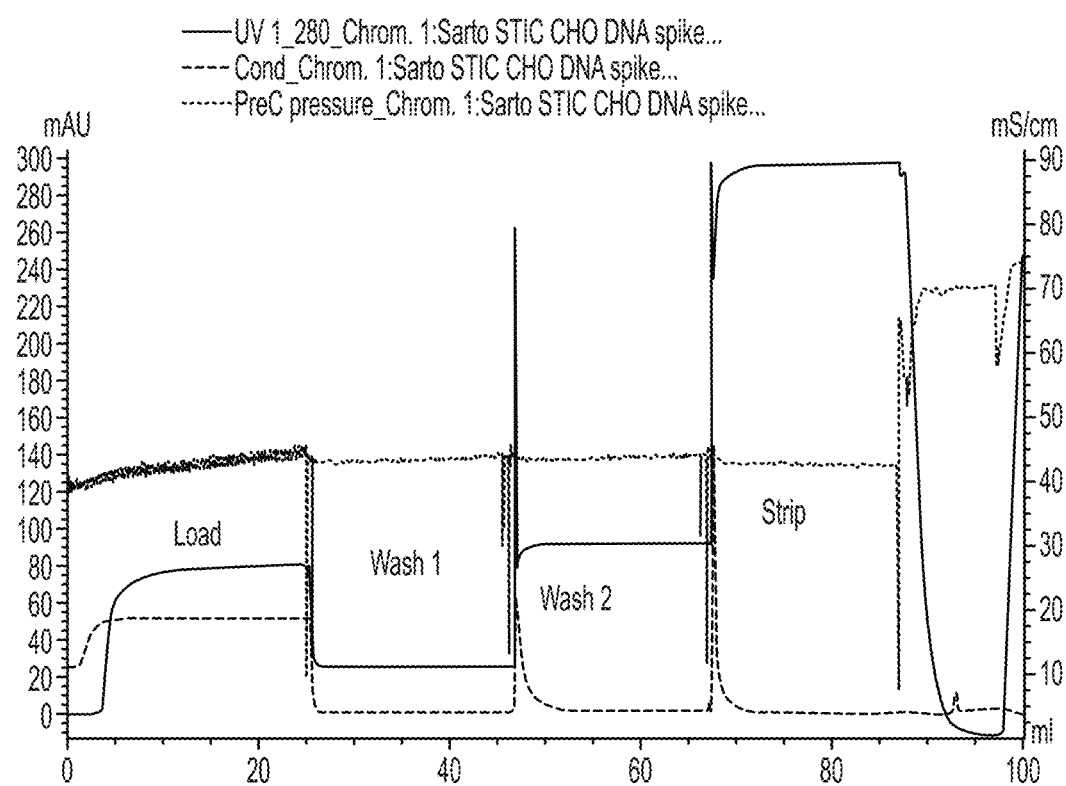

Spiking studies with CHO DNA were done with both Q and STIC membranes. 1 mL of 9.4 µg/ml concentration CHO DNA was added to 25-30 mL of POROS XS Cycle 1 eluate to serve as the load material for each experiment. Samples were assayed by qPCR by Shire. Chromatograms for each of these experiments are given in FIG. 18. The results showed a DNA log clearance of >4.1 and 3.7 for Sartobind Q with undiluted and diluted load material, respectively. While a diluted load material would not be expected to improve the DNA clearance the diluted load experiments did experience abnormal pressure spikes (see FIG. 18, panel B) during processing, which may have contributed to this lower result. By comparison, the clearance for the Sartobind STIC was 2.5 log. This last result was unexpected given that the Sartobind STIC was expected to perform better at the high salt conditions of the POROS XS eluate. Consistent with previous results, the Sartobind STIC had a slightly lower yield than the Sartobind Q. The results are summarized in Table 13 below. Collectively, these data indicate that Sartobind Q has superior performance for yield and DNA clearance.

TABLE 13

Results from Product Runs - Yield and DNA Content

| Description | Conductivity (mS/cm) | Yield | Flow rate (MV/min) | Residual CHO DNA (ng/mL) | Protein Concentration, mg/ml | DNA, ng/mg | DNA, pg/mg | Log Clearance |
|---|---|---|---|---|---|---|---|---|
| Sartobind Q Undiluted Load | 20.71 | — | 30 | 201.087 | 0.64 | 314.2 | 314198 | — |
| Sartobind Q FT + wash | — | 96% | — | <0.012 | 0.53 | 0.02 | 23 | >4.1 |
| Sartobind Q Diluted Load | 11.56 | — | 30 | 80.499 | 0.32 | 251.6 | 251561 | — |
| Sartobind Q FT + wash | — | 93% | — | 0.014 | 0.30 | 0.05 | 46 | 3.7 |
| Sartobind STIC DNA Load | 18.56 | — | 5 | 250.433 | 0.64 | 391 | 391302 | — |
| Sartobind STIC FT + Wash | — | 88% | — | 0.463 | 0.40 | 1.16 | 1158 | 2.5 |

Max Load Run for Sartobind Q

Experiments were performed to test the Sartobind Q filter at max load. The experimental design for these experiments is presented in Table 14 below.

TABLE 14

Experimental Conditions for CHO DNA Spiking Runs

| Parameter | |
|---|---|
| Membrane | Sartobind Q Single Sep |
| Membrane Volume | 1 mL (Nano size, 4 mm bed height) |
| Flow Rate | 5 membrane volumes/min (MV/min), or 5 ml/min |
| Loading target | >500 g/L membrane |

| Segment | Buffer | Vol |
|---|---|---|
| Equilibration | 20 mM Bis-Tris, 100 mM NaCl, pH 6.0 | 50 mL |
| Load | 27 Jan. 2016 POROS XS Eluate, Cycle 1 | 760 mL |
| EQ Wash | 20 mM Bis-Tris, 100 mM NaCl, pH 6.0 | 100 mL |
| Wash 2 | 20 mM Bis-Tris, 300 mM NaCl, pH 6.0 | 100 mL |
| Strip | 20 mM Bis Tris, 1M NaCl, pH 6.0 | 100 mL |

Figure 19:
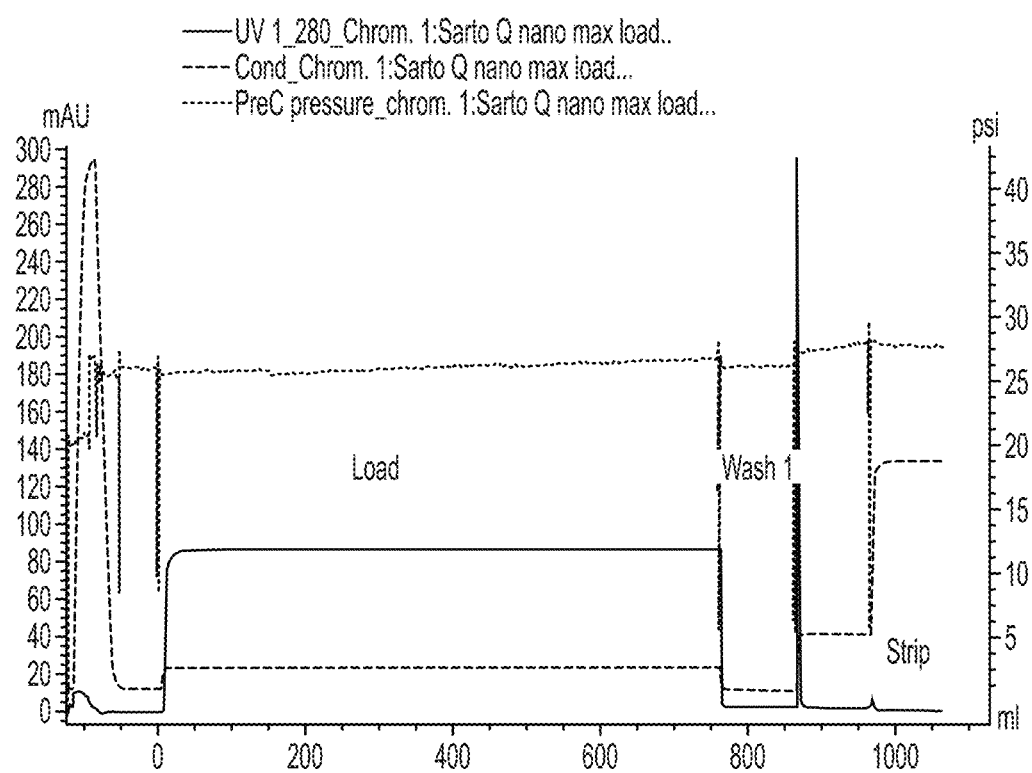
FIG. 19 is a chromatogram that shows the results of a Max Load run with Sartobind Q.

These experiments showed favorable results for loading up to 605 g/Lm, two times that required at the 500 L scale. Pressure increase was minimal throughout the experiment. The data from these experiments is shown in Table 15 and in FIG. 19.

TABLE 15

Results from Max Load Experiments Using Sartobind Q

| Description | Conductivity (mS/cm) | Loading (g/Lm) | Yield | HCP (ng/mg) | HCP Log Clearance |
|---|---|---|---|---|---|
| Load | 19.58 | 605 | — | 3108 | — |
| FT + wash | — | — | 101% | 2402 | 0.11 |

Sartobind Q after Gigacap Q

Additional experiments were performed to test performance of the membrane after GigacapQ.

The experimental design and run conditions for CHO DNA spiking experiments are shown in Table 16.

TABLE 16

Experimental Conditions for CHO DNA Spiking Runs

| Parameter | |
|---|---|
| Membrane | Sartobind Q Single Sep |
| Membrane Volume | 0.08 mL (Pico size) |
| Flow Rate | 5 membrane volumes/min (MV/min), or 5 ml/min |
| Loading target | >500 g/L membrane |

| Segment | Buffer | Vol |
|---|---|---|
| Equilibration | 50 mM Phosphate, pH 7.0 | 50 mL |
| Load | 26 Jan. 2016 GigacapQ Eluate, Cycle 2 | 13 mL |
| EQ Wash | 50 mM Phosphate, pH 7.0 | 30 mL |
| Wash 2 | 50 mM Phosphate, 150 mM, pH 7.0 | 30 mL |
| Wash 3 | 50 mM Phosphate, 300 mM, pH 7.0 | 30 mL |
| Strip | 20 mM Bis Tris, 1M NaCl, pH 6.0 | 30 mL |

Figure 20:
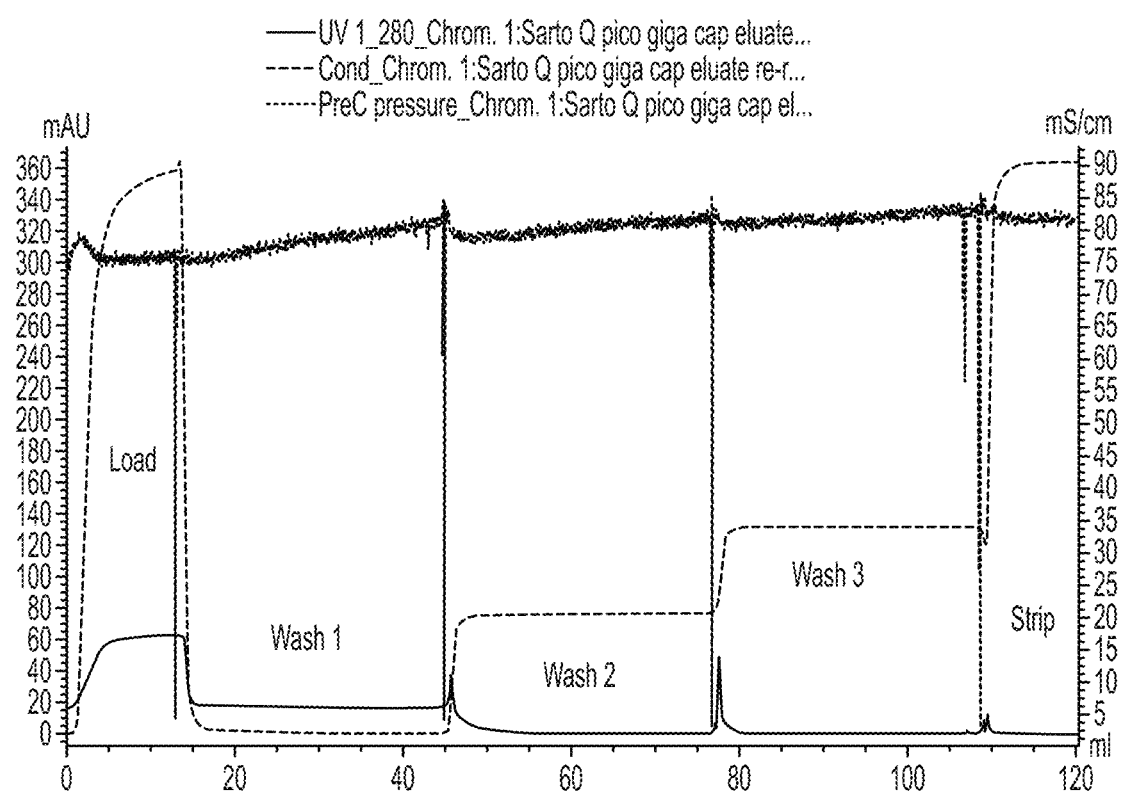
FIG. 20 is a chromatogram that shows the results of an experiment designed to assess the performance of the Sartobind Q membrane after GigacapQ.

These results indicated lower yield for the Sartobind Q with the Gigacap Q eluate. The chromatogram, shown in FIG. 20, also indicates that some binding occurred on the membrane. The process conditions were 50 mM phosphate buffer, pH 7.0, and load conductivity 17 mS. Given the low pI of rhC1-INH, a lower yield at high pH is probable. There was no improvement for HCP clearance at the higher pH condition, which can be indicative of virus clearance for virus with similar pI values to HCP.

Summary of Results

Collectively this example details a set of experiments aimed at identifying a new DNA clearance step for the rhC1-INH downstream process. Anion exchange chromatography is one choice as a DNA clearance step since the very low pI of DNA causes it to bind to anion exchange ligands at almost any pH. However, the low pI of rhC1-INH can allow the rhC1-INH to bind to anion exchange membranes as well. Sartobind Q, Sartobind STIC, and Natrix AEX membrane absorbers were tested for suitability after the second column step of the current rhC1-INH process. Natrix was eliminated early from the study since rhC1-INH bound to the membrane, resulting in a low yield for this membrane. Sartobind Q and Sartobind STIC were evaluated further with DNA spiking studies and Sartobind Q was selected based on having superior yield and DNA clearance compared to the STIC. Further experiments showed that Sartobind Q has superior performance for yield and DNA clearance.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

The invention claimed is:

1. A composition comprising a purified recombinant human C1 esterase inhibitor (rhC1-INH) having an amino acid sequence 100% identical to SEQ ID NO:1 or SEQ ID NO:2, wherein the purified recombinant rhC1-INH has a glycosylation profile comprising 10-20% neutral glycans, about 26% mono-sialylated glycans, about 35% di-sialylated glycans, about 17% tri-sialylated glycans, and about 5% tetra-sialylated glycans, and wherein the purified rhC1-INH has a half-life similar to or longer than plasma derived human C1 esterase inhibitor.

2. The composition of claim 1, wherein the purified rhC1-INH has a half-life of 10, 15, 20, 25, 30, 35, 40, 45, 50, 55, 60, 65, or 70 hours.

3. The composition of claim 1, wherein the purified rhC1-INH has a half-life in the range of 80%-120% of the half-life of plasma-derived human C1 esterase inhibitor.

4. A pharmaceutical composition comprising the composition comprising the purified rhC1-INH protein of claim 1, and a pharmaceutically acceptable carrier.

5. A kit comprising a pharmaceutical composition of claim 4.

6. A method of producing a recombinant human C1 esterase inhibitor (rhC1-INH) comprising the steps of:
providing a host cell engineered to express the rhC1-INH having an amino acid sequence 100% identical to SEQ ID NO:1 or SEQ ID NO:2, wherein the purified recombinant rhC1-INH has a glycosylation profile comprising 10-20% neutral glycans, about 26% mono-sialylated glycans, about 35% di-sialylated glycans, about 17% tri-sialylated glycans, and about 5% tetra-sialylated glycans; and culturing the host cell under conditions suitable for the cell to produce the rhC1-INH, wherein the conditions comprise feeding the cells with a culture medium comprising a glycosylation modulator for at least a period of time.

7. The method of claim 6, wherein the cells produce the rhCl-INH protein at a specific productivity rate of greater than about 5 picogram/cell/day.

8. The method of claim 6, wherein the cells produce the rhC1-INH protein at harvest titer of 5, 6, 8, 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 mg per liter per day.

9. A method for large-scale production of a recombinant human C1 esterase inhibitor (rhC1-INH) protein in mammalian cells, comprising culturing mammalian cells expressing the rhCl-INH protein in suspension in a large-scale culture vessel, wherein the rhC1-INH protein has an amino acid sequence 100% identical to SEQ ID NO:1 or SEQ ID NO:2, wherein the purified recombinant rhCl-INH has a glycosylation profile comprising 10-20% neutral glycans, about 26% mono-sialylated glycans, about 35% di-sialylated glycans, about 17% tri-sialylated glycans, and about 5% tetra-sialylated glycans, and wherein the rhC1-INH has a half-life similar to or longer than human plasma derived Cl esterase inhibitor.

\* \* \* \* \*

SEQUENCE LISTING

```
<160> NUMBER OF SEQ ID NOS: 4

<210> SEQ ID NO 1
<211> LENGTH: 478
<212> TYPE: PRT
<213> ORGANISM: Homo sapiens

<400> SEQUENCE: 1

Asn Pro Asn Ala Thr Ser Ser Ser Gln Asp Pro Glu Ser Leu Gln
1               5                  10                 15

Asp Arg Gly Glu Gly Lys Val Ala Thr Thr Val Ile Ser Lys Met Leu
                20                 25                 30

Phe Val Glu Pro Ile Leu Glu Val Ser Ser Leu Pro Thr Thr Asn Ser
                35                 40                 45

Thr Thr Asn Ser Ala Thr Lys Ile Thr Ala Asn Thr Thr Asp Glu Pro
    50                 55                 60

Thr Thr Gln Pro Thr Thr Glu Pro Thr Thr Gln Pro Thr Ile Gln Pro
65                  70                 75                  80

Thr Gln Pro Thr Thr Gln Leu Pro Thr Asp Ser Pro Thr Gln Pro Thr
                85                 90                 95

Thr Gly Ser Phe Cys Pro Gly Pro Val Thr Leu Cys Ser Asp Leu Glu
                100                105                110

Ser His Ser Thr Glu Ala Val Leu Gly Asp Ala Leu Val Asp Phe Ser
            115                120                125

Leu Lys Leu Tyr His Ala Phe Ser Ala Met Lys Lys Val Glu Thr Asn
        130                135                140

Met Ala Phe Ser Pro Phe Ser Ile Ala Ser Leu Leu Thr Gln Val Leu
145                150                 155                160

Leu Gly Ala Gly Glu Asn Thr Lys Thr Asn Leu Glu Ser Ile Leu Ser
                165                170                175

Tyr Pro Lys Asp Phe Thr Cys Val His Gln Ala Leu Lys Gly Phe Thr
                180                185                190

Thr Lys Gly Val Thr Ser Val Ser Gln Ile Phe His Ser Pro Asp Leu
            195                200                205

Ala Ile Arg Asp Thr Phe Val Asn Ala Ser Arg Thr Leu Tyr Ser Ser
        210                215                220

Ser Pro Arg Val Leu Ser Asn Asn Ser Asp Ala Asn Leu Glu Leu Ile
225                230                 235                240

Asn Thr Trp Val Ala Lys Asn Thr Asn Lys Ile Ser Arg Leu Leu
                245                250                255

Asp Ser Leu Pro Ser Asp Thr Arg Leu Val Leu Leu Asn Ala Ile Tyr
                260                265                270

Leu Ser Ala Lys Trp Lys Thr Thr Phe Asp Pro Lys Lys Thr Arg Met
            275                280                285

Glu Pro Phe His Phe Lys Asn Ser Val Ile Lys Val Pro Met Met Asn
                290                295                300
```

```
Ser Lys Lys Tyr Pro Val Ala His Phe Ile Asp Gln Thr Leu Lys Ala
305                 310                 315                 320

Lys Val Gly Gln Leu Gln Leu Ser His Asn Leu Ser Leu Val Ile Leu
            325                 330                 335

Val Pro Gln Asn Leu Lys His Arg Leu Glu Asp Met Glu Gln Ala Leu
                340                 345                 350

Ser Pro Ser Val Phe Lys Ala Ile Met Glu Lys Leu Glu Met Ser Lys
            355                 360                 365

Phe Gln Pro Thr Leu Leu Thr Leu Pro Arg Ile Lys Val Thr Thr Ser
    370                 375                 380

Gln Asp Met Leu Ser Ile Met Glu Lys Leu Glu Phe Phe Asp Phe Ser
385                 390                 395                 400

Tyr Asp Leu Asn Leu Cys Gly Leu Thr Glu Asp Pro Asp Leu Gln Val
                405                 410                 415

Ser Ala Met Gln His Gln Thr Val Leu Glu Leu Thr Glu Thr Gly Val
            420                 425                 430

Glu Ala Ala Ala Ala Ser Ala Ile Ser Val Ala Arg Thr Leu Leu Val
            435                 440                 445

Phe Glu Val Gln Gln Pro Phe Leu Phe Val Leu Trp Asp Gln Gln His
    450                 455                 460

Lys Phe Pro Val Phe Met Gly Arg Val Tyr Asp Pro Arg Ala
465                 470                 475

<210> SEQ ID NO 2
<211> LENGTH: 478
<212> TYPE: PRT
<213> ORGANISM: Artificial Sequence
<220> FEATURE:
<223> OTHER INFORMATION: Synthetic Polypeptide

<400> SEQUENCE: 2

Asn Pro Asn Ala Thr Ser Ser Ser Gln Asp Pro Glu Ser Leu Gln
1               5                   10                  15

Asp Arg Gly Glu Gly Lys Val Ala Thr Thr Val Ile Ser Lys Met Leu
            20                  25                  30

Phe Val Glu Pro Ile Leu Glu Val Ser Ser Leu Pro Thr Thr Asn Ser
            35                  40                  45

Thr Thr Asn Ser Ala Thr Lys Ile Thr Ala Asn Thr Thr Asp Glu Pro
    50                  55                  60

Thr Thr Gln Pro Thr Thr Glu Pro Thr Thr Gln Pro Thr Ile Gln Pro
65                  70                  75                  80

Thr Gln Pro Thr Thr Gln Leu Pro Thr Asp Ser Pro Thr Gln Pro Thr
                85                  90                  95

Thr Gly Ser Phe Cys Pro Gly Pro Val Thr Leu Cys Ser Asp Leu Glu
            100                 105                 110

Ser His Ser Thr Glu Ala Val Leu Gly Asp Ala Leu Val Asp Phe Ser
            115                 120                 125

Leu Lys Leu Tyr His Ala Phe Ser Ala Met Lys Lys Val Glu Thr Asn
    130                 135                 140

Met Ala Phe Ser Pro Phe Ser Ile Ala Ser Leu Leu Thr Gln Val Leu
145                 150                 155                 160

Leu Gly Ala Gly Glu Asn Thr Lys Thr Asn Leu Glu Ser Ile Leu Ser
                165                 170                 175

Tyr Pro Lys Asp Phe Thr Cys Val His Gln Ala Leu Lys Gly Phe Thr
            180                 185                 190
```

Thr Lys Gly Val Thr Ser Val Ser Gln Ile Phe His Ser Pro Asp Leu
            195                 200                 205

Ala Ile Arg Asp Thr Phe Val Asn Ala Ser Arg Thr Leu Tyr Ser Ser
            210                 215                 220

Ser Pro Arg Val Leu Ser Asn Asn Ser Asp Ala Asn Leu Glu Leu Ile
225                 230                 235                 240

Asn Thr Trp Val Ala Lys Asn Thr Asn Lys Ile Ser Arg Leu Leu
            245                 250                 255

Asp Ser Leu Pro Ser Asp Thr Arg Leu Val Leu Asn Ala Ile Tyr
            260                 265                 270

Leu Ser Ala Lys Trp Lys Thr Thr Phe Asp Pro Lys Lys Thr Arg Met
            275                 280                 285

Glu Pro Phe His Phe Lys Asn Ser Val Ile Lys Val Pro Met Met Asn
            290                 295                 300

Ser Lys Lys Tyr Pro Val Ala His Phe Ile Asp Gln Thr Leu Lys Ala
305                 310                 315                 320

Lys Val Gly Gln Leu Gln Leu Ser His Asn Leu Ser Leu Val Ile Leu
            325                 330                 335

Val Pro Gln Asn Leu Lys His Arg Leu Glu Asp Met Glu Gln Ala Leu
            340                 345                 350

Ser Pro Ser Val Phe Lys Ala Ile Met Glu Lys Leu Glu Met Ser Lys
            355                 360                 365

Phe Gln Pro Thr Leu Leu Thr Leu Pro Arg Ile Lys Val Thr Thr Ser
            370                 375                 380

Gln Asp Met Leu Ser Ile Met Glu Lys Leu Glu Phe Phe Asp Phe Ser
385                 390                 395                 400

Tyr Asp Leu Asn Leu Cys Gly Leu Thr Glu Asp Pro Asp Leu Gln Val
            405                 410                 415

Ser Ala Met Gln His Gln Thr Val Leu Glu Leu Thr Glu Thr Gly Val
            420                 425                 430

Glu Ala Ala Ala Ala Ser Ala Ile Ser Val Ala Arg Thr Leu Leu Val
            435                 440                 445

Phe Glu Val Gln Gln Pro Phe Leu Phe Val Leu Trp Asp Gln Gln His
            450                 455                 460

Lys Phe Pro Val Phe Met Gly Arg Val Tyr Asp Pro Arg Ala
465                 470                 475

<210> SEQ ID NO 3
<211> LENGTH: 381
<212> TYPE: PRT
<213> ORGANISM: Artificial Sequence
<220> FEATURE:
<223> OTHER INFORMATION: Synthetic Polypeptide

<400> SEQUENCE: 3

Gly Ser Phe Cys Pro Gly Pro Val Thr Leu Cys Ser Asp Leu Glu Ser
1               5                   10                  15

His Ser Thr Glu Ala Val Leu Gly Asp Ala Leu Val Asp Phe Ser Leu
            20                  25                  30

Lys Leu Tyr His Ala Phe Ser Ala Met Lys Lys Val Glu Thr Asn Met
            35                  40                  45

Ala Phe Ser Pro Phe Ser Ile Ala Ser Leu Leu Thr Gln Val Leu Leu
            50                  55                  60

Gly Ala Gly Glu Asn Thr Lys Thr Asn Leu Glu Ser Ile Leu Ser Tyr
65                  70                  75                  80

Pro Lys Asp Phe Thr Cys Val His Gln Ala Leu Lys Gly Phe Thr Thr
            85                  90                  95

Lys Gly Val Thr Ser Val Ser Gln Ile Phe His Ser Pro Asp Leu Ala
            100                 105                 110

Ile Arg Asp Thr Phe Val Asn Ala Ser Arg Thr Leu Tyr Ser Ser Ser
            115                 120                 125

Pro Arg Val Leu Ser Asn Asn Ser Asp Ala Asn Leu Glu Leu Ile Asn
130                 135                 140

Thr Trp Val Ala Lys Asn Thr Asn Asn Lys Ile Ser Arg Leu Leu Asp
145                 150                 155                 160

Ser Leu Pro Ser Asp Thr Arg Leu Val Leu Leu Asn Ala Ile Tyr Leu
            165                 170                 175

Ser Ala Lys Trp Lys Thr Thr Phe Asp Pro Lys Lys Thr Arg Met Glu
            180                 185                 190

Pro Phe His Phe Lys Asn Ser Val Ile Lys Val Pro Met Met Asn Ser
            195                 200                 205

Lys Lys Tyr Pro Val Ala His Phe Ile Asp Gln Thr Leu Lys Ala Lys
            210                 215                 220

Val Gly Gln Leu Gln Leu Ser His Asn Leu Ser Leu Val Ile Leu Val
225                 230                 235                 240

Pro Gln Asn Leu Lys His Arg Leu Glu Asp Met Glu Gln Ala Leu Ser
            245                 250                 255

Pro Ser Val Phe Lys Ala Ile Met Glu Lys Leu Glu Met Ser Lys Phe
            260                 265                 270

Gln Pro Thr Leu Leu Thr Leu Pro Arg Ile Lys Val Thr Thr Ser Gln
            275                 280                 285

Asp Met Leu Ser Ile Met Glu Lys Leu Glu Phe Phe Asp Phe Ser Tyr
290                 295                 300

Asp Leu Asn Leu Cys Gly Leu Thr Glu Asp Pro Asp Leu Gln Val Ser
305                 310                 315                 320

Ala Met Gln His Gln Thr Val Leu Glu Leu Thr Glu Thr Gly Val Glu
            325                 330                 335

Ala Ala Ala Ala Ser Ala Ile Ser Val Ala Arg Thr Leu Leu Val Phe
            340                 345                 350

Glu Val Gln Gln Pro Phe Leu Phe Val Leu Trp Asp Gln Gln His Lys
            355                 360                 365

Phe Pro Val Phe Met Gly Arg Val Tyr Asp Pro Arg Ala
            370                 375                 380

<210> SEQ ID NO 4
<211> LENGTH: 381
<212> TYPE: PRT
<213> ORGANISM: Artificial Sequence
<220> FEATURE:
<223> OTHER INFORMATION: Synthetic Polypeptide

<400> SEQUENCE: 4

Gly Ser Phe Cys Pro Gly Pro Val Thr Leu Cys Ser Asp Leu Glu Ser
1               5                   10                  15

His Ser Thr Glu Ala Val Leu Gly Asp Ala Leu Val Asp Phe Ser Leu
            20                  25                  30

Lys Leu Tyr His Ala Phe Ser Ala Met Lys Lys Val Glu Thr Asn Met
            35                  40                  45

Ala Phe Ser Pro Phe Ser Ile Ala Ser Leu Leu Thr Gln Val Leu Leu
50                  55                  60

-continued

| | | | | | | | | | | | | |
|---|---|---|---|---|---|---|---|---|---|---|---|---|
| Gly | Ala | Gly | Glu | Asn | Thr | Lys | Thr | Asn | Leu | Glu | Ser | Ile | Leu | Ser | Tyr |
| 65 | | | | | 70 | | | | | 75 | | | | | 80 |

Gly Ala Gly Glu Asn Thr Lys Thr Asn Leu Glu Ser Ile Leu Ser Tyr
65                    70                  75                  80

Pro Lys Asp Phe Thr Cys Val His Gln Ala Leu Lys Gly Phe Thr Thr
                    85                  90                  95

Lys Gly Val Thr Ser Val Ser Gln Ile Phe His Ser Pro Asp Leu Ala
                100                 105                 110

Ile Arg Asp Thr Phe Val Asn Ala Ser Arg Thr Leu Tyr Ser Ser Ser
            115                 120                 125

Pro Arg Val Leu Ser Asn Asn Ser Asp Ala Asn Leu Glu Leu Ile Asn
130                         135                 140

Thr Trp Val Ala Lys Asn Thr Asn Asn Lys Ile Ser Arg Leu Leu Asp
145                 150                 155                 160

Ser Leu Pro Ser Asp Thr Arg Leu Val Leu Leu Asn Ala Ile Tyr Leu
                165                 170                 175

Ser Ala Lys Trp Lys Thr Thr Phe Asp Pro Lys Lys Thr Arg Met Glu
                180                 185                 190

Pro Phe His Phe Lys Asn Ser Val Ile Lys Val Pro Met Met Asn Ser
            195                 200                 205

Lys Lys Tyr Pro Val Ala His Phe Ile Asp Gln Thr Leu Lys Ala Lys
210                 215                 220

Val Gly Gln Leu Gln Leu Ser His Asn Leu Ser Leu Val Ile Leu Val
225                 230                 235                 240

Pro Gln Asn Leu Lys His Arg Leu Glu Asp Met Glu Gln Ala Leu Ser
            245                 250                 255

Pro Ser Val Phe Lys Ala Ile Met Glu Lys Leu Glu Met Ser Lys Phe
            260                 265                 270

Gln Pro Thr Leu Leu Thr Leu Pro Arg Ile Lys Val Thr Thr Ser Gln
            275                 280                 285

Asp Met Leu Ser Ile Met Glu Lys Leu Glu Phe Phe Asp Phe Ser Tyr
    290                 295                 300

Asp Leu Asn Leu Cys Gly Leu Thr Glu Asp Pro Asp Leu Gln Val Ser
305                 310                 315                 320

Ala Met Gln His Gln Thr Val Leu Glu Leu Thr Glu Thr Gly Val Glu
                325                 330                 335

Ala Ala Ala Ala Ser Ala Ile Ser Val Ala Arg Thr Leu Leu Val Phe
            340                 345                 350

Glu Val Gln Gln Pro Phe Leu Phe Val Leu Trp Asp Gln Gln His Lys
        355                 360                 365

Phe Pro Val Phe Met Gly Arg Val Tyr Asp Pro Arg Ala
            370                 375                 380